US010196616B2

(12) United States Patent
Afonso et al.

(10) Patent No.: US 10,196,616 B2
(45) Date of Patent: Feb. 5, 2019

(54) ALTERED AVIAN VIRUS FOR IN-OVO INOCULATION AND METHODS OF USE THEREOF

(71) Applicants: The United States of America, as represented by the Secretary of Agriculture, Washington, DC (US); University of Georgia Research Foundation, Inc., Athens, GA (US)

(72) Inventors: Claudio L. Afonso, Jefferson, GA (US); Valerie C. Marcano, Athens, GA (US); Nany Stivalis Cardenas Garcia, Athens, GA (US); Qingzhong Yu, Athens, GA (US); Tonya L. Taylor, Monroe, GA (US)

(73) Assignees: The United States of America, as represented by the Secretary of Agriculture, Washington, DC (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/890,575

(22) Filed: Feb. 7, 2018

(65) Prior Publication Data

US 2018/0230439 A1 Aug. 16, 2018

Related U.S. Application Data

(60) Provisional application No. 62/459,254, filed on Feb. 15, 2017.

(51) Int. Cl.

| | |
|---|---|
| ***C12N 7/00*** | (2006.01) |
| ***C07K 14/54*** | (2006.01) |
| ***A61K 39/17*** | (2006.01) |
| ***A61K 39/12*** | (2006.01) |
| ***A61P 31/14*** | (2006.01) |
| *A61K 39/00* | (2006.01) |

(52) U.S. Cl.

CPC ................ *C12N 7/00* (2013.01); *A61K 39/12* (2013.01); *A61K 39/17* (2013.01); *A61P 31/14* (2018.01); *C07K 14/5406* (2013.01); *A61K 2039/5254* (2013.01); *A61K 2039/54* (2013.01); *A61K 2039/552* (2013.01); *C12N 2710/16022* (2013.01); *C12N 2760/18121* (2013.01); *C12N 2760/18134* (2013.01); *C12N 2760/18171* (2013.01)

(58) Field of Classification Search

None

See application file for complete search history.

(56) References Cited

U.S. PATENT DOCUMENTS

| | | | |
|---|---|---|---|
| 5,676,940 A | 10/1997 | Coffman et al. | |
| 5,733,556 A | 3/1998 | Schrier et al. | |
| 6,086,876 A * | 7/2000 | Karp | A61K 38/162 424/144.1 |
| 6,451,323 B1 | 9/2002 | Garcia-Sastre et al. | |
| 6,506,385 B1 * | 1/2003 | Poston | A61K 39/12 424/184.1 |
| 6,719,979 B2 | 4/2004 | Peeters et al. | |
| 7,332,169 B2 | 2/2008 | Peeters et al. | |
| 7,547,442 B2 | 6/2009 | Peeters et al. | |
| 8,173,136 B2 | 5/2012 | Cho et al. | |
| 8,591,881 B2 | 11/2013 | Palese et al. | |
| 9,387,242 B2 | 7/2016 | Palese et al. | |
| 9,950,059 B2 | 4/2018 | Yu et al. | |
| 2002/0137709 A1 | 9/2002 | Lin et al. | |
| 2003/0224017 A1 * | 12/2003 | Samal | C12N 7/00 424/214.1 |
| 2007/0128169 A1 | 6/2007 | Lewis et al. | |
| 2012/0064112 A1 | 3/2012 | Samal et al. | |
| 2013/0129780 A1 * | 5/2013 | Garcia | A61K 39/265 424/205.1 |
| 2017/0037379 A1 | 2/2017 | Palese et al. | |
| 2017/0049880 A1 | 2/2017 | Samal et al. | |

FOREIGN PATENT DOCUMENTS

| | | | |
|---|---|---|---|
| WO | 00/15853 A1 | | 3/2000 |
| WO | 2010/115133 A1 | | 10/2010 |
| WO | 2012/030720 A1 | | 3/2012 |
| WO | WO 2012/131069 | * | 10/2012 |

OTHER PUBLICATIONS

Sequence alignments of instant SEQ ID No. 1 with GenEmbl database access No. AJ621249 by Avery et al 2004.*

Sequence alignments of instant SEQ ID No. 2 with GenEmbl database access No. AJ621249 by Avery et al 2004.*

Sequence alignment of SEQ ID No. 10 with Geneseq database accession No. AOG21853 by Dan et al 2008.*

Brun, Alejandro et al., "Antigen delivery systems for veterinary vaccine development Viral-vector based delivery systems" (2208) Vaccine 26:6508-6528.

Dimitrov, Kiri M. et al., "Newcastle disease vaccines—A solved problem or a continuous challenge?", (2017) Veterinary Microbiology 206: 126-136.

Dinapoli, Joshua M., "Newcastle disease virus, a host rangeR-restricted virus, as a vaccine vector for intranasal immunization against emerging pathogens", (2007) PNAS 104(23):9788-9793.

(Continued)

*Primary Examiner* — Shanon A. Foley

(74) *Attorney, Agent, or Firm* — David L. Marks; John D. Fado; Gail E. Poulos

(57) ABSTRACT

An altered avian NDV that contains the coding sequence of avian interleukin-4 (IL-4), or a portion thereof, in the reverse orientation suppresses in-ovo IL-4 production via RNAi when administered to embryonic birds. An immunogenic composition containing this altered NDV is included in this invention. The altered avian NDV can, optionally contain a polynucleotide encoding a heterologous antigen from a heterologous avian pathogen and can produce said heterologous antigen in-ovo.

24 Claims, 16 Drawing Sheets

Specification includes a Sequence Listing.

(56) References Cited

OTHER PUBLICATIONS

Dinapoli, Joshua M. et al., "Delivery to the lower respiratory tract is required for effective immunization with Newcastle disease virus-vectored vaccines intended for humans", (2009) Vaccine 27(10):1530-1539.
Ge, Jinying et al., "Generation and Evaluation of a Newcastle Disease Virus-Based H9 Avian Influenza Live Vaccine", (2010) Avian Diseases 54:294-296.
Ge, Jinying, "Newcastle Disease Virus-Based Live Attenuated Vaccine Completely Protects Chickens and Mice from Lethal Challenge of Homologous and Heterologous H5N1 Avian Influenza VirusesLJ", (2007) Journal of Virology 81(1):150-158.
Hu, Haixia et al., "Generation and evaluation of a recombinant Newcastle disease virus expressing the glycoprotein 7 (G) of avian metapneumovirus subgroup C as a bivalent vaccine in turkeys", (2011) Vaccine 29:8624-8633.
Kapczynski, Darrell R. et al., "Protection from Clinical Disease Against Three Highly Virulent Strains of Newcastle Disease Virus After In Ova Application of an Antibody-Antigen Complex Vaccine in Maternal Antibody-Positive Chickens", (2012) Avian Diseases 56:555-560.
Marcano, Valerie, "In Ovo Vaccination Chicken Embryos Using Attenuated Recombinant Newcastle Disease Virus Vaccine", Sep. 2016, XIVth Avian Immunology Research Group (AIRG) Meeting, Herrsching, Germany, 21 slides.
Miller, Patti J. et al., "Comparison of Viral Shedding Following Vaccination With Inactivated and Live Newcastle Disease Vaccines Formulated With Wlid-Type and Recombinant Viruses" (2009) Avian Diseases 53:39-49.
Miller, Patti J., "Effects of Newcastle disease virus vaccine antibodies on the shedding and transmission of challenge viruses", (2013) Developmental and Comparative Immunology 41 :505-513.
Miller, Patti, J., "Newcastle disease: Evolution of genotypes and the related diagnostic challenges", (2010) Infection, Genetics and Evolution 10:26-35.
Nakaya, Takaaki et al., "Recombinant Newcastle Disease Virus as a Vaccine Vector", (2001) Journal of Virology 75 (23): 11868-11873.
Nayak, Baibaswata et al., "Immunization of Chickens with Newcastle Disease Virus Expressing HS Hemagglutinin Protects against Highly Pathogenic H5N1 Avian Influenza Viruses", (2009) Plos One 4(8):1-10.
Park, Man-Seang et al., "Engineered viral vaccine constructs with dual specificity: Avian influenza and Newcastle disease", (2006) PNAS 103(21):8203-8208.
Zhao, Wei et al., "Newcastle Disease Virus (NDV) Recombinants Expressing Infectious Laryngotracheitis Virus (ILT V) Glycoproteins gB and gD Protect Chickens against ILTV and NDV Challenges", (2014) Journal of Virology 88(15):8397-8406.

* cited by examiner

SEQUENCE LISTING

```
<160> NUMBER OF SEQ ID NOS: 27

<210> SEQ ID NO 1
<211> LENGTH: 411
<212> TYPE: DNA
<213> ORGANISM: Gallus gallus

<400> SEQUENCE: 1

atgagctcct cactgcccac cctgctggca ctgctggtgc tgctggccgg ccctggggct      60

gtgcccacgc tgtgcttaca gctctcagtg ccgctgatgg agagcatccg gatagtgaat     120

gacatccagg gagaggtttc ctgcgtcaag atgaacgtga cagatatctt tgcagacaat     180

aagacaaata acaaaaactga gctcttatgc aaagcctcca caattgtttg ggagagccag     240

cactgccaca agaacctgca gggtctcttc ctcaacatgc gtcagctcct gaatgccagc     300

agcacctccc tcaaggcacc atgtcccacg gcagcaggca acactacttc aatggagaag     360
```

-continued ttcctagcag acctacgtac cttcttccac caactagcta aaaataagtg a 411

<210> SEQ ID NO 2
<211> LENGTH: 411
<212> TYPE: DNA
<213> ORGANISM: Gallus gallus

<400> SEQUENCE: 2
tcacttattt ttagctagtt ggtggaagaa ggtacgtagg tctgctagga acttctccat 60
tgaagtagtg ttgcctgctg ccgtgggaca tggtgccttg agggaggtgc tgctggcatt 120
caggagctga cgcatgttga ggaagagacc ctgcaggttc ttgtggcagt gctggctctc 180
ccaaacaatt gtggaggctt tgcataagag ctcagttttg ttatttgtct tattgtctgc 240
aaagatatct gtcacgttca tcttgacgca ggaaacctct ccctggatgt cattcactat 300
ccggatgctc tccatcagcg gcactgagag ctgtaagcac agcgtgggca cagccccagg 360
gccggccagc agcaccagca gtgccagcag ggtgggcagt gaggagctca t 411

<210> SEQ ID NO 3
<211> LENGTH: 414
<212> TYPE: DNA
<213> ORGANISM: Artificial Sequence
<220> FEATURE:
<223> OTHER INFORMATION: chemically synthesized

<400> SEQUENCE: 3
gtttcactta tttttagcta gttggtggaa gaaggtacgt aggtctgcta ggaacttctc 60
cattgaagta gtgttgcctg ctgccgtggg acatggtgcc ttgagggagg tgctgctggc 120
attcaggagc tgacgcatgt tgaggaagag accctgcagg ttcttgtggc agtgctggct 180
ctcccaaaca attgtggagg ctttgcataa gagctcagtt ttgttatttg tcttattgtc 240
tgcaaagata tctgtcacgt tcatcttgac gcaggaaacc tctccctgga tgtcattcac 300
tatccggatg ctctccatca gcggcactga gagctgtaag cacagcgtgg gcacagcccc 360
agggccggcc agcagcacca gcagtgccag cagggtgggc agtgaggagc tcat 414

<210> SEQ ID NO 4
<211> LENGTH: 25
<212> TYPE: DNA
<213> ORGANISM: Gallus gallus

<400> SEQUENCE: 4
ggcagcaggc aacactactt caatg 25

<210> SEQ ID NO 5
<211> LENGTH: 25
<212> TYPE: DNA
<213> ORGANISM: Gallus gallus

<400> SEQUENCE: 5
cattgaagta gtgttgcctg ctgcc 25

<210> SEQ ID NO 6
<211> LENGTH: 55
<212> TYPE: DNA
<213> ORGANISM: Artificial Sequence
<220> FEATURE:
<223> OTHER INFORMATION: chemically synthesized

<400> SEQUENCE: 6
ctgggccctc ttagaaaaaa tacgggtaga agtaccatga gctcctcact gccca 55

-continued

<210> SEQ ID NO 7
<211> LENGTH: 51
<212> TYPE: DNA
<213> ORGANISM: Artificial Sequence
<220> FEATURE:
<223> OTHER INFORMATION: chemically synthesized

<400> SEQUENCE: 7
ggccggttgg gccctcgttt cacttatttt tagctagttg gtggaagaag g 51

<210> SEQ ID NO 8
<211> LENGTH: 10
<212> TYPE: DNA
<213> ORGANISM: Newcastle disease virus

<400> SEQUENCE: 8
acgggtagaa 10

<210> SEQ ID NO 9
<211> LENGTH: 12
<212> TYPE: DNA
<213> ORGANISM: Newcastle disease virus

<400> SEQUENCE: 9
attaagaaaa aa 12

<210> SEQ ID NO 10
<211> LENGTH: 6
<212> TYPE: PRT
<213> ORGANISM: Newcastle disease virus

<400> SEQUENCE: 10

Gly Arg Gln Gly Arg Leu
1 5

<210> SEQ ID NO 11
<211> LENGTH: 6
<212> TYPE: PRT
<213> ORGANISM: Newcastle disease virus

<400> SEQUENCE: 11

Arg Arg Gln Lys Arg Phe
1 5

<210> SEQ ID NO 12
<211> LENGTH: 882
<212> TYPE: PRT
<213> ORGANISM: infectious laryngotracheitis virus

<400> SEQUENCE: 12

Met Gln Ser Tyr Ile Ala Val Asn Ile Asp Met Ala Ser Leu Lys Met
1 5 10 15

Leu Ile Cys Val Cys Val Ala Ile Leu Ile Pro Ser Thr Leu Ser Gln
20 25 30

Asp Ser His Gly Ile Ala Gly Ile Ile Asp Pro Arg Asp Thr Ala Ser
35 40 45

Met Asp Val Gly Lys Ile Ser Phe Ser Glu Ala Ile Gly Ser Gly Ala
50 55 60

Pro Lys Glu Pro Gln Ile Arg Asn Arg Ile Phe Ala Cys Ser Ser Pro
65 70 75 80

Thr Gly Ala Ser Val Ala Arg Leu Ala Gln Pro Arg His Cys His Arg

-continued

```
                85                  90                  95

His Ala Asp Ser Thr Asn Met Thr Glu Gly Ile Ala Val Val Phe Lys
            100                 105                 110

Gln Asn Ile Ala Pro Tyr Val Phe Asn Val Thr Leu Tyr Tyr Lys His
        115                 120                 125

Ile Thr Thr Val Thr Thr Trp Ala Leu Phe Ser Arg Pro Gln Ile Thr
    130                 135                 140

Asn Glu Tyr Val Thr Arg Val Pro Ile Asp Tyr His Glu Ile Val Arg
145                 150                 155                 160

Ile Asp Arg Ser Gly Glu Cys Ser Ser Lys Ala Thr Tyr His Lys Asn
                165                 170                 175

Phe Met Phe Phe Glu Ala Tyr Asp Asn Asp Glu Ala Glu Lys Lys Leu
            180                 185                 190

Pro Leu Val Pro Ser Leu Leu Arg Ser Thr Val Ser Lys Ala Phe His
        195                 200                 205

Thr Thr Asn Phe Thr Lys Arg His Gln Thr Leu Gly Tyr Arg Thr Ser
    210                 215                 220

Thr Ser Val Asp Cys Val Val Glu Tyr Leu Gln Ala Arg Ser Val Tyr
225                 230                 235                 240

Pro Tyr Asp Tyr Phe Gly Met Ala Thr Gly Asp Thr Val Glu Ile Ser
                245                 250                 255

Pro Phe Tyr Thr Lys Asn Thr Thr Gly Pro Arg Arg His Ser Val Tyr
            260                 265                 270

Arg Asp Tyr Arg Phe Leu Glu Ile Ala Asn Tyr Gln Val Arg Asp Leu
        275                 280                 285

Glu Thr Gly Gln Ile Arg Pro Pro Lys Lys Arg Asn Phe Leu Thr Asp
    290                 295                 300

Glu Gln Phe Thr Ile Gly Trp Asp Ala Met Glu Glu Lys Glu Ser Val
305                 310                 315                 320

Cys Thr Leu Ser Lys Trp Ile Glu Val Pro Glu Ala Val Arg Val Ser
                325                 330                 335

Tyr Lys Asn Ser Tyr His Phe Ser Leu Lys Asp Met Thr Met Thr Phe
            340                 345                 350

Ser Ser Gly Lys Gln Pro Phe Asn Ile Ser Arg Leu His Leu Ala Glu
        355                 360                 365

Cys Val Pro Thr Ile Ala Ser Glu Ala Ile Asp Gly Ile Phe Ala Arg
    370                 375                 380

Lys Tyr Ser Ser Thr His Val Arg Ser Gly Asp Ile Glu Tyr Tyr Leu
385                 390                 395                 400

Gly Ser Gly Gly Phe Leu Ile Ala Phe Gln Lys Leu Met Ser His Gly
                405                 410                 415

Leu Ala Glu Met Tyr Leu Glu Glu Ala Gln Arg Gln Asn His Leu Pro
            420                 425                 430

Arg Gly Arg Glu Arg Arg Gln Ala Ala Gly Arg Arg Thr Ala Ser Leu
        435                 440                 445

Gln Ser Gly Pro Gln Gly Asp Arg Ile Thr Thr His Ser Ser Ala Thr
    450                 455                 460

Phe Ala Met Leu Gln Phe Ala Tyr Asp Lys Ile Gln Ala His Val Asn
465                 470                 475                 480

Glu Leu Ile Gly Asn Leu Leu Glu Ala Trp Cys Glu Leu Gln Asn Arg
                485                 490                 495

Gln Leu Ile Val Trp His Glu Met Lys Lys Leu Asn Pro Asn Ser Leu
            500                 505                 510
```

-continued

```
Met Thr Ser Leu Phe Gly Gln Pro Val Ser Ala Arg Leu Leu Gly Asp
        515                 520                 525

Ile Val Ala Val Ser Lys Cys Ile Glu Ile Pro Ile Glu Asn Ile Arg
    530                 535                 540

Met Gln Asp Ser Met Arg Met Pro Gly Asp Pro Thr Met Cys Tyr Thr
545                 550                 555                 560

Arg Pro Val Leu Ile Phe Arg Tyr Ser Ser Ser Pro Glu Ser Gln Phe
                565                 570                 575

Ser Ala Asn Ser Thr Glu Asn His Asn Leu Asp Ile Leu Gly Gln Leu
            580                 585                 590

Gly Glu His Asn Glu Ile Leu Gln Gly Arg Asn Leu Ile Glu Pro Cys
        595                 600                 605

Met Ile Asn His Arg Arg Tyr Phe Leu Leu Gly Glu Asn Tyr Leu Leu
    610                 615                 620

Tyr Glu Asp Tyr Thr Phe Val Arg Gln Val Asn Ala Ser Glu Ile Glu
625                 630                 635                 640

Glu Val Ser Thr Phe Ile Asn Leu Asn Ala Thr Ile Leu Glu Asp Leu
                645                 650                 655

Asp Phe Val Pro Val Glu Val Tyr Thr Arg Glu Glu Leu Arg Asp Thr
            660                 665                 670

Gly Thr Leu Asn Tyr Asp Asp Val Val Arg Tyr Gln Asn Ile Tyr Asn
        675                 680                 685

Lys Arg Phe Arg Asp Ile Asp Thr Val Ile Arg Gly Asp Arg Gly Asp
    690                 695                 700

Ala Ile Phe Arg Ala Ile Ala Asp Phe Phe Gly Asn Thr Leu Gly Glu
705                 710                 715                 720

Val Gly Lys Ala Leu Gly Thr Val Val Met Thr Ala Ala Ala Ala Val
                725                 730                 735

Ile Ser Thr Val Ser Gly Ile Ala Ser Phe Leu Ser Asn Pro Phe Ala
            740                 745                 750

Ala Leu Gly Ile Gly Ile Ala Val Val Val Ser Ile Ile Leu Gly Leu
        755                 760                 765

Leu Ala Phe Lys Tyr Val Met Asn Leu Lys Ser Asn Pro Val Gln Val
    770                 775                 780

Leu Phe Pro Gly Ala Val Pro Pro Ala Gly Thr Pro Pro Arg Pro Ser
785                 790                 795                 800

Arg Arg Tyr Tyr Lys Asp Glu Glu Val Glu Glu Asp Ser Asp Glu Asp
                805                 810                 815

Asp Arg Ile Leu Ala Thr Arg Val Leu Lys Gly Leu Glu Leu Leu His
            820                 825                 830

Lys Asp Glu Gln Lys Ala Arg Arg Gln Lys Ala Arg Phe Ser Ala Phe
        835                 840                 845

Ala Lys Asn Met Arg Asn Leu Phe Arg Arg Lys Pro Arg Thr Lys Glu
    850                 855                 860

Asp Asp Tyr Pro Leu Leu Glu Tyr Pro Ser Trp Ala Glu Glu Ser Glu
865                 870                 875                 880

Asp Glu


<210> SEQ ID NO 13
<211> LENGTH: 2649
<212> TYPE: DNA
<213> ORGANISM: infectious laryngotracheitis virus

<400> SEQUENCE: 13
```

```
atgcaatcct acatcgccgt gaacattgac atggctagct tgaaaatgct gatctgcgtg     60
tgcgtggcaa tcctgatccc atctacccta tctcaagatt cacacggaat tgctggaata    120
atagaccctc gtgatacagc cagcatggat gttggaaaaa tctctttctc cgaagccatt    180
gggtcggggg caccgaaaga accccagatt agaaacagaa tttttgcgtg ctcatctcca    240
actggcgcca gtgttgcgag gcttgcccag ccacgacatt gtcaccgaca tgccgattcg    300
actaacatga ctgaaggaat tgccgtagtc ttcaagcaaa acattgcccc gtacgtcttt    360
aatgtgactc tatactataa acatataacc acagttacta cgtgggcatt attctcaaga    420
ccccaaataa caaatgagta cgtgaccagg gttccaatag actatcatga aattgtcagg    480
attgatcgat cgggagaatg ctcatccaaa gcaacgtatc ataaaaattt catgtttttt    540
gaagcttacg acaatgatga agcagaaaaa aaattgcccc tggttccatc actgttaaga    600
tcaactgtct ccaaggcgtt tcatacaact aactttacta agcgacatca aaccctggga    660
taccgaacgt ctacatcggt cgactgtgtt gtggaatatc tacaggctag atctgtatac    720
ccgtatgatt actttggaat ggcgacaggt gatacagtag aaatttctcc tttttatacc    780
aaaaacacga ccggaccaag gcgtcacagt gtctacagag actatagatt tctcgaaatc    840
gcaaattatc aagtcaggga tttggaaacc ggacaaataa gacccccctaa aaaaagaaac    900
tttctaacag atgaacaatt cactataggc tgggatgcaa tggaagaaaa ggaatctgta    960
tgtactctca gtaaatggat tgaagtcccg gaagcagttc gtgtttcgta caaaaacagt   1020
taccactttt cacttaaaga tatgactatg acgttctcgt ccggaaaaca accttttaac   1080
atcagcaggc ttcatttggc tgaatgcgtt cctaccatag cctcggaggc catagatggc   1140
atctttgcca gaaagtatag ttcgactcat gtccgttctg ggacatcgga atactatctc   1200
ggtagtggcg gatttctgat cgcatttcag aaactcatga gccatggctt ggctgaaatg   1260
tacctagaag aggcacaaag acaaaatcat ctcccgagag ggagagagcg tcgccaagcc   1320
gcaggtcgcc gcacggcgtc gctgcagtct ggacctcagg gtgatagaat tactacccac   1380
agttctgcaa catttgccat gttacaattt gcatacgaca aaatccaagc ccatgttaac   1440
gagcttatcg gaaatttgtt ggaagcgtgg tgtgagcttc agaaccgcca actgattgta   1500
tggcatgaga tgaagaaact aaacccgaac tcactgatga catctttgtt cggacaacct   1560
gtaagcgcca ggctattggg agacatcgta gcggtatcaa aatgtataga aattccaatc   1620
gaaaatatta ggatgcagga ttccatgcgc atgccagggg acccaaccat gtgctatacc   1680
agaccagtac ttattttcag gtattcgtcc tcccctgagt cacagttttc tgcgaactca   1740
acagaaaacc acaatcttga catattaggc caactcggag aacataatga aattttacaa   1800
gggcggaatt tgatagaacc atgcatgatc aatcacagac ggtactttct gttgggagaa   1860
aactaccttc tttacgaaga ctatacattt gttagacaag taaatgcttc cgagatcgaa   1920
gaagtgagca cattcatcaa cttgaacgcc actatactag aagatttgga ctttgtgccc   1980
gtcgaagtat acactcgcga ggaactcaga gatactggga ctttaaacta tgatgatgtg   2040
gtcagatatc aaaatattta taacaaaagg ttcagagaca ttgacactgt aatacgtgga   2100
gataggggag atgcaatctt tagagcaata gcagattttt ttggcaacac tcttggagaa   2160
gtaggaaagg cattgggaac tgtagtgatg acagccgcgg cagcagtaat ttctacagta   2220
tctggcatcg cctcatttct ttctaacccg ttcgccgcac tcggaattgg gatagcggtg   2280
gtggtgagca ttattttagg actgctggcg ttcaaatatg taatgaacct gaaatcaaac   2340
```

-continued

```
ccagttcagg ttctgttccc aggcgcagtt cccccggccg gaactcctcc acgaccctct   2400

agacgttact acaaggatga ggaggttgag gaggatagtg atgaggacga caggatactt   2460

gccaccagag ttctgaaagg ccttgagctt ctacacaagg atgaacagaa agctcgaaga   2520

cagaaagcgc ggttttctgc ttttgctaaa aatatgagaa acctatttcg cagaaaaccc   2580

cgaaccaagg aagatgacta ccccctgctc gaatacccttt cgtgggcaga agaaagcgaa   2640

gacgaataa                                                           2649


<210> SEQ ID NO 14
<211> LENGTH: 434
<212> TYPE: PRT
<213> ORGANISM: infectious laryngotracheitis virus

<400> SEQUENCE: 14

Met His Arg Pro His Leu Arg Arg His Ser Arg Tyr Tyr Ala Lys Gly
1               5                   10                  15

Glu Val Leu Asn Lys His Met Asp Cys Gly Gly Lys Arg Cys Cys Ser
            20                  25                  30

Gly Ala Ala Val Phe Thr Leu Phe Trp Thr Cys Val Arg Ile Met Arg
        35                  40                  45

Glu His Ile Cys Phe Val Arg Asn Ala Met Asp Arg His Leu Phe Leu
    50                  55                  60

Arg Asn Ala Phe Trp Thr Ile Val Leu Leu Ser Ser Phe Ala Ser Gln
65                  70                  75                  80

Ser Thr Ala Ala Val Thr Tyr Asp Tyr Ile Leu Gly Arg Arg Ala Leu
                85                  90                  95

Asp Ala Leu Thr Ile Pro Ala Val Gly Pro Tyr Asn Arg Tyr Leu Thr
            100                 105                 110

Arg Val Ser Arg Gly Cys Asp Val Val Glu Leu Asn Pro Ile Ser Asn
        115                 120                 125

Val Asp Asp Met Ile Ser Ala Ala Lys Glu Lys Glu Lys Gly Gly Pro
    130                 135                 140

Phe Glu Ala Ser Val Val Trp Phe Tyr Val Ile Lys Gly Asp Asp Gly
145                 150                 155                 160

Glu Asp Lys Tyr Cys Pro Ile Tyr Arg Lys Glu Tyr Arg Glu Cys Gly
                165                 170                 175

Asp Val Gln Leu Leu Ser Glu Cys Ala Val Gln Ser Ala Gln Met Trp
            180                 185                 190

Ala Val Asp Tyr Val Pro Ser Thr Leu Val Ser Arg Asn Gly Ala Gly
        195                 200                 205

Leu Thr Ile Phe Ser Pro Thr Ala Ala Leu Ser Gly Gln Tyr Leu Leu
    210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
                245                 250                 255

Ser Lys Cys Trp Thr Thr Glu Gln Tyr Gln Thr Gly Phe Gln Gly Glu
            260                 265                 270

His Leu Tyr Pro Ile Ala Asp Thr Asn Thr Arg His Ala Asp Asp Val
        275                 280                 285

Tyr Arg Gly Tyr Glu Asp Ile Leu Gln Arg Trp Asn Asn Leu Leu Arg
    290                 295                 300

Lys Lys Asn Pro Ser Ala Pro Asp Pro Arg Pro Asp Ser Val Pro Gln
305                 310                 315                 320
```

-continued

```
Glu Ile Pro Ala Val Thr Lys Lys Ala Glu Gly Arg Thr Pro Asp Ala
                325                 330                 335

Glu Ser Ser Glu Lys Lys Ala Pro Pro Glu Asp Ser Glu Asp Asp Met
            340                 345                 350

Gln Ala Glu Ala Ser Gly Glu Asn Pro Ala Ala Leu Pro Glu Asp Asp
        355                 360                 365

Glu Val Pro Glu Asp Thr Glu His Asp Asp Pro Asn Ser Asp Pro Asp
    370                 375                 380

Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
                405                 410                 415

Ala Val Ala Leu Val Gly Leu Leu Val Trp Ser Ile Val Lys Cys Ala
            420                 425                 430

Arg Ser

<210> SEQ ID NO 15
<211> LENGTH: 1305
<212> TYPE: DNA
<213> ORGANISM: infectious laryngotracheitis virus

<400> SEQUENCE: 15
atgcaccgtc ctcatctcag acggcactcg cgttactacg cgaaaggaga ggtgcttaac      60
aaacacatgg attgcggtgg aaaacggtgc tgctcaggcg cagctgtatt cactcttttc     120
tggacttgtg tcaggattat gcgggagcat atctgctttg tacgcaacgc tatggaccgc     180
catttatttt tgaggaatgc tttttggact atcgtactgc tttcttcctt cgctagccag     240
agcaccgccg ccgtcacgta cgactacatt ttaggccgtc gcgcgctcga cgcgctaacc     300
ataccggcgg ttggcccgta taacagatac ctcactaggg tatcaagagg ctgcgacgtt     360
gtcgagctca acccgatttc taacgtggac gacatgatat cggcggccaa agaaaaagag     420
aaggggggcc ctttcgaggc ctccgtcgtc tggttctacg tgattaaggg cgacgacggc     480
gaggacaagt actgtccaat ctatagaaaa gagtacaggg aatgtggcga cgtacaactg     540
ctatctgaat gcgccgttca atctgcacag atgtgggcag tggactatgt tcctagcacc     600
cttgtatcgc gaaatggcgc gggactgact atattctccc ccactgctgc gctctctggc     660
caatacttgc tgaccctgaa aatcgggaga tttgcgcaaa cagctctcgt aactctagaa     720
gttaacgatc gctgtttaaa gatcgggtcg cagcttaact ttttaccgtc gaaatgctgg     780
acaacagaac agtatcagac tggatttcaa ggcgaacacc tttatccgat cgcagacacc     840
aatacacgac acgcggacga cgtatatcgg ggatacgaag atattctgca gcgctggaat     900
aatttgctga ggaaaaagaa tcctagcgcg ccagaccctc gtccagatag cgtcccgcaa     960
gaaattcccg ctgtaaccaa gaaagcggaa gggcgcaccc cggacgcaga aagcagcgaa    1020
aagaaggccc ctccagaaga ctcggaggac gacatgcagg cagaggcttc tggagaaaat    1080
cctgccgccc tccccgaaga cgacgaagtc cccgaggaca ccgagcacga tgatccaaac    1140
tcggatcctg actattacaa tgatatgccc gccgtgatcc cggtggagga gactactaaa    1200
agttctaatg ccgtctccat gcccatattc gcggcgttcg tagcctgcgc ggtcgcgctc    1260
gtggggctac tggtttggag catcgtaaaa tgcgcgcgta gctaa                    1305

<210> SEQ ID NO 16
<211> LENGTH: 17877
```

-continued

<212> TYPE: DNA
<213> ORGANISM: Artificial Sequence
<220> FEATURE:
<223> OTHER INFORMATION: chemically synthesized

<400> SEQUENCE: 16

```
gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg ccagagaatc    240

tgtgaggtac gataaaaggc gaagaagcaa tcgagatcgt acggtagaag gtgtgaaccc    300

cgagcgcgag gccgaagctc gaacctgagg gaaccttcta ccgatatgtc gtctgtttcg    360

acgaatacga gcagctcctt gctgctcaga cccgccctaa cggaactcat ggagggggag    420

agaaagggag cactttaaaa gttgaggtcc cagtatttac cctaaacagt gatgatccgg    480

aagatagatg gaattttgcg gtattctgtc ttcggattgc tgttagcgag gatgccaaca    540

aaccactcag gcaaggtgct cttatatccc tcttatgctc ccattctcag gtgatgagaa    600

accatgttgc ccttgcaggg aaacagaatg aggccacact ggctgttctt gagatcgatg    660

gttttgctaa cagtgtgccc cagttcaaca ataggagtgg agtgtctgag gagagagcac    720

agagattcat ggtaatcgca ggatctctcc ctcgggcatg cagcaacggt actccgtttg    780

tcacggctgg ggttgaagat gatgcaccag aagatatcac tgacactctg gaaagaatcc    840

tatctatcca agttcaggta tgggtcacag tagcaaaggc catgactgca tatgagacag    900

cagatgagtc agaaacaaga agaataaata agtatatgca gcaaggtcga gttcagaaaa    960

agtacatcct tcatcctgta tgcaggagtg caattcaact cacaatcaga cattctctgg   1020

cagtccgtat tttcctagtt agtgagctca agaggggccg caatacagca ggtgggagct   1080

ctacatatta caacttggtc ggggatgtag actcatacat caggaacacc gggcttactg   1140

catttttcct aacactcaaa tatggaatca ataccaagac gtcagccctc gcactcagca   1200

gcctcacagg tgatatccaa aaaatgaaac agctcatgcg tttatatcgg atgaaaggtg   1260

aaaatgcacc atacatgaca ttgttaggcg acagtgacca gatgagcttt gcaccagctg   1320

agtatgcaca actttattct tttgccatgg gcatggcatc agtcttagat aagggaactg   1380

gcaagtacca attcgccagg gactttatga gcacatcatt ctggagactt ggagtagagt   1440

atgctcaggc ccagggaagt agcattaatg aggacatggc tgctgagcta aaactaaccc   1500

tggcagcaag gagaggcctg gcagctgctg cccaacgagt atccgaagaa atcggcagca   1560

tggacattcc cactcaacag gcgggagtcc tcaccgggct cagtgacgaa ggcccccgaa   1620

ctccacaggg cggatcaaac aagccgcaag ggcaaccaga tgccggggat ggggagaccc   1680

aattcttgga ttttatgaga gcagtggcga acagcatgcg ggaagcgcca aatcctgcac   1740

agagcaccac ccatccagag cctcccccaa cccctggggc atcccaagac aacgacactg   1800

actgggggta ctgatcgaca acacccagcc cgccttcaca ggaccacacc aaaccccccg   1860

cccaaaactc tcccacactc cccgacccac aaccccgcac gaccacacca acaaaagctc   1920

cccccccccc tctcccccac ccccagccac acgatcccac ccacccggga caacacaggc   1980

acagctcggc tcgtcgacaa cccgcccaga gcccaaggta ttagaaaaaa atacgggtag   2040

aagagagaca tccagagacc aagacgagtc accaagttct ctgttctccc ttctacccag   2100

tggattaggg tgaagatggc cacttttaca gatgcggaga tagatgacat atttgagacc   2160
```

-continued agtgggactg tcattgacag cataattacg gcccaggaca aatcagctga gaccgttgaa 2220
agaagcgcga tcccgcaggg caagaccaaa gctctaagca cagcatggga gaagcacggg 2280
agtgtccagc cacacgccag tcaggacgcc cctgaccaac aagacagaac agaaaaacag 2340
ccatccacac ctgagcaggt gactctacac aacaacccgc cgatcacatc cactggaccg 2400
cctcccactc aggccgcaag cgagaccagc gacacacagc tcaagactgg agcaagcaac 2460
tcccttctgt ccatgctcga caaactgagc aataaatcgt ccaatgctaa aaagggccca 2520
tggtcgggtt cccaagaagg gcatcaccaa cctccggccc aacaacacgg ggaccagccg 2580
agctatggaa gcaaccaggg aagaccgcag catcaggcca aggccgtccc tggaaaccgg 2640
ggcacagacg agaacacagc atatcatgga caacggaagg agtcacaact atcagctggt 2700
gcaacccctc atgcgcccca gtcagggcag agccaagaca atactcctgt acctgtggat 2760
cgtgtccagc tatctgccga ctttgcgcag gcgatgatgt ctatgatgga ggcattatca 2820
cagaaggtaa gtaaagttga tcatcagctg gacctagtct tgaaacagac atcctccatt 2880
cctatgatgc gatctgaaat ccaacagctc aagacatctg ttgcgatcat ggaagctaac 2940
ttaggcatga tgaaaattct ggaccctggt tgtgctaacg tttcatcctt aagtgatctc 3000
cgggcagtag cccgatccca cccagtccta gtttcaggcc ccggagaccc atctccttac 3060
gtgacacaag gggtgaaat gacgctcaat aaactctcac aaccggtgca gcacccctct 3120
gaattgatta agtctgccac tgcaagcggg cctgacatgg gagtggagaa ggacactgtc 3180
cgcgcattaa tcacctcgcg cccgatgcat ccgagctcct cggctaagct cctgagcaag 3240
ctagatgcag ccaggtcaat tgaagagatc aggaagatca aacgccttgc gctgaatggt 3300
tgatggccat cacaactcat aacaggctcc cgtcacttta gcgtcacacg gaatccctcg 3360
ggggccctcg ttggtacttc tacccgtatt ttttctaaga gggccccccc tcgcaaatcc 3420
acgcttcaac acccaaaaca acagccctct ctcacccccc tcaatccccc gaatgatcgc 3480
acaactgcaa ccaatccagc tgcattagaa attaagaaaa aatacgggta gaatcagagt 3540
gccttgattg caccaaaatg gactcatcca ggacaatcgg gctgtacttt gattctgccc 3600
tcccttccag cagcctgtta gcatttccga ttgtcttaca agacacagga gacgggaaga 3660
agcaaatcac cccacaatac aggatccagc gccttgattc gtggacagac agtaaggaag 3720
actcggtatt catcaccacc tacgggttca tctttcaaat tgggaatgaa gaagccactg 3780
tcggtgtgat caatgacaat cccaagcacg agctactctc ttccgcaatg ctctgcttag 3840
ggagtgtccc gaacgacgga gatcttgttg agctggcaag agcctgcctc accatggtgg 3900
taacttgcaa gaagagtgca actaacactg agagaatagt cttctcagta gtgcaggcac 3960
ctcgggtgct gcaaagctgt atggttgtgg caaataggta ctcatcagtg aatgcagtga 4020
agcatgtgaa ggcgccagaa aagatccctg ggagcggaac cctagagtat aaagtgaatt 4080
ttgtctcttt gaccgtggtg ccaagaaggg atgtctacag gatcccaact gcagtattga 4140
aagtgtctgg ctcaagcctg tacaatcttg cgctcaatgt cactattgat gtggacgtgg 4200
atccgaagag cccgttagtc aaatcccttt ctaagtccga tagcggatac tatgcgaatc 4260
tttttctgca tatcgggctt atgtccactg tagataagaa ggggaagaaa gtgacatttg 4320
acaagataga ggaaaagata aggagactca atctatccgt cgggctcagt gatgtgctcg 4380
gaccctctgt gcttgtgaag gcgagaggtg cacggactaa gttacttgct cctttcttct 4440
ctagcagtgg gacagcctgc tatcctatag caaatgcctc tccccaggtt gccaagatac 4500
tctggagcca aactgcgcac ctgcggagtg tgaaagtcat cattcaagcc ggcactcagc 4560

-continued

```
gtgctgtcgc agtgaccgct gatcatgagg taacctccac taagatagag aggaggcatg   4620
ccattgctaa atacaatcct ttcaggaaat aagttgcatc cctaagactg cagttcacct   4680
gctttctcga atcaccatta caccagacaa tgatccatct cgactgctta tagttagttc   4740
acctgtctag caaattagaa aaaacacggg tagaagagtc tggatcccga ccggcacatt   4800
caggacgcaa tatgggctcc aaactttcta ccaggatccc agcacctctg atgctgatca   4860
cccggattat gctgatattg ggctgtatcc gtccgaccag ctctcttgac ggcaggcctc   4920
ttgcagctgc aggaattgta gtaacaggag ataaggcagt caatgtatac acctcgtctc   4980
agacagggtc aatcatagtc aagttgctcc cgaatatgcc cagggataag gaggcgtgtg   5040
cgaaagcccc attagaggca tataacagaa cactgactac tttgctcact cctcttggcg   5100
actccatccg caagatccaa gggtctgtgt ccacgtctgg aggagggaga caagggcgcc   5160
ttataggtgc tgttattggc agtgtagctc ttggggttgc aacagcggca cagataacag   5220
cagctgcggc cctaatacaa gccaaccgga atgccgccaa catcctccgg cttaaggaga   5280
gcattgctgc aaccaatgaa gctgtgcatg aagtcaccga cggattatcg caactatcag   5340
tggcagttgg gaagatgcag cagtttgtca atgaccagtt taataatacg gcgcgagaat   5400
tggactgtat aaaaatcaca caacaggttg gtgtagaact caacctatac ctgactgaat   5460
tgactacagt attcgggcca cagatcacct cccctgcatt aactcagctg accatccagg   5520
cactttataa tttagctggt ggcaatatgg attacttatt aactaggtta ggtataggga   5580
acaatcaact cagctcattg attggtagcg gcctgatcac tggttaccct atactgtatg   5640
actcacagac tcaactcttg ggcatacaag tgaatttgcc ctcagtcggg aacttaaata   5700
atatgcgtgc cacctatttg gagaccttat ctgtaagtac aaccaaagga tatgcctcag   5760
cacttgtccc gaaagtagta acacaagtcg gttctgtgat agaagagctt gacacctcat   5820
actgtataga gtccgatctg gatttatatt gtactagaat agtgacactc cccatgtccc   5880
caggtattta ttcctgtttg agcggcaaca catcagcttg catgtactca aagactgaag   5940
gcgcactcac tacgccgtat atggccctta aaggctcagt tattgccaat tgtaagataa   6000
caacatgtag atgtacagac cctcctggta tcatatcgca aaattatgga gaagctgtat   6060
ccctgataga tagacatttg tgcaatgtct tatcattaga cgggataact ctgaggctca   6120
gtggggaatt tgatgcaact tatcaaaaga acatctcaat actagattct caagtcatcg   6180
tgacaggcaa tcttgatata tcaactgaac ttggaaacgt caacaattca atcagcaatg   6240
ccttggatag gttggcagaa agcaacagca agctagaaaa agtcaatgtc agactaacca   6300
gcacatctgc tctcattacc tatattgttc taactgtcat ttctctagtt ttcggtgcac   6360
ttagtctggg tttagcgtgt tacctgatgt acaaacagaa ggcacaacaa aagaccttgc   6420
tatggcttgg gaataatacc ctcgatcaga tgagagccac tacaagagca tgaatgcaga   6480
taagaggtgg atatataccc aacagcagcc tgtgtgtcaa ttccgataac ctgtcaagta   6540
gaagacttaa gaaaaaacta ctgggaacaa gcaaccaaag agcaatacac gggtagaacg   6600
gtcagaggag ccacccttca atcgggaatt aggcttcaca acatccgttc tatcacatca   6660
ccgacaacaa gagtcaatca tggaccgcgc ggttaacaga gtcgtgctgg agaatgagga   6720
aagagaagca aagaacacat ggcgcctggt tttccggatc gcagtcttac ttttaatggt   6780
aatgactcta gctatctccg cagctgccct ggcatacagt acgggggcca gtacgccgca   6840
cgacctcgca ggcatatcga ctgtgatctc caagacagaa gataaggtta catctttact   6900
```

-continued

```
cagtttgagt caagatgtga tagataagat atacaagcag gtggctcttg aatccccgct   6960
ggcgctacta aacactgaat ctataattat gaatgcaata acctttcttt cttatcaaat   7020
taacggggct gcgaacaata gcggatgtgg ggcgcctgtt catgacccag attatatcgg   7080
ggggataggc aaagaactca tagtggacga catcagtgat gtcacatcat tttatccttc   7140
tgcatatcaa gaacacttga atttcatccc ggcgcctact acaggatccg gttgcactcg   7200
gataccctca tttgacatga gcaccaccca ttattgttat actcacaatg tgatactatc   7260
cggttgcaga gatcactcac actcacatca atacttagca cttggtgtgc ttcggacatc   7320
tgcaacaggg agggtattct tttctactct gcgctccatc aatttagatg acacccaaaa   7380
tcggaagtcc tgcagtgtga gtgcaacccc tttaggttgt gatatgctgt gctctaaggt   7440
cacagagact gaagaggagg attacaagtc agttgccccc acatcaatgg tgcacggaag   7500
gctagggttt gacggtcaat accatgagaa ggacttagac accacggtct tatttaagga   7560
ttgggtggca aattacccag gggcgggagg agggtctttt attgacgacc gtgtatggtt   7620
cccagtttac ggagggctca aacccaattc acccagtgac actgcacaag aagggaaata   7680
tgtaatatac aagcgccata acaacacatg ccctgatgaa caagattacc aaattcggat   7740
ggctaagtct tcatataaac ccgggcgatt tggtggaaag cgcgtacagc aagccatctt   7800
atccatcaaa gtgtcaacat ccttgggtaa ggacccggtg ctgactattc cacctaatac   7860
aatcacactc atgggagccg aaggcagaat cctcacagta gggacatctc acttcttgta   7920
ccaacgaggg tcttcatatt tctcccctgc cttattatat cccatgacag taaataacaa   7980
aacggctaca ctccatagtc cttatacgtt taatgctttc actcggccag gtagtgtccc   8040
ttgccaggca tcagcaagat gccccaactc atgcatcact ggggtctata ctgatccata   8100
tcccttaatc ttccatagga atcatactct acgaggggtc ttcgggacga tgcttgatga   8160
tgaacaagcg agacttaacc ccgtatctgc agtattcgac aacatatctc gcagtcgtgt   8220
cacccgggtg agttcaagca gcaccaaggc agcatacacg acatcgacat gttttaaagt   8280
tgtcaagacc aataaaactt attgtcttag tattgcagaa atatccaata ccctattcgg   8340
ggaatttagg atcgttccct tattagttga gatcctcaag gatgatagag tttaagaagc   8400
tagacttggc cgattgagcc aatcatagga tggttgggaa gacgacacca caccaatcat   8460
ctcccacaat gcttagagtc aagctgaata ttaacataag ccaggatccc atgttgttgg   8520
gcagccacaa ccagacaatg ctgacatgat tattctgagt cccgcccact atcactttat   8580
taagaaaaaa tacagaaagc attgagatgt aagggaaaac aaccaacaag agggaacacg   8640
ggtaggacat ggcgggctcc ggtcccgaaa gggcagagca ccagatcatc ctaccagagt   8700
cacatctatc ctctccattg gtcaagcaca aattgctata ctactggaaa ttgactgggc   8760
taccgcttcc tgatgaatgc gactttgacc atctcattat cagcaggcaa tggaagagaa   8820
tactggagtc ggccactcct gacacagaga gaatgataaa actcgggcgg gcagtgcacc   8880
agactctcaa ccacaattcc aagataaccg gagtgctcca tcccaggtgt ttagaagaac   8940
tggctagtat tgaggtccca gattcaacta acaaattccg gaagattgaa aagaagatcc   9000
agattcacaa cacaaggtat ggagacctgt tcacaaagct gtgcacgcat gttgagaaga   9060
aattgctagg atcgtcccgg tctaataatg tcccacgatc agaggaattc agtagtatcc   9120
gtacagatcc ggcattctgg tttcactcaa aatggtccag agccaagttc gcgtggctcc   9180
atataaaaca agtccaaagg catctgattg tagcagcaag gacaaggtct gcagtcaaca   9240
agttagtaac attaagtcat aagataggcc acgtctttgt ttctcctgag cttgtcattg   9300
```

-continued

```
tgacacatac agatgagaac aagttcacat gcctcaccca ggaacttgta ttgatgtatg   9360
cggatatgat ggaaggcagg gacatggtca atataatatc ttctacagca gcacatctca   9420
gaaacctatc cgagaaaatt gacgatattc tgcgattagt agatgccctg gcaaaggact   9480
taggtaatca agtctatgac gttgtagcat taatggaggg attcgcatac ggtgccgttc   9540
agctgcttga gccatcaggt acatttgcag gagatttctt tgcatttaac ctacaggagc   9600
tcaaagacac tttaatcgaa cttctcccaa ataatatagc ggaatcagta actcacgcta   9660
ttgccactgt attctccggc ttagaacaga atcaagcagc tgagatgttg tgcttgctac   9720
gtttgtgggg tcatccattg cttgagtctc gtagtgcagc aagagcagtc aggagccaga   9780
tgtgcgcacc aaagatggta gatttcgata tgatcctcca agtattatct ttctttaaag   9840
gaacaatcat caatggatac agaaagaaga actcaggtgt gtggccgcgt gtcaaagtag   9900
atacaatata cgggaatatc attgggcagc tacatgctga ttcagcagag atctcacatg   9960
atgtcatgtt gagggagtac aagagtttat ctgctcttga atttgagcca tgtatagatt  10020
atgaccctgt taccaatcta agcatgttcc taaaagacaa ggcaatcgca catcctagtg  10080
ataattggct cgcctcattt aggcggaacc tactctctga ggaccagaag aaacagataa  10140
aagaggcaac ttcaactaac cgcctcctga tagagttctt agaatcaaat gattttgatc  10200
catataaaga aatggaatac ctgacaaccc tcgagtacct aagagatgac agtgtggcgg  10260
tatcgtactc actcaaagag aaagaggtga aagtgaatgg gcggatcttt gctaagttaa  10320
caaagaaact aaggaactgc caggtaatgg cagaaggaat tctagctgac cagattgcac  10380
ctttctttca gggaaatggg gtcattcaag atagcatatc cttgacaaag agtatgttag  10440
cgatgagtca actgtccttt aacagcaata agaaacgtat cactgactgc aaagagaggg  10500
tttcctcgaa ccgcaatcat gatcagaaga gcaagaatcg tagaagagtt gccactttta  10560
tcacgactga cctacaaaag tattgtctta actggagata tcagacagtc aaactattcg  10620
ctcatgctat caatcagctg atgggcctac ctcatttctt tgagtggatt catcttaggc  10680
tgatggacac tacaatgttt gtaggggatc ctttcaatcc tccaagtgac ccgactgact  10740
gtgatctatc aagagtccca aatgatgaca tatatattgt cagtgctaga gggggcattg  10800
agggactctg ccagaagcta tggacgatga tctcaattgc tgcaatccaa cttgctgcag  10860
caagatctca ttgtcgagtt gcctgcatgg tacaaggtga caatcaagta atagctgtaa  10920
cgagagaggt aagatcagat gattccccgg atatggtgtt gacgcagttg catcaagcta  10980
gtgataattt cttcaaggaa ttaattcatg tcaatcattt gattggccat aacctgaagg  11040
atcgtgaaac cattagatcc gacacattct tcatatacag caaacgaata ttcaaagatg  11100
gagcaatact cagtcaggtc ctcaaaaatt catctaaatt ggtgctaata tcaggcgacc  11160
ttagcgaaaa cactgtaatg tcctgtgcca acattgcatc cactgtcgca cgactatgtg  11220
agaatgggct tcctaaggat ttctgttact atttgaacta cctaatgagt tgcgtgcaga  11280
catactttga ttcggagttt tctattaccc acagctcgca atcagattcc aaccagtcct  11340
ggatcgagga tatctctttc gtacactcat acgtgttaac ccctgcccag ctgggggac  11400
tgagcaacct tcaatactca aggctctaca caaggaatat tggtgaccca gggaccactg  11460
ctttcgcaga ggtcaagcga ctagaagcag tggggttgct gagtcccagc atcatgacta  11520
acatcttaac caggccacct ggcaatggag actgggccag cctatgcaac gacccatact  11580
cttttaattt tgagactgtt gcaagcccaa atattgtcct caagaaacat acacagaaag  11640
```

-continued

```
tcctatttga gacatgttca aaccccttat tatccggggt acatacagag gacaatgagg  11700
cagaagagaa agcattggct gaattcttac tcaatcaaga agtgattcac ccgcgtgtcg  11760
cacatgctat catggaagca agttctgtgg gtaggagaaa gcaaattcaa gggcttgttg  11820
acacaacgaa cactgtgatt aagattgcac tgactaggag gcccctcggt atcaaaaggc  11880
tgatgcggat aatcaactac tcgagcatgc atgcaatgtt gttcagagat gatattttct  11940
tatccaatag atccaaccac ccattagttt cttctaatat gtgctcgctg acgctagcag  12000
attatgcccg gaacagaagc tggtcacccc tgacaggggg caggaaaata ctgggtgtat  12060
ccaaccctga taccatagaa cttgtggagg gagagattct cagcgtcagt ggagggtgca  12120
caaaatgtga cagcggagat gagcagttta cttggttcca tcttccaagc aatatagagc  12180
tgactgatga caccagcaaa aatcccccga tgagagtgcc atatctcggg tcgaagactc  12240
aagagaggag agctgcctcg cttgcgaaaa tagcccacat gtcaccacat gtgaaagcag  12300
cactaagggc atcatccgtg ttaatctggg cttatgggga caacgaagtg aactggactg  12360
ctgctcttaa tattgcaagg tctcgatgca acataagctc agagtatctt cggctattgt  12420
cacccctgcc cacagctggg aatctccaac atagattgga tgatggcata acccagatga  12480
catttacccc tgcatctctc tacagagtgt cgccttacgt tcacatatcc aatgattctc  12540
aaaggctatt caccgaagaa ggggtcaaag agggaaacgt ggtttaccaa caaattatgc  12600
tcttgggttt atccctaatt gaatcactct tcccaatgac aacaaccaga acatatgacg  12660
agatcacatt acacctccac agtaaattta gctgctgtat ccgagaagtg cctgttgcgg  12720
ttcccttcga gctcctcggg ctggcaccgg aattaaggat ggtaacctca aataagttca  12780
tgtatgatcc tagccctata tcagagagag atttcgcgag acttgactta gctatcttca  12840
agagttatga gcttaattta gaatcatatt ccacgctgga gctaatgaac attctttcaa  12900
tatctagcgg gaagttgatt ggccaatccg tggtttctta tgatgaagat acctctataa  12960
agaatgatgc tataatagtg tatgacaaca cacgaaattg gattagtgag gcgcagaact  13020
cagatgtggt ccgcctgttt gagtatgcag cactcgaagt gctccttgac tgtgcttatc  13080
aactttacta tctgagggta aggggtctaa acaacatcgt cctatacatg aatgacttat  13140
ataagaacat gccagggatc ctactctcca atattgcggc cacgatatcc caccccatca  13200
ttcactcaag gttgaatgca gtaggcctaa ttaaccatga cgggtcacac cagcttgcag  13260
atatagactt cgtcgaggtg tctgcaaaat tgttagtctc ttgcactcga cgcgtggtct  13320
caggcttata tgcagggaat aagtacgatc tgctgtttcc atctgtctta gatgataacc  13380
tgaatgagaa gatgcttcaa ctgatttccc ggttatgctg tctgtacaca gtgctctttg  13440
ctacaacaag agaaatccca aaaataaggg gtctatcggc agaagagaaa tgctcaatac  13500
tcactgagta tctactgtca gatgctgtaa aaccattgct taggcccgaa caagtgagtt  13560
ctatcatgtc tcccaacata atcacgttcc cagccaatct atattacatg tctaggaaga  13620
gccttaattt gatcagagaa cgagaggaca gagatactat cttgtcattg ttgttccctc  13680
aggaaccact gcttgagctt cgcccagtac gagacattgg tgctcgagtg aaagacccgt  13740
ttacccggca acccgcatca ttcatacaag agctagatct gagtgcccca gcaaggtacg  13800
acgcatttac actgagtaag gtttgcttcg agcatacatt accgaaccca aaggaagatt  13860
acctagtacg gtacttgttc agaggaatag ggactgcttc atcttcttgg tataaggcat  13920
ctcatcttct atccgtacct gaggtcaggt gtgcaagaca tgggaactcc ttatacttag  13980
cggaaggaag cggagccatc atgagtcttc ttgaattgca tataccacat gagactatct  14040
```

-continued

```
attacaatac acttttctcg aatgagatga accctccaca gcgacatttc ggacctacac  14100
caacacagtt tctaaactcg gtcgtttata ggaatctaca agcggaagtg ccatgtaaag  14160
atggatatgt ccaggagttc tgcccattat ggagagagaa tgcagaagaa agtgacctga  14220
cctcagataa ggcagttgga tatatcacat ctgtggtacc ctacaggtct gtatcattac  14280
tacattgtga cattgagatt cctccagggt ccaatcaaag cttattagat caactggcta  14340
ctaatttatc cctgattgcc atgcattctg tgagggaggg cggggtagtg atcatcaaag  14400
tactgtatgc aatggggtac tacttccatt tactcatgaa tttattcact ccatgttcca  14460
cgaaaggata tacactctcc aatggctatg cctgtagagg ggatatggag tgttacctga  14520
tattcgtcat gggctactta ggcgggccca ccttcgtgca cgaagtggta aggatggcaa  14580
aaactctaat acaacgacac ggtacacttc tatctaaatc agatgaaatt acattgacta  14640
agctatttac ctcacagcag cgtcgtgtaa cagatatcct atccagccct ttaccgaagc  14700
taatgaggct cttgagagaa aatattgatg ctgcactaat tgaagccggg ggacagcccg  14760
tccgtccatt ctgtgcggaa agtttggtga gcacactaac agatatgacc cagacaactc  14820
agatcattgc cagccacatt gacacagtca ttcggtctgt aatttacatg gaggctgagg  14880
gtgatctcgc cgacacagtg ttcttattta ctccttacaa tctatccaca gacggtaaaa  14940
agagaacatc acttaagcag tgcaccaaac agatcttgga agtcacaata ctgggtctca  15000
gagccaaaga taccaataaa gtaggtgatg taatcagttt agtactcaga ggtgcggttt  15060
ccctagagga cctcatccca ttaaggacat acctgaagcg cagtacctgc cctaaatacc  15120
tgaaagcggt cctaggtatt actaaactca aagaaatgtt cacagatacc tcgttactgt  15180
acttgactcg tgctcagcaa aaattctaca tgaaaaccat aggtaatgct gccaagggat  15240
attacagtaa taatgactct taaaggcaat cgtacgccaa tcagttatct tcctaactga  15300
tgactccctc actgacttaa ttataccaga ttagaaaaaa gttaaattcc gactctttgg  15360
aactcgtatt cggattcagt tagttaactt taagcaagag tgcgcaaagt cgtccctaat  15420
tatagttatg tcattcacca aatctcwgct agaggatccc cgggtaccga gctcgaattc  15480
actggccgtc gttttacaac gtcgtgactg ggaaaaccct ggcgttaccc aacttaatcg  15540
ccttgcagca catccccctt tcgccagctg gcgtaatagc gaagaggccc gcaccgatcg  15600
cccttcccaa cagttgcgca gcctgaatgg cgaatggcgc ctgatgcggt attttctcct  15660
tacgcatctg tgcggtattt cacaccgcat atggtgcact ctcagtacaa tctgctctga  15720
tgccgcatag ttaagccagc cccgacaccc gccaacaccc gctgacgcgc cctgacgggc  15780
ttgtctgctc ccggcatccg cttacagaca agctgtgacc gtctccggga gctgcatgtg  15840
tcagaggttt tcaccgtcat caccgaaacg cgcgagacga aagggcctcg tgatacgcct  15900
atttttatag gttaatgtca tgataataat ggtttcttag acgtcaggtg gcacttttcg  15960
gggaaatgtg cgcggaaccc ctatttgttt atttttctaa atacattcaa atatgtatcc  16020
gctcatgaga caataaccct gataaatgct tcaataatat tgaaaaagga agagtatgag  16080
tattcaacat ttccgtgtcg cccttattcc cttttttgcg gcattttgcc ttcctgtttt  16140
tgctcaccca gaaacgctgg tgaaagtaaa agatgctgaa gatcagttgg gtgcacgagt  16200
gggttacatc gaactggatc tcaacagcgg taagatcctt gagagttttc gccccgaaga  16260
acgttttcca atgatgagca cttttaaagt tctgctatgt ggcgcggtat tatcccgtat  16320
tgacgccggg caagagcaac tcggtcgccg catacactat tctcagaatg acttggttga  16380
```

-continued

```
gtactcacca gtcacagaaa agcatcttac ggatggcatg acagtaagag aattatgcag  16440
tgctgccata accatgagtg ataacactgc ggccaactta cttctgacaa cgatcggagg  16500
accgaaggag ctaaccgctt ttttgcacaa catgggggat catgtaactc gccttgatcg  16560
ttgggaaccg gagctgaatg aagccatacc aaacgacgag cgtgacacca cgatgcctgt  16620
agcaatggca acaacgttgc gcaaactatt aactggcgaa ctacttactc tagcttcccg  16680
gcaacaatta atagactgga tggaggcgga taaagttgca ggaccacttc tgcgctcggc  16740
ccttccggct ggctggttta ttgctgataa atctggagcc ggtgagcgtg ggtctcgcgg  16800
tatcattgca gcactggggc cagatggtaa gccctcccgt atcgtagtta tctacacgac  16860
ggggagtcag gcaactatgg atgaacgaaa tagacagatc gctgagatag gtgcctcact  16920
gattaagcat tggtaactgt cagaccaagt ttactcatat atactttaga ttgatttaaa  16980
acttcatttt taatttaaaa ggatctaggt gaagatcctt tttgataatc tcatgaccaa  17040
aatcccttaa cgtgagtttt cgttccactg agcgtcagac cccgtagaaa agatcaaagg  17100
atcttcttga gatccttttt ttctgcgcgt aatctgctgc ttgcaaacaa aaaaaccacc  17160
gctaccagcg gtggtttgtt tgccggatca agagctacca actctttttc cgaaggtaac  17220
tggcttcagc agagcgcaga taccaaatac tgttcttcta gtgtagccgt agttaggcca  17280
ccacttcaag aactctgtag caccgcctac atacctcgct ctgctaatcc tgttaccagt  17340
ggctgctgcc agtggcgata agtcgtgtct taccgggttg gactcaagac gatagttacc  17400
ggataaggcg cagcggtcgg gctgaacggg gggttcgtgc acacagccca gcttggagcg  17460
aacgacctac accgaactga gatacctaca gcgtgagcta tgagaaagcg ccacgcttcc  17520
cgaagggaga aaggcggaca ggtatccggt aagcggcagg gtcggaacag gagagcgcac  17580
gagggagctt ccagggggaa acgcctggta tctttatagt cctgtcgggt ttcgccacct  17640
ctgacttgag cgtcgatttt tgtgatgctc gtcagggggg cggagcctat ggaaaaacgc  17700
cagcaacgcg gcctttttac ggttcctggc cttttgctgg ccttttgctc acatgttctt  17760
tcctgcgtta tcccctgatt ctgtggataa ccgtattacc gcctttgagt gagctgatac  17820
cgctcgccgc agccgaacga ccgagcgcag cgagtcagtg agcgaggaag cggaaga     17877
```

<210> SEQ ID NO 17
<211> LENGTH: 18288
<212> TYPE: DNA
<213> ORGANISM: Artificial Sequence
<220> FEATURE:
<223> OTHER INFORMATION: chemically synthesized

<400> SEQUENCE: 17

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg ccagagaatc    240
tgtgaggtac gataaaaggc gaagaagcaa tcgagatcgt acggtagaag gtgtgaaccc    300
cgagcgcgag gccgaagctc gaacctgagg gaaccttcta ccgatatgtc gtctgtttcg    360
acgaatacga gcagctcctt gctgctcaga cccgccctaa cggaactcat ggagggggag    420
agaaagggag cactttaaaa gttgaggtcc cagtatttac cctaaacagt gatgatccgg    480
aagatagatg gaattttgcg gtattctgtc ttcggattgc tgttagcgag gatgccaaca    540
aaccactcag gcaaggtgct cttatatccc tcttatgctc ccattctcag gtgatgagaa    600
```

-continued

```
accatgttgc ccttgcaggg aaacagaatg aggccacact ggctgttctt gagatcgatg    660
gttttgctaa cagtgtgccc cagttcaaca ataggagtgg agtgtctgag gagagagcac    720
agagattcat ggtaatcgca ggatctctcc ctcgggcatg cagcaacggt actccgtttg    780
tcacggctgg ggttgaagat gatgcaccag aagatatcac tgacactctg gaaagaatcc    840
tatctatcca agttcaggta tgggtcacag tagcaaaggc catgactgca tatgagacag    900
cagatgagtc agaaacaaga agaataaata agtatatgca gcaaggtcga gttcagaaaa    960
agtacatcct tcatcctgta tgcaggagtg caattcaact cacaatcaga cattctctgg   1020
cagtccgtat tttcctagtt agtgagctca agaggggccg caatacagca ggtgggagct   1080
ctacatatta caacttggtc ggggatgtag actcatacat caggaacacc gggcttactg   1140
catttttcct aacactcaaa tatggaatca ataccaagac gtcagccctc gcactcagca   1200
gcctcacagg tgatatccaa aaaatgaaac agctcatgcg tttatatcgg atgaaaggtg   1260
aaaatgcacc atacatgaca ttgttaggcg acagtgacca gatgagcttt gcaccagctg   1320
agtatgcaca actttattct tttgccatgg gcatggcatc agtcttagat aagggaactg   1380
gcaagtacca attcgccagg gactttatga gcacatcatt ctggagactt ggagtagagt   1440
atgctcaggc ccagggaagt agcattaatg aggacatggc tgctgagcta aaactaaccc   1500
tggcagcaag gagaggcctg gcagctgctg cccaacgagt atccgaagaa atcggcagca   1560
tggacattcc cactcaacag gcgggagtcc tcaccgggct cagtgacgaa ggcccccgaa   1620
ctccacaggg cggatcaaac aagccgcaag ggcaaccaga tgccggggat ggggagaccc   1680
aattcttgga ttttatgaga gcagtggcga acagcatgcg ggaagcgcca aatcctgcac   1740
agagcaccac ccatccagag cctcccccaa cccctggggc atcccaagac aacgacactg   1800
actgggggta ctgatcgaca acacccagcc cgccttcaca ggaccacacc aaaccccccg   1860
cccaaaactc tcccacactc cccgacccac aaccccgcac gaccacacca acaaaagctc   1920
cccccccccc tctcccccac ccccagccac acgatcccac ccacccggga caacacaggc   1980
acagctcggc tcgtcgacaa cccgcccaga gcccaaggta ttagaaaaaa atacgggtag   2040
aagagagaca tccagagacc aagacgagtc accaagttct ctgttctccc ttctacccag   2100
tggattaggg tgaagatggc cacttttaca gatgcggaga tagatgacat atttgagacc   2160
agtgggactg tcattgacag cataattacg gcccaggaca aatcagctga gaccgttgaa   2220
agaagcgcga tcccgcaggg caagaccaaa gctctaagca cagcatggga gaagcacggg   2280
agtgtccagc cacacgccag tcaggacgcc cctgaccaac aagacagaac agaaaaacag   2340
ccatccacac ctgagcaggt gactctacac aacaacccgc cgatcacatc cactggaccg   2400
cctcccactc aggccgcaag cgagaccagc gacacacagc tcaagactgg agcaagcaac   2460
tcccttctgt ccatgctcga caaactgagc aataaatcgt ccaatgctaa aaagggccca   2520
tggtcgggtt cccaagaagg gcatcaccaa cctccggccc aacaacacgg ggaccagccg   2580
agctatggaa gcaaccaggg aagaccgcag catcaggcca aggccgtccc tggaaaccgg   2640
ggcacagacg agaacacagc atatcatgga caacggaagg agtcacaact atcagctggt   2700
gcaacccctc atgcgcccca gtcagggcag agccaagaca atactcctgt acctgtggat   2760
cgtgtccagc tatctgccga ctttgcgcag gcgatgatgt ctatgatgga ggcattatca   2820
cagaaggtaa gtaaagttga tcatcagctg gacctagtct tgaaacagac atcctccatt   2880
cctatgatgc gatctgaaat ccaacagctc aagacatctg ttgcgatcat ggaagctaac   2940
```

-continued

```
ttaggcatga tgaaaattct ggaccctggt tgtgctaacg tttcatcctt aagtgatctc   3000
cgggcagtag cccgatccca cccagtccta gtttcaggcc ccggagaccc atctccttac   3060
gtgacacaag gggtgaaat gacgctcaat aaactctcac aaccggtgca gcacccctct   3120
gaattgatta agtctgccac tgcaagcggg cctgacatgg gagtggagaa ggacactgtc   3180
cgcgcattaa tcacctcgcg cccgatgcat ccgagctcct cggctaagct cctgagcaag   3240
ctagatgcag ccaggtcaat tgaagagatc aggaagatca aacgccttgc gctgaatggt   3300
tgatggccat cacaactcat aacaggctcc cgtcacttta gcgtcacacg gaatccctcg   3360
ggggccctcg tttcacttat ttttagctag ttggtggaag aaggtacgta ggtctgctag   3420
gaacttctcc attgaagtag tgttgcctgc tgccgtggga catggtgcct tgagggaggt   3480
gctgctggca ttcaggagct gacgcatgtt gaggaagaga ccctgcaggt tcttgtggca   3540
gtgctggctc tcccaaacaa ttgtggaggc tttgcataag agctcagttt tgttatttgt   3600
cttattgtct gcaaagatat ctgtcacgtt catcttgacg caggaaacct ctccctggat   3660
gtcattcact atccggatgc tctccatcag cggcactgag agctgtaagc acagcgtggg   3720
cacagcccca gggccggcca gcagcaccag cagtgccagc agggtgggca gtgaggagct   3780
catggtactt ctacccgtat tttttctaag agggcccccc ctcgcaaatc cacgcttcaa   3840
cacccaaaac aacagccctc tctcaccccc ctcaatcccc cgaatgatcg cacaactgca   3900
accaatccag ctgcattaga aattaagaaa aaatacgggt agaatcagag tgccttgatt   3960
gcaccaaaat ggactcatcc aggacaatcg ggctgtactt tgattctgcc ctcccttcca   4020
gcagcctgtt agcatttccg attgtcttac aagacacagg agacgggaag aagcaaatca   4080
ccccacaata caggatccag cgccttgatt cgtggacaga cagtaaggaa gactcggtat   4140
tcatcaccac ctacgggttc atctttcaaa ttgggaatga agaagccact gtcggtgtga   4200
tcaatgacaa tcccaagcac gagctactct cttccgcaat gctctgctta gggagtgtcc   4260
cgaacgacgg agatcttgtt gagctggcaa gagcctgcct caccatggtg gtaacttgca   4320
agaagagtgc aactaacact gagagaatag tcttctcagt agtgcaggca cctcgggtgc   4380
tgcaaagctg tatggttgtg gcaaataggt actcatcagt gaatgcagtg aagcatgtga   4440
aggcgccaga aaagatccct gggagcggaa ccctagagta taaagtgaat tttgtctctt   4500
tgaccgtggt gccaagaagg gatgtctaca ggatcccaac tgcagtattg aaagtgtctg   4560
gctcaagcct gtacaatctt gcgctcaatg tcactattga tgtggacgtg gatccgaaga   4620
gcccgttagt caaatccctt tctaagtccg atagcggata ctatgcgaat ctttttctgc   4680
atatcgggct tatgtccact gtagataaga aggggaagaa agtgacattt gacaagatag   4740
aggaaaagat aaggagactc aatctatccg tcgggctcag tgatgtgctc ggaccctctg   4800
tgcttgtgaa ggcgagaggt gcacggacta agttacttgc tcctttcttc tctagcagtg   4860
ggacagcctg ctatcctata gcaaatgcct ctccccaggt tgccaagata ctctggagcc   4920
aaactgcgca cctgcggagt gtgaaagtca tcattcaagc cggcactcag cgtgctgtcg   4980
cagtgaccgc tgatcatgag gtaacctcca ctaagataga gaggaggcat gccattgcta   5040
aatacaatcc tttcaggaaa taagttgcat ccctaagact gcagttcacc tgctttctcg   5100
aatcaccatt acaccagaca atgatccatc tcgactgctt atagttagtt cacctgtcta   5160
gcaaattaga aaaaacacgg gtagaagagt ctggatcccg accggcacat tcaggacgca   5220
atatgggctc caaactttct accaggatcc cagcacctct gatgctgatc acccggatta   5280
tgctgatatt gggctgtatc cgtccgacca gctctcttga cggcaggcct cttgcagctg   5340
```

-continued

```
caggaattgt agtaacagga gataaggcag tcaatgtata cacctcgtct cagacagggt   5400
caatcatagt caagttgctc ccgaatatgc ccagggataa ggaggcgtgt gcgaaagccc   5460
cattagaggc atataacaga acactgacta ctttgctcac tcctcttggc gactccatcc   5520
gcaagatcca agggtctgtg tccacgtctg gaggagggag acaagggcgc cttataggtg   5580
ctgttattgg cagtgtagct cttggggttg caacagcggc acagataaca gcagctgcgg   5640
ccctaataca agccaaccgg aatgccgcca acatcctccg gcttaaggag agcattgctg   5700
caaccaatga agctgtgcat gaagtcaccg acggattatc gcaactatca gtggcagttg   5760
ggaagatgca gcagtttgtc aatgaccagt ttaataatac ggcgcgagaa ttggactgta   5820
taaaaatcac acaacaggtt ggtgtagaac tcaacctata cctgactgaa ttgactacag   5880
tattcgggcc acagatcacc tcccctgcat taactcagct gaccatccag gcactttata   5940
atttagctgg tggcaatatg gattacttat taactaggtt aggtataggg aacaatcaac   6000
tcagctcatt gattggtagc ggcctgatca ctggttaccc tatactgtat gactcacaga   6060
ctcaactctt gggcatacaa gtgaatttgc cctcagtcgg gaacttaaat aatatgcgtg   6120
ccacctattt ggagacctta tctgtaagta caaccaaagg atatgcctca gcacttgtcc   6180
cgaaagtagt aacacaagtc ggttctgtga tagaagagct tgacacctca tactgtatag   6240
agtccgatct ggatttatat tgtactagaa tagtgacact ccccatgtcc ccaggtattt   6300
attcctgttt gagcggcaac acatcagctt gcatgtactc aaagactgaa ggcgcactca   6360
ctacgccgta tatggccctt aaaggctcag ttattgccaa ttgtaagata acaacatgta   6420
gatgtacaga ccctcctggt atcatatcgc aaaattatgg agaagctgta tccctgatag   6480
atagacattt gtgcaatgtc ttatcattag acgggataac tctgaggctc agtggggaat   6540
ttgatgcaac ttatcaaaag aacatctcaa tactagattc tcaagtcatc gtgacaggca   6600
atcttgatat atcaactgaa cttggaaacg tcaacaattc aatcagcaat gccttggata   6660
ggttggcaga aagcaacagc aagctagaaa aagtcaatgt cagactaacc agcacatctg   6720
ctctcattac ctatattgtt ctaactgtca tttctctagt tttcggtgca cttagtctgg   6780
gtttagcgtg ttacctgatg tacaaacaga aggcacaaca aaagaccttg ctatggcttg   6840
ggaataatac cctcgatcag atgagagcca ctacaagagc atgaatgcag ataagaggtg   6900
gatatatacc caacagcagc ctgtgtgtca attccgataa cctgtcaagt agaagactta   6960
agaaaaaact actgggaaca agcaaccaaa gagcaataca cgggtagaac ggtcagagga   7020
gccacccttc aatcgggaat taggcttcac aacatccgtt ctatcacatc accgacaaca   7080
agagtcaatc atggaccgcg cggttaacag agtcgtgctg gagaatgagg aaagagaagc   7140
aaagaacaca tggcgcctgg ttttccggat cgcagtctta cttttaatgg taatgactct   7200
agctatctcc gcagctgccc tggcatacag tacgggggcc agtacgccgc acgacctcgc   7260
aggcatatcg actgtgatct ccaagacaga agataaggtt acatctttac tcagtttgag   7320
tcaagatgtg atagataaga tatacaagca ggtggctctt gaatccccgc tggcgctact   7380
aaacactgaa tctataatta tgaatgcaat aacctttctt tcttatcaaa ttaacggggc   7440
tgcgaacaat agcggatgtg ggcgcctgt tcatgaccca gattatatcg gggggatagg   7500
caaagaactc atagtggacg acatcagtga tgtcacatca ttttatcctt ctgcatatca   7560
agaacacttg aatttcatcc cggcgcctac tacaggatcc ggttgcactc ggataccctc   7620
atttgacatg agcaccaccc attattgtta tactcacaat gtgatactat ccggttgcag   7680
```

-continued

```
agatcactca cactcacatc aatacttagc acttggtgtg cttcggacat ctgcaacagg   7740
gagggtattc ttttctactc tgcgctccat caatttagat gacacccaaa atcggaagtc   7800
ctgcagtgtg agtgcaaccc ctttaggttg tgatatgctg tgctctaagg tcacagagac   7860
tgaagaggag gattacaagt cagttgcccc cacatcaatg gtgcacggaa ggctagggtt   7920
tgacggtcaa taccatgaga aggacttaga caccacggtc ttatttaagg attgggtggc   7980
aaattaccca ggggcgggag gagggtcttt tattgacgac cgtgtatggt tcccagttta   8040
cggagggctc aaacccaatt cacccagtga cactgcacaa gaagggaaat atgtaatata   8100
caagcgccat aacaacacat gccctgatga acaagattac caaattcgga tggctaagtc   8160
ttcatataaa cccgggcgat ttggtggaaa gcgcgtacag caagccatct tatccatcaa   8220
agtgtcaaca tccttgggta aggacccggt gctgactatt ccacctaata caatcacact   8280
catgggagcc gaaggcagaa tcctcacagt agggacatct cacttcttgt accaacgagg   8340
gtcttcatat ttctcccctg ccttattata tcccatgaca gtaaataaca aaacggctac   8400
actccatagt ccttatacgt ttaatgcttt cactcggcca ggtagtgtcc cttgccaggc   8460
atcagcaaga tgccccaact catgcatcac tggggtctat actgatccat atcccttaat   8520
cttccatagg aatcatactc tacgaggggt cttcgggacg atgcttgatg atgaacaagc   8580
gagacttaac cccgtatctg cagtattcga caacatatct cgcagtcgtg tcacccgggt   8640
gagttcaagc agcaccaagg cagcatacac gacatcgaca tgttttaaag ttgtcaagac   8700
caataaaact tattgtctta gtattgcaga aatatccaat accctattcg gggaatttag   8760
gatcgttccc ttattagttg agatcctcaa ggatgataga gtttaagaag ctagacttgg   8820
ccgattgagc caatcatagg atggttggga agacgacacc acaccaatca tctcccacaa   8880
tgcttagagt caagctgaat attaacataa gccaggatcc catgttgttg ggcagccaca   8940
accagacaat gctgacatga ttattctgag tcccgcccac tatcacttta ttaagaaaaa   9000
atacagaaag cattgagatg taagggaaaa caaccaacaa gagggaacac gggtaggaca   9060
tggcgggctc cggtcccgaa agggcagagc accagatcat cctaccagag tcacatctat   9120
cctctccatt ggtcaagcac aaattgctat actactggaa attgactggg ctaccgcttc   9180
ctgatgaatg cgactttgac catctcatta tcagcaggca atggaagaga atactggagt   9240
cggccactcc tgacacagag agaatgataa aactcgggcg ggcagtgcac cagactctca   9300
accacaattc caagataacc ggagtgctcc atcccaggtg tttagaagaa ctggctagta   9360
ttgaggtccc agattcaact aacaaattcc ggaagattga aaagaagatc cagattcaca   9420
acacaaggta tggagacctg ttcacaaagc tgtgcacgca tgttgagaag aaattgctag   9480
gatcgtcccg gtctaataat gtcccacgat cagaggaatt cagtagtatc cgtacagatc   9540
cggcattctg gtttcactca aaatggtcca gagccaagtt cgcgtggctc catataaaac   9600
aagtccaaag gcatctgatt gtagcagcaa ggacaaggtc tgcagtcaac aagttagtaa   9660
cattaagtca taagataggc cacgtctttg tttctcctga gcttgtcatt gtgacacata   9720
cagatgagaa caagttcaca tgcctcaccc aggaacttgt attgatgtat gcggatatga   9780
tggaaggcag ggacatggtc aatataatat cttctacagc agcacatctc agaaacctat   9840
ccgagaaaat tgacgatatt ctgcgattag tagatgccct ggcaaaggac ttaggtaatc   9900
aagtctatga cgttgtagca ttaatggagg gattcgcata cggtgccgtt cagctgcttg   9960
agccatcagg tacatttgca ggagatttct ttgcatttaa cctacaggag ctcaaagaca  10020
ctttaatcga acttctccca aataatatag cggaatcagt aactcacgct attgccactg  10080
```

-continued

```
tattctccgg cttagaacag aatcaagcag ctgagatgtt gtgcttgcta cgtttgtggg  10140
gtcatccatt gcttgagtct cgtagtgcag caagagcagt caggagccag atgtgcgcac  10200
caaagatggt agatttcgat atgatcctcc aagtattatc tttctttaaa ggaacaatca  10260
tcaatggata cagaaagaag aactcaggtg tgtggccgcg tgtcaaagta gatacaatat  10320
acgggaatat cattgggcag ctacatgctg attcagcaga gatctcacat gatgtcatgt  10380
tgagggagta caagagttta tctgctcttg aatttgagcc atgtatagat tatgaccctg  10440
ttaccaatct aagcatgttc ctaaaagaca aggcaatcgc acatcctagt gataattggc  10500
tcgcctcatt taggcggaac ctactctctg aggaccagaa gaaacagata aaagaggcaa  10560
cttcaactaa ccgcctcctg atagagttct tagaatcaaa tgattttgat ccatataaag  10620
aaatggaata cctgacaacc ctcgagtacc taagagatga cagtgtggcg gtatcgtact  10680
cactcaaaga gaaagaggtg aaagtgaatg ggcggatctt tgctaagtta acaaagaaac  10740
taaggaactg ccaggtaatg gcagaaggaa ttctagctga ccagattgca cctttctttc  10800
agggaaatgg ggtcattcaa gatagcatat ccttgacaaa gagtatgtta gcgatgagtc  10860
aactgtcctt taacagcaat aagaaacgta tcactgactg caaagagagg gtttcctcga  10920
accgcaatca tgatcagaag agcaagaatc gtagaagagt tgccactttt atcacgactg  10980
acctacaaaa gtattgtctt aactggagat atcagacagt caaactattc gctcatgcta  11040
tcaatcagct gatgggccta cctcatttct ttgagtggat tcatcttagg ctgatggaca  11100
ctacaatgtt tgtaggggat cctttcaatc ctccaagtga cccgactgac tgtgatctat  11160
caagagtccc aaatgatgac atatatattg tcagtgctag agggggcatt gagggactct  11220
gccagaagct atggacgatg atctcaattg ctgcaatcca acttgctgca gcaagatctc  11280
attgtcgagt tgcctgcatg gtacaaggtg acaatcaagt aatagctgta acgagagagg  11340
taagatcaga tgattccccg gatatggtgt tgacgcagtt gcatcaagct agtgataatt  11400
tcttcaagga attaattcat gtcaatcatt tgattggcca taacctgaag gatcgtgaaa  11460
ccattagatc cgacacattc ttcatataca gcaaacgaat attcaaagat ggagcaatac  11520
tcagtcaggt cctcaaaaat tcatctaaat tggtgctaat atcaggcgac cttagcgaaa  11580
acactgtaat gtcctgtgcc aacattgcat ccactgtcgc acgactatgt gagaatgggc  11640
ttcctaagga tttctgttac tatttgaact acctaatgag ttgcgtgcag acatactttg  11700
attcggagtt ttctattacc cacagctcgc aatcagattc caaccagtcc tggatcgagg  11760
atatctcttt cgtacactca tacgtgttaa cccctgccca gctgggggga ctgagcaacc  11820
ttcaatactc aaggctctac acaaggaata ttggtgaccc agggaccact gctttcgcag  11880
aggtcaagcg actagaagca gtggggttgc tgagtcccag catcatgact aacatcttaa  11940
ccaggccacc tggcaatgga gactgggcca gcctatgcaa cgacccatac tcttttaatt  12000
ttgagactgt tgcaagccca aatattgtcc tcaagaaaca tacacagaaa gtcctatttg  12060
agacatgttc aaaccccta ttatccgggg tacatacaga ggacaatgag gcagaagaga  12120
aagcattggc tgaattctta ctcaatcaag aagtgattca cccgcgtgtc gcacatgcta  12180
tcatggaagc aagttctgtg ggtaggagaa agcaaattca agggcttgtt gacacaacga  12240
acactgtgat taagattgca ctgactagga ggcccctcgg tatcaaaagg ctgatgcgga  12300
taatcaacta ctcgagcatg catgcaatgt tgttcagaga tgatattttc ttatccaata  12360
gatccaacca cccattagtt tcttctaata tgtgctcgct gacgctagca gattatgccc  12420
```

-continued

```
ggaacagaag ctggtcaccc ctgacagggg gcaggaaaat actgggtgta tccaaccctg  12480
ataccataga acttgtggag ggagagattc tcagcgtcag tggagggtgc acaaaatgtg  12540
acagcggaga tgagcagttt acttggttcc atcttccaag caatatagag ctgactgatg  12600
acaccagcaa aaatcccccg atgagagtgc catatctcgg gtcgaagact caagagagga  12660
gagctgcctc gcttgcgaaa atagcccaca tgtcaccaca tgtgaaagca gcactaaggg  12720
catcatccgt gttaatctgg gcttatgggg acaacgaagt gaactggact gctgctctta  12780
atattgcaag gtctcgatgc aacataagct cagagtatct tcggctattg tcacccctgc  12840
ccacagctgg gaatctccaa catagattgg atgatggcat aacccagatg acatttaccc  12900
ctgcatctct ctacagagtg tcgccttacg ttcacatatc caatgattct caaaggctat  12960
tcaccgaaga aggggtcaaa gagggaaacg tggtttacca acaaattatg ctcttgggtt  13020
tatccctaat tgaatcactc ttcccaatga caacaaccag aacatatgac gagatcacat  13080
tacacctcca cagtaaattt agctgctgta tccgagaagt gcctgttgcg gttcccttcg  13140
agctcctcgg gctggcaccg gaattaagga tggtaacctc aaataagttc atgtatgatc  13200
ctagccctat atcagagaga gatttcgcga gacttgactt agctatcttc aagagttatg  13260
agcttaattt agaatcatat tccacgctgg agctaatgaa cattctttca atatctagcg  13320
ggaagttgat tggccaatcc gtggtttctt atgatgaaga tacctctata aagaatgatg  13380
ctataatagt gtatgacaac acacgaaatt ggattagtga ggcgcagaac tcagatgtgg  13440
tccgcctgtt tgagtatgca gcactcgaag tgctccttga ctgtgcttat caactttact  13500
atctgagggt aaggggtcta aacaacatcg tcctatacat gaatgactta tataagaaca  13560
tgccagggat cctactctcc aatattgcgg ccacgatatc ccaccccatc attcactcaa  13620
ggttgaatgc agtaggccta attaaccatg acgggtcaca ccagcttgca gatatagact  13680
tcgtcgaggt gtctgcaaaa ttgttagtct cttgcactcg acgcgtggtc tcaggcttat  13740
atgcagggaa taagtacgat ctgctgtttc catctgtctt agatgataac ctgaatgaga  13800
agatgcttca actgatttcc cggttatgct gtctgtacac agtgctcttt gctacaacaa  13860
gagaaatccc aaaaataagg ggtctatcgg cagaagagaa atgctcaata ctcactgagt  13920
atctactgtc agatgctgta aaaccattgc ttaggcccga acaagtgagt tctatcatgt  13980
ctcccaacat aatcacgttc ccagccaatc tatattacat gtctaggaag agccttaatt  14040
tgatcagaga acgagaggac agagatacta tcttgtcatt gttgttccct caggaaccac  14100
tgcttgagct tcgcccagta cgagacattg gtgctcgagt gaaagacccg tttacccggc  14160
aacccgcatc attcatacaa gagctagatc tgagtgcccc agcaaggtac gacgcattta  14220
cactgagtaa ggtttgcttc gagcatacat taccgaaccc aaaggaagat tacctagtac  14280
ggtacttgtt cagaggaata gggactgctt catcttcttg gtataaggca tctcatcttc  14340
tatccgtacc tgaggtcagg tgtgcaagac atgggaactc cttatactta gcggaaggaa  14400
gcggagccat catgagtctt cttgaattgc atataccaca tgagactatc tattacaata  14460
cacttttctc gaatgagatg aaccctccac agcgacattt cggacctaca ccaacacagt  14520
ttctaaactc ggtcgtttat aggaatctac aagcggaagt gccatgtaaa gatggatatg  14580
tccaggagtt ctgcccatta tggagagaga atgcagaaga aagtgacctg acctcagata  14640
aggcagttgg atatatcaca tctgtggtac cctacaggtc tgtatcatta ctacattgtg  14700
acattgagat tcctccaggg tccaatcaaa gcttattaga tcaactggct actaatttat  14760
ccctgattgc catgcattct gtgagggagg gcggggtagt gatcatcaaa gtactgtatg  14820
```

caatggggta ctacttccat ttactcatga atttattcac tccatgttcc acgaaaggat 14880
atacactctc caatggctat gcctgtagag gggatatgga gtgttacctg atattcgtca 14940
tgggctactt aggcgggccc accttcgtgc acgaagtggt aaggatggca aaaactctaa 15000
tacaacgaca cggtacactt ctatctaaat cagatgaaat tacattgact aagctattta 15060
cctcacagca gcgtcgtgta acagatatcc tatccagccc tttaccgaag ctaatgaggc 15120
tcttgagaga aaatattgat gctgcactaa ttgaagccgg gggacagccc gtccgtccat 15180
tctgtgcgga aagtttggtg agcacactaa cagatatgac ccagacaact cagatcattg 15240
ccagccacat tgacacagtc attcggtctg taatttacat ggaggctgag ggtgatctcg 15300
ccgacacagt gttcttattt actccttaca atctatccac agacggtaaa aagagaacat 15360
cacttaagca gtgcaccaaa cagatcttgg aagtcacaat actgggtctc agagccaaag 15420
ataccaataa agtaggtgat gtaatcagtt tagtactcag aggtgcggtt tccctagagg 15480
acctcatccc attaaggaca tacctgaagc gcagtacctg ccctaaatac ctgaaagcgg 15540
tcctaggtat tactaaactc aaagaaatgt tcacagatac ctcgttactg tacttgactc 15600
gtgctcagca aaaattctac atgaaaacca taggtaatgc tgccaaggga tattacagta 15660
ataatgactc ttaaaggcaa tcgtacgcca atcagttatc ttcctaactg atgactccct 15720
cactgactta attataccag attagaaaaa agttaaattc cgactctttg gaactcgtat 15780
tcggattcag ttagttaact ttaagcaaga gtgcgcaaag tcgtccctaa ttatagttat 15840
gtcattcacc aaatctcwgc tagaggatcc ccgggtaccg agctcgaatt cactggccgt 15900
cgttttacaa cgtcgtgact gggaaaaccc tggcgttacc caacttaatc gccttgcagc 15960
acatccccct ttcgccagct ggcgtaatag cgaagaggcc cgcaccgatc gcccttccca 16020
acagttgcgc agcctgaatg gcgaatggcg cctgatgcgg tattttctcc ttacgcatct 16080
gtgcggtatt tcacaccgca tatggtgcac tctcagtaca atctgctctg atgccgcata 16140
gttaagccag ccccgacacc cgccaacacc cgctgacgcg ccctgacggg cttgtctgct 16200
cccggcatcc gcttacagac aagctgtgac cgtctccggg agctgcatgt gtcagaggtt 16260
ttcaccgtca tcaccgaaac gcgcgagacg aaagggcctc gtgatacgcc tatttttata 16320
ggttaatgtc atgataataa tggtttctta gacgtcaggt ggcacttttc ggggaaatgt 16380
gcgcggaacc cctatttgtt tatttttcta aatacattca aatatgtatc cgctcatgag 16440
acaataaccc tgataaatgc ttcaataata ttgaaaaagg aagagtatga gtattcaaca 16500
tttccgtgtc gcccttattc ccttttttgc ggcattttgc cttcctgttt ttgctcaccc 16560
agaaacgctg gtgaaagtaa aagatgctga agatcagttg ggtgcacgag tgggttacat 16620
cgaactggat ctcaacagcg gtaagatcct tgagagtttt cgccccgaag aacgttttcc 16680
aatgatgagc acttttaaag ttctgctatg tggcgcggta ttatcccgta ttgacgccgg 16740
gcaagagcaa ctcggtcgcc gcatacacta ttctcagaat gacttggttg agtactcacc 16800
agtcacagaa aagcatctta cggatggcat gacagtaaga gaattatgca gtgctgccat 16860
aaccatgagt gataacactg cggccaactt acttctgaca acgatcggag gaccgaagga 16920
gctaaccgct tttttgcaca acatggggga tcatgtaact cgccttgatc gttgggaacc 16980
ggagctgaat gaagccatac caaacgacga gcgtgacacc acgatgcctg tagcaatggc 17040
aacaacgttg cgcaaactat taactggcga actacttact ctagcttccc ggcaacaatt 17100
aatagactgg atggaggcgg ataaagttgc aggaccactt ctgcgctcgg cccttccggc 17160

-continued

```
tggctggttt attgctgata aatctggagc cggtgagcgt gggtctcgcg gtatcattgc  17220
agcactgggg ccagatggta agccctcccg tatcgtagtt atctacacga cggggagtca  17280
ggcaactatg gatgaacgaa atagacagat cgctgagata ggtgcctcac tgattaagca  17340
ttggtaactg tcagaccaag tttactcata tatactttag attgatttaa aacttcattt  17400
ttaatttaaa aggatctagg tgaagatcct ttttgataat ctcatgacca aaatccctta  17460
acgtgagttt tcgttccact gagcgtcaga ccccgtagaa aagatcaaag gatcttcttg  17520
agatcctttt tttctgcgcg taatctgctg cttgcaaaca aaaaaaccac cgctaccagc  17580
ggtggtttgt ttgccggatc aagagctacc aactcttttt ccgaaggtaa ctggcttcag  17640
cagagcgcag ataccaaata ctgttcttct agtgtagccg tagttaggcc accacttcaa  17700
gaactctgta gcaccgccta catacctcgc tctgctaatc ctgttaccag tggctgctgc  17760
cagtggcgat aagtcgtgtc ttaccgggtt ggactcaaga cgatagttac cggataaggc  17820
gcagcggtcg ggctgaacgg ggggttcgtg cacacagccc agcttggagc gaacgaccta  17880
caccgaactg agatacctac agcgtgagct atgagaaagc gccacgcttc ccgaagggag  17940
aaaggcggac aggtatccgg taagcggcag ggtcggaaca ggagagcgca cgagggagct  18000
tccaggggga aacgcctggt atctttatag tcctgtcggg tttcgccacc tctgacttga  18060
gcgtcgattt ttgtgatgct cgtcaggggg gcggagccta tggaaaaacg ccagcaacgc  18120
ggccttttta cggttcctgg ccttttgctg gccttttgct cacatgttct ttcctgcgtt  18180
atcccctgat tctgtggata accgtattac cgcctttgag tgagctgata ccgctcgccg  18240
cagccgaacg accgagcgca gcgagtcagt gagcgaggaa gcggaaga               18288
```

```
<210> SEQ ID NO 18
<211> LENGTH: 15628
<212> TYPE: DNA
<213> ORGANISM: Artificial Sequence
<220> FEATURE:
<223> OTHER INFORMATION: chemically synthesized

<400> SEQUENCE: 18

gagaatctgt gaggtacgat aaaaggcgaa gaagcaatcg agatcgtacg ggtagaaggt     60
gtgaaccccg agcgcgaggc cgaagctcga acctgaggga accttctacc gatatgtcgt    120
ctgttttcga cgaatacgag cagctccttg ctgctcagac ccgccctaac ggaactcatg    180
gagggggaga gaaagggagc actttaaaag ttgaggtccc agtatttacc ctaaacagtg    240
atgatccgga agatagatgg aattttgcgg tattctgtct tcggattgct gttagcgagg    300
atgccaacaa accactcagg caaggtgctc ttatatccct cttatgctcc cattctcagg    360
tgatgagaaa ccatgttgcc cttgcaggga aacagaatga ggccacactg gctgttcttg    420
agatcgatgg ttttgctaac agtgtgcccc agttcaacaa taggagtgga gtgtctgagg    480
agagagcaca gagattcatg gtaatcgcag gatctctccc tcgggcatgc agcaacggta    540
ctccgtttgt cacggctggg gttgaagatg atgcaccaga agatatcact gacactctgg    600
aaagaatcct atctatccaa gttcaggtat gggtcacagt agcaaaggcc atgactgcat    660
atgagacagc agatgagtca gaaacaagaa gaataaataa gtatatgcag caaggtcgag    720
ttcagaaaaa gtacatcctt catcctgtat gcaggagtgc aattcaactc acaatcagac    780
attctctggc agtccgtatt ttcctagtta gtgagctcaa gaggggccgc aatacagcag    840
gtgggagctc tacatattac aacttggtcg gggatgtaga ctcatacatc aggaacaccg    900
ggcttactgc atttttccta acactcaaat atggaatcaa taccaagacg tcagccctcg    960
```

-continued

```
cactcagcag cctcacaggt gatatccaaa aaatgaaaca gctcatgcgt ttatatcgga   1020
tgaaaggtga aaatgcacca tacatgacat tgttaggcga cagtgaccag atgagctttg   1080
caccagctga gtatgcacaa ctttattctt ttgccatggg catggcatca gtcttagata   1140
agggaactgg caagtaccaa ttcgccaggg actttatgag cacatcattc tggagacttg   1200
gagtagagta tgctcaggcc cagggaagta gcattaatga ggacatggct gctgagctaa   1260
aactaaccct ggcagcaagg agaggcctgg cagctgctgc ccaacgagta tccgaagaaa   1320
tcggcagcat ggacattccc actcaacagg cgggagtcct caccgggctc agtgacgaag   1380
gcccccgaac tccacagggc ggatcaaaca agccgcaagg gcaaccagat gccggggatg   1440
gggagaccca attcttggat tttatgagag cagtggcgaa cagcatgcgg gaagcgccaa   1500
atcctgcaca gagcaccacc catccagagc ctcccccaac ccctggggca tcccaagaca   1560
acgacactga ctgggggtac tgatcgacaa cacccagccc gccttcacag gaccacacca   1620
aacccccgc ccaaaactct cccacactcc ccgacccaca accccgcacg accacaccaa   1680
caaaagctcc cccccccct ctcccccacc cccagccaca cgatcccacc cacccgggac   1740
aacacaggca cagctcggct cgtcgacaac ccgcccagag cccaaggtat tagaaaaaaa   1800
tacgggtaga agagagacat ccagagacca agacgagtca ccaagttctc tgttctccct   1860
tctacccagt ggattagggt gaagatggcc acttttacag atgcggagat agatgacata   1920
tttgagacca gtgggactgt cattgacagc ataattacgg cccaggacaa atcagctgag   1980
accgttgaaa gaagcgcgat cccgcagggc aagaccaaag ctctaagcac agcatgggag   2040
aagcacggga gtgtccagcc acacgccagt caggacgccc ctgaccaaca agacagaaca   2100
gaaaaacagc catccacacc tgagcaggtg actctacaca acaacccgcc gatcacatcc   2160
actggaccgc ctcccactca ggccgcaagc gagaccagcg acacacagct caagactgga   2220
gcaagcaact cccttctgtc catgctcgac aaactgagca ataaatcgtc caatgctaaa   2280
aagggcccat ggtcgggttc ccaagaaggg catcaccaac ctccggccca acaacacggg   2340
gaccagccga gctatggaag caaccaggga agaccgcagc atcaggccaa ggccgtccct   2400
ggaaaccggg gcacagacga gaacacagca tatcatggac aacggaagga gtcacaacta   2460
tcagctggtg caacccctca tgcgccccag tcagggcaga gccaagacaa tactcctgta   2520
cctgtggatc gtgtccagct atctgccgac tttgcgcagg cgatgatgtc tatgatggag   2580
gcattatcac agaaggtaag taaagttgat catcagctgg acctagtctt gaaacagaca   2640
tcctccattc ctatgatgcg atctgaaatc caacagctca agacatctgt tgcgatcatg   2700
gaagctaact taggcatgat gaaaattctg gaccctggtt gtgctaacgt ttcatcctta   2760
agtgatctcc gggcagtagc ccgatcccac ccagtcctag tttcaggccc cggagaccca   2820
tctccttacg tgacacaagg gggtgaaatg acgctcaata aactctcaca accggtgcag   2880
cacccctctg aattgattaa gtctgccact gcaagcgggc ctgacatggg agtggagaag   2940
gacactgtcc gcgcattaat cacctcgcgc ccgatgcatc cgagctcctc ggctaagctc   3000
ctgagcaagc tagatgcagc caggtcaatt gaagagatca ggaagatcaa acgccttgcg   3060
ctgaatggtt gatggccatc acaactcata acaggctccc gtcactttag cgtcacacgg   3120
aatccctcgg gggccctcgt ttcacttatt tttagctagt tggtggaaga aggtacgtag   3180
gtctgctagg aacttctcca ttgaagtagt gttgcctgct gccgtgggac atggtgcctt   3240
gagggaggtg ctgctggcat tcaggagctg acgcatgttg aggaagagac cctgcaggtt   3300
```

-continued

```
cttgtggcag tgctggctct cccaaacaat tgtggaggct ttgcataaga gctcagtttt   3360
gttatttgtc ttattgtctg caaagatatc tgtcacgttc atcttgacgc aggaaacctc   3420
tccctggatg tcattcacta tccggatgct ctccatcagc ggcactgaga gctgtaagca   3480
cagcgtgggc acagccccag ggccggccag cagcaccagc agtgccagca gggtgggcag   3540
tgaggagctc atggtacttc tacccgtatt ttttctaaga gggcccccc tcgcaaatcc   3600
acgcttcaac acccaaaaca acagccctct ctcaccccc tcaatcccc gaatgatcgc   3660
acaactgcaa ccaatccagc tgcattagaa attaagaaaa aatacgggta gaatcagagt   3720
gccttgattg caccaaaatg gactcatcca ggacaatcgg gctgtacttt gattctgccc   3780
tcccttccag cagcctgtta gcatttccga ttgtcttaca agacacagga gacgggaaga   3840
agcaaatcac cccacaatac aggatccagc gccttgattc gtggacagac agtaaggaag   3900
actcggtatt catcaccacc tacgggttca tctttcaaat tgggaatgaa gaagccactg   3960
tcggtgtgat caatgacaat cccaagcacg agctactctc ttccgcaatg ctctgcttag   4020
ggagtgtccc gaacgacgga gatcttgttg agctggcaag agcctgcctc accatggtgg   4080
taacttgcaa gaagagtgca actaacactg agagaatagt cttctcagta gtgcaggcac   4140
ctcgggtgct gcaaagctgt atggttgtgg caaataggta ctcatcagtg aatgcagtga   4200
agcatgtgaa ggcgccagaa aagatccctg ggagcggaac cctagagtat aaagtgaatt   4260
ttgtctcttt gaccgtggtg ccaagaaggg atgtctacag gatcccaact gcagtattga   4320
aagtgtctgg ctcaagcctg tacaatcttg cgctcaatgt cactattgat gtggacgtgg   4380
atccgaagag cccgttagtc aaatcccttt ctaagtccga tagcggatac tatgcgaatc   4440
tttttctgca tatcgggctt atgtccactg tagataagaa ggggaagaaa gtgacatttg   4500
acaagataga ggaaaagata aggagactca atctatccgt cgggctcagt gatgtgctcg   4560
gaccctctgt gcttgtgaag gcgagaggtg cacggactaa gttacttgct cctttcttct   4620
ctagcagtgg gacagcctgc tatcctatag caaatgcctc tccccaggtt gccaagatac   4680
tctggagcca aactgcgcac ctgcggagtg tgaaagtcat cattcaagcc ggcactcagc   4740
gtgctgtcgc agtgaccgct gatcatgagg taacctccac taagatagag aggaggcatg   4800
ccattgctaa atacaatcct ttcaggaaat aagttgcatc cctaagactg cagttcacct   4860
gctttctcga atcaccatta caccagacaa tgatccatct cgactgctta tagttagttc   4920
acctgtctag caaattagaa aaaacacggg tagaagagtc tggatcccga ccggcacatt   4980
caggacgcaa tatgggctcc aaactttcta ccaggatccc agcacctctg atgctgatca   5040
cccggattat gctgatattg ggctgtatcc gtccgaccag ctctcttgac ggcaggcctc   5100
ttgcagctgc aggaattgta gtaacaggag ataaggcagt caatgtatac acctcgtctc   5160
agacagggtc aatcatagtc aagttgctcc cgaatatgcc cagggataag gaggcgtgtg   5220
cgaaagcccc attagaggca tataacagaa cactgactac tttgctcact cctcttggcg   5280
actccatccg caagatccaa gggtctgtgt ccacgtctgg aggagggaga caagggcgcc   5340
ttataggtgc tgttattggc agtgtagctc ttggggttgc aacagcggca cagataacag   5400
cagctgcggc cctaatacaa gccaaccgga atgccgccaa catcctccgg cttaaggaga   5460
gcattgctgc aaccaatgaa gctgtgcatg aagtcaccga cggattatcg caactatcag   5520
tggcagttgg gaagatgcag cagtttgtca atgaccagtt taataatacg gcgcgagaat   5580
tggactgtat aaaaatcaca caacaggttg gtgtagaact caacctatac ctgactgaat   5640
tgactacagt attcgggcca cagatcacct cccctgcatt aactcagctg accatccagg   5700
```

```
cactttataa tttagctggt ggcaatatgg attacttatt aactaggtta ggtataggga   5760
acaatcaact cagctcattg attggtagcg gcctgatcac tggttaccct atactgtatg   5820
actcacagac tcaactcttg ggcatacaag tgaatttgcc ctcagtcggg aacttaaata   5880
atatgcgtgc cacctatttg gagaccttat ctgtaagtac aaccaaagga tatgcctcag   5940
cacttgtccc gaaagtagta acacaagtcg gttctgtgat agaagagctt gacacctcat   6000
actgtataga gtccgatctg gatttatatt gtactagaat agtgacactc cccatgtccc   6060
caggtattta ttcctgtttg agcggcaaca catcagcttg catgtactca aagactgaag   6120
gcgcactcac tacgccgtat atggccctta aaggctcagt tattgccaat tgtaagataa   6180
caacatgtag atgtacagac cctcctggta tcatatcgca aaattatgga gaagctgtat   6240
ccctgataga tagacatttg tgcaatgtct tatcattaga cgggataact ctgaggctca   6300
gtggggaatt tgatgcaact tatcaaaaga acatctcaat actagattct caagtcatcg   6360
tgacaggcaa tcttgatata tcaactgaac ttggaaacgt caacaattca atcagcaatg   6420
ccttggatag gttggcagaa agcaacagca agctagaaaa agtcaatgtc agactaacca   6480
gcacatctgc tctcattacc tatattgttc taactgtcat ttctctagtt ttcggtgcac   6540
ttagtctggg tttagcgtgt tacctgatgt acaaacagaa ggcacaacaa aagaccttgc   6600
tatggcttgg gaataatacc ctcgatcaga tgagagccac tacaagagca tgaatgcaga   6660
taagaggtgg atatataccc aacagcagcc tgtgtgtcaa ttccgataac ctgtcaagta   6720
gaagacttaa gaaaaaacta ctgggaacaa gcaaccaaag agcaatacac gggtagaacg   6780
gtcagaggag ccacccttca atcgggaatt aggcttcaca acatccgttc tatcacatca   6840
ccgacaacaa gagtcaatca tggaccgcgc ggttaacaga gtcgtgctgg agaatgagga   6900
aagagaagca aagaacacat ggcgcctggt tttccggatc gcagtcttac ttttaatggt   6960
aatgactcta gctatctccg cagctgccct ggcatacagt acgggggcca gtacgccgca   7020
cgacctcgca ggcatatcga ctgtgatctc caagacagaa gataaggtta catctttact   7080
cagtttgagt caagatgtga tagataagat atacaagcag gtggctcttg aatccccgct   7140
ggcgctacta aacactgaat ctataattat gaatgcaata acctttcttt cttatcaaat   7200
taacggggct gcgaacaata gcggatgtgg ggcgcctgtt catgacccag attatatcgg   7260
ggggataggc aaagaactca tagtggacga catcagtgat gtcacatcat tttatccttc   7320
tgcatatcaa gaacacttga atttcatccc ggcgcctact acaggatccg gttgcactcg   7380
gataccctca tttgacatga gcaccaccca ttattgttat actcacaatg tgatactatc   7440
cggttgcaga gatcactcac actcacatca atacttagca cttggtgtgc ttcggacatc   7500
tgcaacaggg agggtattct tttctactct gcgctccatc aatttagatg acacccaaaa   7560
tcggaagtcc tgcagtgtga gtgcaacccc tttaggttgt gatatgctgt gctctaaggt   7620
cacagagact gaagaggagg attacaagtc agttgccccc acatcaatgg tgcacggaag   7680
gctagggttt gacggtcaat accatgagaa ggacttagac accacggtct tatttaagga   7740
ttgggtggca aattacccag gggcgggagg agggtctttt attgacgacc gtgtatggtt   7800
cccagtttac ggagggctca aacccaattc acccagtgac actgcacaag aagggaaata   7860
tgtaatatac aagcgccata acaacacatg ccctgatgaa caagattacc aaattcggat   7920
ggctaagtct tcatataaac ccgggcgatt tggtggaaag cgcgtacagc aagccatctt   7980
atccatcaaa gtgtcaacat ccttgggtaa ggacccggtg ctgactattc cacctaatac   8040
```

-continued

```
aatcacactc atgggagccg aaggcagaat cctcacagta gggacatctc acttcttgta   8100
ccaacgaggg tcttcatatt tctcccctgc cttattatat cccatgacag taaataacaa   8160
aacggctaca ctccatagtc cttatacgtt taatgctttc actcggccag gtagtgtccc   8220
ttgccaggca tcagcaagat gccccaactc atgcatcact ggggtctata ctgatccata   8280
tcccttaatc ttccatagga atcatactct acgaggggtc ttcgggacga tgcttgatga   8340
tgaacaagcg agacttaacc ccgtatctgc agtattcgac aacatatctc gcagtcgtgt   8400
cacccgggtg agttcaagca gcaccaaggc agcatacacg acatcgacat gttttaaagt   8460
tgtcaagacc aataaaactt attgtcttag tattgcagaa atatccaata ccctattcgg   8520
ggaatttagg atcgttccct tattagttga gatcctcaag gatgatagag tttaagaagc   8580
tagacttggc cgattgagcc aatcatagga tggttgggaa gacgacacca caccaatcat   8640
ctcccacaat gcttagagtc aagctgaata ttaacataag ccaggatccc atgttgttgg   8700
gcagccacaa ccagacaatg ctgacatgat tattctgagt cccgcccact atcactttat   8760
taagaaaaaa tacagaaagc attgagatgt aagggaaaac aaccaacaag agggaacacg   8820
ggtaggacat ggcgggctcc ggtcccgaaa gggcagagca ccagatcatc ctaccagagt   8880
cacatctatc ctctccattg gtcaagcaca aattgctata ctactggaaa ttgactgggc   8940
taccgcttcc tgatgaatgc gactttgacc atctcattat cagcaggcaa tggaagagaa   9000
tactggagtc ggccactcct gacacagaga gaatgataaa actcgggcgg gcagtgcacc   9060
agactctcaa ccacaattcc aagataaccg gagtgctcca tcccaggtgt ttagaagaac   9120
tggctagtat tgaggtccca gattcaacta acaaattccg gaagattgaa aagaagatcc   9180
agattcacaa cacaaggtat ggagacctgt tcacaaagct gtgcacgcat gttgagaaga   9240
aattgctagg atcgtcccgg tctaataatg tcccacgatc agaggaattc agtagtatcc   9300
gtacagatcc ggcattctgg tttcactcaa aatggtccag agccaagttc gcgtggctcc   9360
atataaaaca agtccaaagg catctgattg tagcagcaag gacaaggtct gcagtcaaca   9420
agttagtaac attaagtcat aagataggcc acgtctttgt ttctcctgag cttgtcattg   9480
tgacacatac agatgagaac aagttcacat gcctcaccca ggaacttgta ttgatgtatg   9540
cggatatgat ggaaggcagg gacatggtca atataatatc ttctacagca gcacatctca   9600
gaaacctatc cgagaaaatt gacgatattc tgcgattagt agatgccctg gcaaaggact   9660
taggtaatca agtctatgac gttgtagcat taatggaggg attcgcatac ggtgccgttc   9720
agctgcttga gccatcaggt acatttgcag gagatttctt tgcatttaac ctacaggagc   9780
tcaaagacac tttaatcgaa cttctcccaa ataatatagc ggaatcagta actcacgcta   9840
ttgccactgt attctccggc ttagaacaga atcaagcagc tgagatgttg tgcttgctac   9900
gtttgtgggg tcatccattg cttgagtctc gtagtgcagc aagagcagtc aggagccaga   9960
tgtgcgcacc aaagatggta gatttcgata tgatcctcca agtattatct ttctttaaag  10020
gaacaatcat caatggatac agaaagaaga actcaggtgt gtggccgcgt gtcaaagtag  10080
atacaatata cgggaatatc attgggcagc tacatgctga ttcagcagag atctcacatg  10140
atgtcatgtt gagggagtac aagagtttat ctgctcttga atttgagcca tgtatagatt  10200
atgaccctgt taccaatcta agcatgttcc taaaagacaa ggcaatcgca catcctagtg  10260
ataattggct cgcctcattt aggcggaacc tactctctga ggaccagaag aaacagataa  10320
aagaggcaac ttcaactaac cgcctcctga tagagttctt agaatcaaat gattttgatc  10380
catataaaga aatggaatac ctgacaaccc tcgagtacct aagagatgac agtgtggcgg  10440
```

tatcgtactc actcaaagag aaagaggtga aagtgaatgg gcggatcttt gctaagttaa 10500
caaagaaact aaggaactgc caggtaatgg cagaaggaat tctagctgac cagattgcac 10560
ctttctttca gggaaatggg gtcattcaag atagcatatc cttgacaaag agtatgttag 10620
cgatgagtca actgtccttt aacagcaata agaaacgtat cactgactgc aaagagaggg 10680
tttcctcgaa ccgcaatcat gatcagaaga gcaagaatcg tagaagagtt gccactttta 10740
tcacgactga cctacaaaag tattgtctta actggagata tcagacagtc aaactattcg 10800
ctcatgctat caatcagctg atgggcctac ctcatttctt tgagtggatt catcttaggc 10860
tgatggacac tacaatgttt gtaggggatc ctttcaatcc tccaagtgac ccgactgact 10920
gtgatctatc aagagtccca aatgatgaca tatatattgt cagtgctaga gggggcattg 10980
agggactctg ccagaagcta tggacgatga tctcaattgc tgcaatccaa cttgctgcag 11040
caagatctca ttgtcgagtt gcctgcatgg tacaaggtga caatcaagta atagctgtaa 11100
cgagagaggt aagatcagat gattccccgg atatggtgtt gacgcagttg catcaagcta 11160
gtgataattt cttcaaggaa ttaattcatg tcaatcattt gattggccat aacctgaagg 11220
atcgtgaaac cattagatcc gacacattct tcatatacag caaacgaata ttcaaagatg 11280
gagcaatact cagtcaggtc ctcaaaaatt catctaaatt ggtgctaata tcaggcgacc 11340
ttagcgaaaa cactgtaatg tcctgtgcca acattgcatc cactgtcgca cgactatgtg 11400
agaatgggct tcctaaggat ttctgttact atttgaacta cctaatgagt tgcgtgcaga 11460
catactttga ttcggagttt tctattaccc acagctcgca atcagattcc aaccagtcct 11520
ggatcgagga tatctctttc gtacactcat acgtgttaac cctgcccag ctgggggac 11580 tgagcaacct tcaatactca aggctctaca caaggaatat tggtgaccca gggaccactg 11640
ctttcgcaga ggtcaagcga ctagaagcag tggggttgct gagtcccagc atcatgacta 11700
acatcttaac caggccacct ggcaatggag actgggccag cctatgcaac gacccatact 11760
cttttaattt tgagactgtt gcaagcccaa atattgtcct caagaaacat acacagaaag 11820
tcctatttga gacatgttca aaccccttat tatccggggt acatacagag gacaatgagg 11880
cagaagagaa agcattggct gaattcttac tcaatcaaga agtgattcac ccgcgtgtcg 11940
cacatgctat catggaagca agttctgtgg gtaggagaaa gcaaattcaa gggcttgttg 12000
acacaacgaa cactgtgatt aagattgcac tgactaggag gcccctcggt atcaaaaggc 12060
tgatgcggat aatcaactac tcgagcatgc atgcaatgtt gttcagagat gatattttct 12120
tatccaatag atccaaccac ccattagttt cttctaatat gtgctcgctg acgctagcag 12180
attatgcccg gaacagaagc tggtcacccc tgacaggggg caggaaaata ctgggtgtat 12240
ccaaccctga taccatagaa cttgtggagg gagagattct cagcgtcagt ggagggtgca 12300
caaaatgtga cagcggagat gagcagttta cttggttcca tcttccaagc aatatagagc 12360
tgactgatga caccagcaaa aatcccccga tgagagtgcc atatctcggg tcgaagactc 12420
aagagaggag agctgcctcg cttgcgaaaa tagcccacat gtcaccacat gtgaaagcag 12480
cactaagggc atcatccgtg ttaatctggg cttatgggga caacgaagtg aactggactg 12540
ctgctcttaa tattgcaagg tctcgatgca acataagctc agagtatctt cggctattgt 12600
cacccctgcc cacagctggg aatctccaac atagattgga tgatggcata acccagatga 12660
catttacccc tgcatctctc tacagagtgt cgccttacgt tcacatatcc aatgattctc 12720
aaaggctatt caccgaagaa ggggtcaaag agggaaacgt ggtttaccaa caaattatgc 12780

-continued

```
tcttgggttt atccctaatt gaatcactct tcccaatgac aacaaccaga acatatgacg  12840
agatcacatt acacctccac agtaaattta gctgctgtat ccgagaagtg cctgttgcgg  12900
ttcccttcga gctcctcggg ctggcaccgg aattaaggat ggtaacctca aataagttca  12960
tgtatgatcc tagccctata tcagagagag atttcgcgag acttgactta gctatcttca  13020
agagttatga gcttaattta gaatcatatt ccacgctgga gctaatgaac attctttcaa  13080
tatctagcgg gaagttgatt ggccaatccg tggtttctta tgatgaagat acctctataa  13140
agaatgatgc tataatagtg tatgacaaca cacgaaattg gattagtgag gcgcagaact  13200
cagatgtggt ccgcctgttt gagtatgcag cactcgaagt gctccttgac tgtgcttatc  13260
aactttacta tctgagggta aggggtctaa acaacatcgt cctatacatg aatgacttat  13320
ataagaacat gccagggatc ctactctcca atattgcggc cacgatatcc caccccatca  13380
ttcactcaag gttgaatgca gtaggcctaa ttaaccatga cgggtcacac cagcttgcag  13440
atatagactt cgtcgaggtg tctgcaaaat tgttagtctc ttgcactcga cgcgtggtct  13500
caggcttata tgcagggaat aagtacgatc tgctgtttcc atctgtctta gatgataacc  13560
tgaatgagaa gatgcttcaa ctgatttccc ggttatgctg tctgtacaca gtgctctttg  13620
ctacaacaag agaaatccca aaaataaggg gtctatcggc agaagagaaa tgctcaatac  13680
tcactgagta tctactgtca gatgctgtaa aaccattgct taggcccgaa caagtgagtt  13740
ctatcatgtc tcccaacata atcacgttcc cagccaatct atattacatg tctaggaaga  13800
gccttaattt gatcagagaa cgagaggaca gagatactat cttgtcattg ttgttccctc  13860
aggaaccact gcttgagctt cgcccagtac gagacattgg tgctcgagtg aaagacccgt  13920
ttacccggca acccgcatca ttcatacaag agctagatct gagtgcccca gcaaggtacg  13980
acgcatttac actgagtaag gtttgcttcg agcatacatt accgaaccca aaggaagatt  14040
acctagtacg gtacttgttc agaggaatag ggactgcttc atcttcttgg tataaggcat  14100
ctcatcttct atccgtacct gaggtcaggt gtgcaagaca tgggaactcc ttatacttag  14160
cggaaggaag cggagccatc atgagtcttc ttgaattgca tataccacat gagactatct  14220
attacaatac acttttctcg aatgagatga accctccaca gcgacatttc ggacctacac  14280
caacacagtt tctaaactcg gtcgtttata ggaatctaca agcggaagtg ccatgtaaag  14340
atggatatgt ccaggagttc tgcccattat ggagagagaa tgcagaagaa agtgacctga  14400
cctcagataa ggcagttgga tatatcacat ctgtggtacc ctacaggtct gtatcattac  14460
tacattgtga cattgagatt cctccagggt ccaatcaaag cttattagat caactggcta  14520
ctaatttatc cctgattgcc atgcattctg tgagggaggg cggggtagtg atcatcaaag  14580
tactgtatgc aatggggtac tacttccatt tactcatgaa tttattcact ccatgttcca  14640
cgaaaggata tacactctcc aatggctatg cctgtagagg ggatatggag tgttacctga  14700
tattcgtcat gggctactta ggcgggccca ccttcgtgca cgaagtggta aggatggcaa  14760
aaactctaat acaacgacac ggtacacttc tatctaaatc agatgaaatt acattgacta  14820
agctatttac ctcacagcag cgtcgtgtaa cagatatcct atccagccct ttaccgaagc  14880
taatgaggct cttgagagaa aatattgatg ctgcactaat tgaagccggg ggacagcccg  14940
tccgtccatt ctgtgcggaa agtttggtga gcacactaac agatatgacc cagacaactc  15000
agatcattgc cagccacatt gacacagtca ttcggtctgt aatttacatg gaggctgagg  15060
gtgatctcgc cgacacagtg ttcttattta ctccttacaa tctatccaca gacggtaaaa  15120
agagaacatc acttaagcag tgcaccaaac agatcttgga agtcacaata ctgggtctca  15180
```

-continued

```
gagccaaaga taccaataaa gtaggtgatg taatcagttt agtactcaga ggtgcggttt  15240

ccctagagga cctcatccca ttaaggacat acctgaagcg cagtacctgc cctaaatacc  15300

tgaaagcggt cctaggtatt actaaactca aagaaatgtt cacagatacc tcgttactgt  15360

acttgactcg tgctcagcaa aaattctaca tgaaaaccat aggtaatgct gccaagggat  15420

attacagtaa taatgactct taaaggcaat cgtacgccaa tcagttatct tcctaactga  15480

tgactccctc actgacttaa ttataccaga ttagaaaaaa gttaaattcc gactctttgg  15540

aactcgtatt cggattcagt tagttaactt taagcaagag tgcgcaaagt cgtccctaat  15600

tatagttatg tcattcacca aatctcwg                                    15628


<210> SEQ ID NO 19
<211> LENGTH: 25
<212> TYPE: DNA
<213> ORGANISM: Artificial Sequence
<220> FEATURE:
<223> OTHER INFORMATION: chemically synthesized

<400> SEQUENCE: 19

ggtggctaca actatcaact aaact                                           25


<210> SEQ ID NO 20
<211> LENGTH: 24
<212> TYPE: DNA
<213> ORGANISM: Artificial Sequence
<220> FEATURE:
<223> OTHER INFORMATION: chemically synthesized

<400> SEQUENCE: 20

gtgtgtaact accgtgtact aagc                                            24


<210> SEQ ID NO 21
<211> LENGTH: 37
<212> TYPE: DNA
<213> ORGANISM: Artificial Sequence
<220> FEATURE:
<223> OTHER INFORMATION: chemically synthesized

<400> SEQUENCE: 21

atagttgtag ccacctcact tatttttagc tagttgg                              37


<210> SEQ ID NO 22
<211> LENGTH: 38
<212> TYPE: DNA
<213> ORGANISM: Artificial Sequence
<220> FEATURE:
<223> OTHER INFORMATION: chemically synthesized

<400> SEQUENCE: 22

acggtagtta cacacgtcat gagctcctca ctgcccac                             38


<210> SEQ ID NO 23
<211> LENGTH: 444
<212> TYPE: DNA
<213> ORGANISM: Artificial Sequence
<220> FEATURE:
<223> OTHER INFORMATION: chemically synthesized

<400> SEQUENCE: 23

atagttgtag ccacctcact tatttttagc tagttggtgg aagaaggtac gtaggtctgc     60

taggaacttc tccattgaag tagtgttgcc tgctgccgtg ggacatggtg ccttgaggga    120
```

-continued ggtgctgctg gcattcagga gctgacgcat gttgaggaag agaccctgca ggttcttgtg 180
gcagtgctgg ctctcccaaa caattgtgga ggctttgcat aagagctcag ttttgttatt 240
tgtcttattg tctgcaaaga tatctgtcac gttcatcttg acgcaggaaa cctctccctg 300
gatgtcattc actatccgga tgctctccat cagcggcact gagagctgta agcacagcgt 360
gggcacagcc ccagggccgg ccagcagcac cagcagtgcc agcagggtgg gcagtgagga 420
gctcatgacg tgtgtaacta ccgt 444

<210> SEQ ID NO 24
<211> LENGTH: 18758
<212> TYPE: DNA
<213> ORGANISM: Artificial Sequence
<220> FEATURE:
<223> OTHER INFORMATION: chemically synthesized

<400> SEQUENCE: 24
ggcgccggct gggcaacatt ccgaggggac cgtcccctcg gtaatggcga atgggacgcg 60
gccgatccgg ctgctaacaa agcccgaaag gaagctgagt tggctgctgc caccgctgag 120
caataactag cataacccct tggggcctct aaacgggtct tgaggggttt tttgctgaaa 180
ggaggaacta tatccggatg cggccgatcc ggctgctaac aaagcccgaa aggaagctga 240
gttggctgct gccaccgctg agcaataact agcataaccc cttggggcct ctaaacgggt 300
cttgaggggt tttttgctga aaggaggaac tatatccgga tggccgccac cggtgggcct 360
tgcagcacat ccccctttcg ccagctggcg taatagcgaa gaggcccgca ccgatcgccc 420
ttcccaacag ttgcgcagcc tgaatggcga atgggacgcg ccctgtagcg gcgcattaag 480
cgcggcgggt gtggtggtta cgcgcagcgt gaccgctaca cttgccagcg ccctagcgcc 540
cgctcctttc gctttcttcc cttcctttct cgccacgttc gccggctttc cccgtcaagc 600
tctaaatcgg gggctccctt tagggttccg atttagtgct ttacggcacc tcgaccccaa 660
aaaacttgat tagggtgatg gttcacgtag tgggccatcg ccctgataga cggtttttcg 720
ccctttgacg ttggagtcca cgttctttaa tagtggactc ttgttccaaa ctggaacaac 780
actcaaccct atctcggtct attcttttga tttataaggg attttgccga tttcggccta 840
ttggttaaaa aatgagctga tttaacaaaa atttaacgcg aattttaaca aaatattaac 900
gcttacaatt taggtggcac ttttcgggga aatgtgcgcg gaacccctat ttgtttattt 960
ttctaaatac attcaaatat gtatccgctc atgagacaat aaccctgata aatgcttcaa 1020
taatattgaa aaaggaagag tatgagtatt caacatttcc gtgtcgccct tattcccttt 1080
tttgcggcat tttgccttcc tgtttttgct cacccagaaa cgctggtgaa agtaaaagat 1140
gctgaagatc agttgggtgc acgagtgggt tacatcgaac tggatctcaa cagcggtaag 1200
atccttgaga gttttcgccc cgaagaacgt tttccaatga tgagcacttt taaagttctg 1260
ctatgtggcg cggtattatc ccgtattgac gccgggcaag agcaactcgg tcgccgcata 1320
cactattctc agaatgactt ggttgagtac tcaccagtca cagaaaagca tcttacggat 1380
ggcatgacag taagagaatt atgcagtgct gccataacca tgagtgataa cactgcggcc 1440
aacttacttc tgacaacgat cggaggaccg aaggagctaa ccgctttttt gcacaacatg 1500
ggggatcatg taactcgcct tgatcgttgg gaaccggagc tgaatgaagc cataccaaac 1560
gacgagcgtg acaccacgat gcctgtagca atggcaacaa cgttgcgcaa actattaact 1620
ggcgaactac ttactctagc ttcccggcaa caattaatag actggatgga ggcggataaa 1680
gttgcaggac cacttctgcg ctcggccctt ccggctggct ggtttattgc tgataaatct 1740

-continued

```
ggagccggtg agcgtgggtc tcgcggtatc attgcagcac tggggccaga tggtaagccc   1800
tcccgtatcg tagttatcta cacgacgggg agtcaggcaa ctatggatga acgaaataga   1860
cagatcgctg agataggtgc ctcactgatt aagcattggt aactgtcaga ccaagtttac   1920
tcatatatac tttagattga tttaaaactt catttttaat ttaaaaggat ctaggtgaag   1980
atcctttttg ataatctcat gaccaaaatc ccttaacgtg agttttcgtt ccactgagcg   2040
tcagaccccg tagaaaagat caaaggatct tcttgagatc ctttttttct gcgcgtaatc   2100
tgctgcttgc aaacaaaaaa accaccgcta ccagcggtgg tttgtttgcc ggatcaagag   2160
ctaccaactc tttttccgaa ggtaactggc ttcagcagag cgcagatacc aaatactgtt   2220
cttctagtgt agccgtagtt aggccaccac ttcaagaact ctgtagcacc gcctacatac   2280
ctcgctctgc taatcctgtt accagtggct gctgccagtg gcgataagtc gtgtcttacc   2340
gggttggact caagacgata gttaccggat aaggcgcagc ggtcgggctg aacggggggt   2400
tcgtgcacac agcccagctt ggagcgaacg acctacaccg aactgagata cctacagcgt   2460
gagctatgag aaagcgccac gcttcccgaa gggagaaagg cggacaggta tccggtaagc   2520
ggcagggtcg gaacaggaga gcgcacgagg gagcttccag ggggaaacgc ctggtatctt   2580
tatagtcctg tcgggtttcg ccacctctga cttgagcgtc gatttttgtg atgctcgtca   2640
ggggggcgga gcctatggaa aaacgccagc aacgcggcct ttttacgatt cctggccttt   2700
tgctggcctt ttgctcacat gttctttcct gcgttatccc ctgattctgt ggataaccgt   2760
attaccgcct ttgagtgagc tgataccgct cgccgcagcc gaacgaccga gcgcagcgag   2820
tcagtgagcg aggaagcgga agagcgccca atacgcaaac cgcctctccc cgcgcgttgg   2880
ccgattcatt aatgcagctg gcacgacagg tttcccgact ggaaagcggg cagtgagcgc   2940
aacgcaatta atgtgagtta gctcactcat taggcacccc aggctttaca ctttatgctt   3000
ccggctcgta tgttgtgtgg aattgtgagc ggataacaat ttcacacagg aaacagctat   3060
gaccatgatt acgccaagct cggaagcggc cgctaatacg actcactata gggaccaaac   3120
agagaatccg tgagtcgcga taaaaggcga aagagcaatt gaagtcacac gggtagaagg   3180
tgtgaatctc gagtgcgagc ccgaagcaca aactcgagaa agccttctgc caacatgtct   3240
tccgtatttg atgagtacga acagctcctc gcggctcaga ctcgccccaa tggagctcat   3300
ggagggggag aaaaagggag taccttaaaa gtagacgtcc cggtattcac tcttaacagt   3360
gatgacccag aagatagatg gagctttgtg gtattctgcc tccggattgc tgttagcgaa   3420
gatgccaaca aaccactcag gcaaggtgct ctcatatctc ttttatgctc ccactcacag   3480
gtaatgagga accatgttgc ccttgcaggg aaacagaatg aagccacatt ggccgtgctt   3540
gagattgatg gctttgccaa cggcacgccc cagttcaaca ataggagtgg agtgtctgaa   3600
gagagagcac agagatttgc gatgatagca ggatctctcc ctcgggcatg cagcaacgga   3660
accccgttcg tcacagccgg ggccgaagat gatgcaccag aagacatcac cgataccctg   3720
gataggatcc tctctatcca ggctcaagta tgggtcacag tagcaaaagc catgactgcg   3780
tatgagactg cagatgagtc ggaaacaagg cgaatcaata agtatatgca gcaaggcagg   3840
gtccaaaaga aatacatcct ctaccccgta tgcaggagca caatccaact cacgatcaga   3900
cagtctcttg cagtccgcat ctttttggtt agcgagctca agagaggccg caacacggca   3960
ggtggtacct ctacttatta taacctggta ggggacgtag actcatacat caggaatacc   4020
gggcttactg cattcttctt gacactcaag tacggaatca acaccaagac atcagccctt   4080
```

```
gcacttagta gcctctcagg cgacatccag aagatgaagc agctcatgcg tttgtatcgg   4140
atgaaaggag ataatgcgcc gtacatgaca ttacttggtg atagtgacca gatgagcttt   4200
gcgcctgccg agtatgcaca actttactcc tttgccatgg gtatggcatc agtcctagat   4260
aaaggtactg ggaaatacca atttgccagg gactttatga gcacatcatt ctggagactt   4320
ggagtagagt acgctcaggc tcagggaagt agcattaacg aggatatggc tgccgagcta   4380
aagctaaccc cagcagcaag gaggggcctg gcagctgctg cccaacgggt ctccgaggag   4440
accagcagca tagacatgcc tactcaacaa gtcggagtcc tcactgggct tagcgagggg   4500
gggtcccaag ctctacaagg cggatcgaat agatcgcaag ggcaaccaga agccggggat   4560
ggggagaccc aattcctgga tctgatgaga gcggtagcaa atagcatgag ggaggcgcca   4620
aactctgcac agggcactcc ccaatcgggg cctcccccaa ctcctgggcc atcccaagat   4680
aacgacaccg actgggggta ttgatggaca aaacccagcc tgcttccaca aaaacatccc   4740
aatgccctca cccgtagtcg acccctcgat ttgcggctct atatgaccac accctcaaac   4800
aaacatcccc ctctttcctc cctcccccctg ctgtacaact ccgcacgccc tagataccac   4860
aggcacaatg cggctcacta acaatcaaaa cagagccgag ggaattagaa aaaagtacgg   4920
gtagaagagg gatattcaga gatcagggca agtctcccga gtctctgctc tctcctctac   4980
ctgatagacc aggacaaaca tggccacctt tacagatgca gagatcgacg agctatttga   5040
gacaagtgga actgtcattg acaacataat tacagcccag ggtaaaccag cagagactgt   5100
tggaaggagt gcaatcccac aaggcaagac caaggtgctg agcgcagcat gggagaagca   5160
tgggagcatc cagccaccgg ccagtcaagg caaccccgat cgacaggaca gatctgacaa   5220
acaaccatcc acacccgggc aaacgacccc gcatgacagc ccgccggcca catccgccga   5280
ccagcccccc acccaggcca cagacgaagc cgtcgacaca cagctcagga ccggagcaag   5340
caactctctg ctgttgatgc ttgacaagct cagcaataaa tcgtccaatg ctaaaaaggg   5400
cccatggtcg agcccccaag aggggaatca ccaacgtccg actcaacagc aggggagtca   5460
acccagtcgc ggaaacagtc aggaaagacc gcagaaccaa gtcaaggccg cccctggaaa   5520
ccagggcaca gacgtgaaca cagcatatca tggacaatgg gaggagtcac aactatcagc   5580
tggtgcaacc cctcatgctc tccgatcaag gcagagccaa gacaataccc ttgtatctgc   5640
ggatcatgtc cagccacctg tagactttgt gcaagcgatg atgtctatga tggaggcgat   5700
atcacagaga gtaagtaagg tcgactatca gctagatctt gtcttgaaac agacatcctc   5760
catccctatg atgcggtccg aaatccaaca gctgaaaaca tctgttgcag tcatggaagc   5820
caacttggga atgatgaaga ttctggatcc cggttgtgcc aacatttcat ctctgagtga   5880
tctacgggca gttgcccgat ctcacccggt tttagtttca ggccctggag acccctctcc   5940
ctatgtgaca caaggaggcg aaatggcact taataaactt tcgcaaccag tgccacatcc   6000
atctgaattg attaaacccg ccactgcatg cgggcctgat ataggagtgg aaaaggacac   6060
tgtccgtgca ttgatcatgt cacgcccaat gcacccgagt tcttcagcca agctcctaag   6120
caagttagat gcagccgggt cgatcgagga aatcaggaaa atcaagcgcc ttgctctaaa   6180
tggctaattg aggattaaga aaaaatacgg gtagaatagt ttagttgata gttgtagcca   6240
cctcacttat ttttagctag ttggtggaag aaggtacgta ggtctgctag gaacttctcc   6300
attgaagtag tgttgcctgc tgccgtggga catggtgcct tgagggaggt gctgctggca   6360
ttcaggagct gacgcatgtt gaggaagaga ccctgcaggt tcttgtggca gtgctggctc   6420
tcccaaacaa ttgtggaggc tttgcataag agctcagttt tgttatttgt cttattgtct   6480
```

```
gcaaagatat ctgtcacgtt catcttgacg caggaaacct ctccctggat gtcattcact   6540
atccggatgc tctccatcag cggcactgag agctgtaagc acagcgtggg cacagcccca   6600
gggccggcca gcagcaccag cagtgccagc agggtgggca gtgaggagct catgacgtgt   6660
gtaactaccg tgtactaagc cccactcacc cagatcatca tgacacaaaa aactaatcgt   6720
tacctctctc gcttcctcag ccccactgaa tgatcgcgta accgtaatta atctagctac   6780
atttaagatt aagaaaaaat acgggtagaa ttggagtgcc ccaattgtgc caagatggac   6840
tcatctagga caattgggct gtactttgat tctgcccatt cttctagcaa cctgttagca   6900
tttccgatcg tcctacaaga cacaggagat gggaagaagc aaatcgcccc gcaatatagg   6960
atccagcgcc ttgacttgtg gactgatagt aaggaggact cagtattcat caccacctat   7020
ggattcatct ttcaagttgg gaatgaagaa gccactgtcg gcatgatcga tgataaaccc   7080
aagcgcgagt tactttccgc tgcgatgctc tgcctaggaa gcgtcccaaa taccggagac   7140
cttattgagc tggcaagggc ctgtctcact atgatagtca catgcaagaa gagtgcaact   7200
aatgctgaga gaatggtttt ctcagtagtg caggcacccc aagtgctgca aagctgtagg   7260
gttgtggcaa acaaatactc atcagtgaat gcagtcaagc acgtgaaagc gccagagaag   7320
attcccggga gtggaaccct agaatacaag gtgaactttg tctccttgac tgtggtaccg   7380
aagaaggatg tctacaagat ccctgctgca gtattgaagg tttctggctc gagtctgtac   7440
aatcttgcgc tcaatgtcac tattaatgtg gaggtagacc cgaggagtcc tttggttaaa   7500
tctctgtcta agtctgacag cggatactat gctaacctct tcttgcatat tggacttatg   7560
accaccgtag ataggaaggg gaagaaagtg acatttgaca agctggaaaa gaaaataagg   7620
agccttgatc tatctgtcgg gctcagtgat gtgctcgggc cttccgtgtt ggtaaaagca   7680
agaggtgcac ggactaagct tttggcacct ttcttctcta gcagtgggac agcctgctat   7740
cccatagcaa atgcttctcc tcaggtggcc aagatactct ggagtcaaac cgcgtgcctg   7800
cggagcgtta aaatcattat ccaagcaggt acccaacgcg ctgtcgcagt gaccgccgac   7860
cacgaggtta cctctactaa gctggagaag gggcacaccc ttgccaaata caatcctttt   7920
aagaaataag ctgcgtctct gagattgcgc tccgcccact cacccagatc atcatgacac   7980
aaaaaactaa tctgtcttga ttatttacag ttagtttacc tgtctatcaa gttagaaaaa   8040
acacgggtag aagattctgg atcccggttg gcgccctcca ggtgcaagat gggctccaga   8100
ccttctacca agaacccagc acctatgatg ctgactatcc gggttgcgct ggtactgagt   8160
tgcatctgtc cggcaaactc cattgatggc aggcctcttg cagctgcagg aattgtggtt   8220
acaggagaca aagccgtcaa catatacacc tcatcccaga caggatcaat catagttaag   8280
ctcctcccga atctgcccaa ggataaggag gcatgtgcga aagcccccct ggatgcatac   8340
aacaggacat tgaccacttt gctcaccccc cttggtgact ctatccgtag gatacaagag   8400
tctgtgacta catctggagg ggggagacag gggcgcctta taggcgccat tattggcggt   8460
gtggctcttg ggggttgcaac tgccgcacaa ataacagcgg ccgcagctct gatacaagcc   8520
aaacaaaatg ctgccaacat cctccgactt aaagagagca ttgccgcaac caatgaggct   8580
gtgcatgagg tcactgacgg attatcgcaa ctagcagtgg cagttgggaa gatgcagcag   8640
tttgttaatg accaatttaa taaaacagct caggaattag actgcatcaa aattgcacag   8700
caagttggtg tagagctcaa cctgtaccta accgaattga ctacagtatt cggaccacaa   8760
atcacttcac ctgctttaaa caagctgact attcaggcac tttacaatct agctggtgga   8820
```

```
aatatggatt acttattgac taagttaggt gtagggaaca atcaactcag ctcattaatc   8880
ggtagcggct taatcaccgg taaccctatt ctatacgact cacagactca actcttgggt   8940
atacaggtaa ctctaccttc agtcgggaac ctaaataata tgcgtgccac ctacttggaa   9000
accttatccg taagcacaac caggggattt gcctcggcac ttgtcccaaa agtggtgaca   9060
caggtcggtt ctgtgataga agaacttgac acctcatact gtatagaaac tgacttagat   9120
ttatattgta caagaatagt aacgttccct atgtcccctg gtatttattc ctgcttgagc   9180
ggcaatacgt cggcctgtat gtactcaaag accgaaggcg cacttactac accatacatg   9240
actatcaaag gttcagtcat cgccaactgc aagatgacaa catgtagatg tgtaaacccc   9300
ccgggtatca tatcgcaaaa ctatggagaa gccgtgtctc taatagataa acaatcatgc   9360
aatgttttat ccttaggcgg gataaacttta aggctcagtg gggaattcga tgtaacttat   9420
cagaagaata tctcaataca agattctcaa gtaataataa caggcaatct tgatatctca   9480
actgagcttg ggaatgtcaa caactcgatc agtaatgctt tgaataagtt agaggaaagc   9540
aacagaaaac tagacaaagt caatgtcaaa ctgactagca catctgctct cattacctat   9600
atcgttttga ctatcatatc tcttgttttt ggtatactta gcctgattct agcatgctac   9660
ctaatgtaca agcaaaaggc gcaacaaaag accttattat ggcttgggaa taatactcta   9720
gatcagatga gagccactac aaaaatgtga acacagatga ggaacgaagg tttccctaat   9780
agtaatttgt gtgaaagttc tggtagtctg tcagttcaga gagttaagaa aaaactaccg   9840
gttgtagatg accaaaggac gatatacggg tagaacggta agagaggccg cccctcaatt   9900
gcgagccagg cttcacaacc tccgttctac cgcttcaccg acaacagtcc tcaatcatgg   9960
accgcgccgt tagccaagtt gcgttagaga atgatgaaag agaggcaaaa aatacatggc  10020
gcttgatatt ccggattgca atcttattct taacagtagt gaccttggct atatctgtag  10080
cctccctttt atatagcatg ggggctagca cacctagcga tcttgtaggc ataccgacta  10140
ggatttccag ggcagaagaa aagattacat ctacacttgg ttccaatcaa gatgtagtag  10200
ataggatata taagcaagtg gcccttgagt ctccgttggc attgttaaaa actgagacca  10260
caattatgaa cgcaataaca tctctctctt atcagattaa tggagctgca acaacagtg  10320
ggtgggggc acctatccat gacccagatt atataggggg gataggcaaa gaactcattg  10380
tagatgatgc tagtgatgtc acatcattct atccctctgc atttcaagaa catctgaatt  10440
ttatcccggc gcctactaca ggatcaggtt gcactcgaat accctcattt gacatgagtg  10500
ctacccatta ctgctacacc cataatgtaa tattgtctgg atgcagagat cactcacatt  10560
catatcagta tttagcactt ggtgtgctcc ggacatctgc aacagggagg gtattctttt  10620
ctactctgcg ttccatcaac ctggacgaca cccaaaatcg gaagtcttgc agtgtgagtg  10680
caactcccct gggttgtgat atgctgtgct cgaaagtcac ggagacagag gaagaagatt  10740
ataactcagc tgtccctacg cggatggtac atgggaggtt agggttcgac ggccagtacc  10800
acgaaaagga cctagatgtc acaacattat tcggggactg ggtggccaac tacccaggag  10860
tagggggtgg atcttttatt gacagccgcg tatggttctc agtctacgga gggttaaaac  10920
ccaattcacc cagtgacact gtacaggaag ggaaatatgt gatatacaag cgatacaatg  10980
acacatgccc agatgagcaa gactaccaga ttcgaatggc caagtcttcg tataagcctg  11040
gacggtttgg tgggaaacgc atacagcagg ctatcttatc tatcaaggtg tcaacatcct  11100
taggcgaaga cccggtactg actgtaccgc ccaacacagt cacactcatg ggggccgaag  11160
gcagaattct cacagtaggg acatctcatt tcttgtatca acgagggtca tcatacttct  11220
```

-continued

```
ctcccgcgtt attatatcct atgacagtca gcaacaaaac agccactctt catagtcctt  11280
atacattcaa tgccttcact cggccaggta gtatcccttg ccaggcttca gcaagatgcc  11340
ccaacccgtg tgttactgga gtctatacag atccatatcc cctaatcttc tatagaaacc  11400
acaccttgcg aggggtattc gggacaatgc ttgatggtgt acaagcaaga cttaaccctg  11460
cgtctgcagt attcgatagc acatcccgca gtcgcattac tcgagtgagt tcaagcagta  11520
ccaaagcagc atacacaaca tcaacttgtt ttaaagtggt caagactaat aagacctatt  11580
gtctcagcat tgctgaaata tctaatactc tcttcggaga attcagaatc gtcccgttac  11640
tagttgagat cctcaaagat gacggggtta gagaagccag gtctggctag ttgagtcaat  11700
tataaaggag ttggaaagat ggcattgtat cacctatctt ctgcgacatc aagaatcaaa  11760
ccgaatgccg gcgcgtgctc gaattccatg ttgccagttg accacaatca gccagtgctc  11820
atgcgatcag attaagcctt gtcaatagtc tcttgattaa gaaaaaatgt aagtggcaat  11880
gagatacaag gcaaaacagc tcatggtaaa taatacgggt aggacatggc gagctccggt  11940
cctgaaaggg cagagcatca gattatccta ccagagtcac acctgtcttc accattggtc  12000
aagcacaaac tactctatta ctggaaatta actgggctac cgcttcctga tgaatgtgac  12060
ttcgaccacc tcattctcag ccgacaatgg aaaaaaatac ttgaatcggc ctctcctgat  12120
actgagagaa tgatagaact cggaagggca gtacaccaaa ctcttaacca caattccaga  12180
ataaccggag tgctccaccc caggtgttta gaagaactgg ctaatattga ggtcccagat  12240
tcaaccaaca aatttcggaa gattgagaag aagatccaaa ttcacaacac gagatatgga  12300
gaactgttca caaggctgtg tacgcatata gagaagaaac tgctggggtc atcttggtct  12360
aacaatgtcc cccggtcaga ggagttcagc agcattcgta cggatccggc attctggttt  12420
cactcaaaat ggtccacagc caagtttgca tggctccata taaaacagat ccagaggcat  12480
ctgatggtgg cagctaggac aaggtctgcg gccaacaaat tggtgatgct aacccataag  12540
gtaggccaag tctttgtcac tcctgaactt gtcgttgtga cgcatacgaa tgagaacaag  12600
ttcacatgtc ttacccagga acttgtattg atgtatgcag atatgatgga gggcagagat  12660
atggtcaaca taatatcaac cacggcggtg catctcagaa gcttatcaga gaaaattgat  12720
gacattttgc ggttaataga cgctctggca aaagacttgg gtaatcaagt ctacgatgtt  12780
gtatcactaa tggagggatt tgcatacgga gctgtccagc tactcgagcc gtcaggtaca  12840
tttgcaggag atttcttcgc attcaacctg caggagctta aagacattct aattggcctc  12900
ctccccaatg atatagcaga atccgtgact catgcaatcg ctactgtatt ctctggttta  12960
gaacagaatc aagcagctga gatgttgtgt ctgttgcgtc tgtggggtca cccactgctt  13020
gagtcccgta ttgcagcaaa ggcagtcagg agccaaatgt gcgcaccgaa aatggtagac  13080
tttgatatga tccttcaggt actgtctttc ttcaagggaa caatcatcaa cgggtacaga  13140
aagaagaatg caggtgtgtg gccgcgagtc aaagtggata caatatatgg gaaggtcatt  13200
gggcaactac atgcagattc agcagagatt tcacacgata tcatgttgag agagtataag  13260
agtttatctg cacttgaatt tgagccatgt atagaatatg accctgtcac caacctgagc  13320
atgttcctaa aagacaaggc aatcgcacac cccaacgata attggcttgc ctcgtttagg  13380
cggaaccttc tctccgaaga ccagaagaaa catgtaaaag aagcaacttc gactaatcgc  13440
ctcttgatag agtttttaga gtcaaatgat tttgatccat ataaagagat ggaatatctg  13500
acgacccttg agtaccttag agatgacaat gtggcagtat catactcgct caaggagaag  13560
```

-continued gaagtgaaag ttaatggacg gatcttcgct aagctgacaa agaagttaag gaactgtcag 13620
gtgatggcgg aagggatcct agccgatcag attgcacctt tctttcaggg aaatggagtc 13680
attcaggata gcatatcctt gaccaagagt atgctagcga tgagtcaact gtcttttaac 13740
agcaataaga aacgtatcac tgactgtaaa gaaagagtat cttcaaaccg caatcatgat 13800
ccgaaaagca agaaccgtcg gagagttgca accttcataa caactgacct gcaaaagtac 13860
tgtcttaatt ggagatatca gacgatcaaa ttgttcgctc atgccatcaa tcagttgatg 13920
ggcctacctc atttcttcga gtggattcac ctaagactga tggacactac gatgttcgta 13980
ggagaccctt tcaatcctcc aagtgaccct actgactgtg acctctcaag agtccctaat 14040
gatgacatat atattgtcag tgccagaggg ggtatcgaag gattatgcca gaagctatgg 14100
acaatgatct caattgctgc aatccaactt gctgcagcta gatcgcattg tcgtgttgcc 14160
tgtatggtac agggtgataa tcaagtaata gcagtaacga gagaggtaag atcagatgac 14220
tctccggaga cggtgttgac acagttgcat caagccagtg ataatttctt caaggaatta 14280
atccatgtca atcatttgat tggccataat ttgaaggatc gtgaaaccat caggtcagac 14340
acattcttca tatacagcaa acgaatcttc aaagatggag caatcctcag tcaagtcctc 14400
aaaaattcat ctaaattagt gctagtgtca ggtgatctca gtgaaaacac tgtaatgtcc 14460
tgtgccaaca ttgcctctac tgtagcacgg ctatgcgaga acgggcttcc caaagacttc 14520
tgttactatt taaactatat aatgagttgt gtgcagacat actttgactc tgagttctcc 14580
atcaccaaca attcgcaccc cgatcttaat cagtcgtgga ttgaggacat ctcttttgtg 14640
cactcatatg ttctgactcc tgcccaatta gggggactga gtaaccttca atactcaagg 14700
ctctacacta gaaatatcgg tgacccgggg actactgctt ttgcagagat caagcgacta 14760
gaagcagtgg gattactgag tcctaacatt atgactaata tcttaactag gccgcctggg 14820
aatggagatt gggccagtct gtgcaacgac ccatactctt tcaattttga gactgttgca 14880
agcccaaata ttgttcttaa gaaacatacg caaagagtcc tatttgaaac ttgttcaaat 14940
cccttattgt ctggagtgca cacagaggat aatgaggcag aagagaaggc attggctgaa 15000
ttcttgctta atcaagaggt gattcatccc cgcgttgcgc atgccatcat ggaggcaagc 15060
tctgtaggta ggagaaagca aattcaaggg cttgttgaca caacaaacac cgtaattaag 15120
attgcgctta ctaggaggcc attaggcatc aagaggctga tgcggatagt caattattct 15180
agcatgcatg caatgctgtt tagagacgat gtttttcct ccagtagatc caaccacccc 15240
ttagtctctt ctaatatgtg ttctctgaca ctggcagact atgcacggaa tagaagctgg 15300
tcacctttga cgggaggcag gaaaatactg ggtgtatcta atcctgatac gatagaactc 15360
gtagagggtg agattcttag tgtaagcgga gggtgtacaa gatgtgacag cggagatgaa 15420
caatttactt ggttccatct tccaagcaat atagaattga ccgatgacac cagcaagaat 15480
cctccgatga gggtaccata tctcgggtca aagacacagg agaggagagc tgcctcactt 15540
gcaaaaatag ctcatatgtc gccacatgta aaggctgccc taagggcatc atccgtgttg 15600
atctgggctt atggggataa tgaagtaaat tggactgctg ctcttacgat tgcaaaatct 15660
cggtgcaatg taaacttaga gtatcttcgg ttactgtccc ctttacccac ggctgggaat 15720
cttcaacata gactagatga tggtataact cagatgacat tcacccctgc atctctctac 15780
agggtgtcac cttacattca catatccaat gattctcaaa ggctgttcac tgaagaagga 15840
gtcaaagagg ggaatgtggt ttaccaacag atcatgctct tgggtttatc tctaatcgaa 15900
tcgatctttc caatgacaac aaccaggaca tatgatgaga tcacactgca cctacatagt 15960

-continued

```
aaatttagtt gctgtatcag agaagcacct gttgcggttc ctttcgagct acttggggtg  16020
gtaccggaac tgaggacagt gacctcaaat aagtttatgt atgatcctag ccctgtatcg  16080
gagggagact ttgcgagact tgacttagct atcttcaaga gttatgagct taatctggag  16140
tcatatccca cgatagagct aatgaacatt ctttcaatat ccagcgggaa gttgattggc  16200
cagtctgtgg tttcttatga tgaagatacc tccataaaga atgatgccat aatagtgtat  16260
gacaataccc gaaattggat cagtgaagct cagaattcag atgtggtccg cctatttgaa  16320
tatgcagcac ttgaagtgct cctcgactgt tcttaccaac tctattacct gagagtaaga  16380
ggcctagaca atattgtctt atatatgggt gatttataca agaatatgcc aggaattcta  16440
ctttccaaca ttgcagctac aatatctcat cctgtcattc attcaaggtt acatgcagtg  16500
ggcctggtca accatgacgg atcacaccaa cttgcagata cggattttat cgaaatgtct  16560
gcaaaactgt tagtatcttg cacccgacgt gtgatctccg gcttatattc aggaaataag  16620
tatgatctgc tgttcccatc tgtcttagat gataacctga atgagaagat gcttcagctg  16680
atatcccggt tatgctgtct gtacacggta ctctttgcta caacaagaga aatcccgaaa  16740
ataagaggct taactgcaga agagaaatgt tcaatactca ctgagtattt actgtcggat  16800
gctgtgaaac cattacttag ccccgatcaa gtgagctcta tcatgtctcc taacataatt  16860
acattcccag ctaatctgta ctacatgtct cggaagagcc tcaatttgat cagggaaagg  16920
gaggacaggg atactatcct ggcgttgttg ttcccccaag agccattatt agagttccct  16980
tctgtgcaag atattggtgc tcgagtgaaa gatccattca cccgacaacc tgcggcattt  17040
ttgcaagagt tagatttgag tgctccagca aggtatgacg cattcacact tagtcagatt  17100
catcctgaac tcacatctcc aaatccggag gaagactact tagtacgata cttgttcaga  17160
gggataggga ctgcatcttc ctcttggtat aaggcatccc atctcctttc tgtacccgag  17220
gtaagatgtg caagacacgg gaactcctta tacttggctg aaggaagcgg agccatcatg  17280
agtcttcttg aactgcatgt accacatgaa actatctatt acaatacgct cttttcaaat  17340
gagatgaacc ccccgcaacg acatttcggg ccgaccccaa ctcagttttt gaattcggtt  17400
gtttatagga atctacaggc ggaggtaaca tgcaaggatg gatttgtcca agagttccgt  17460
ccattatgga gagaaaatac agaggaaagt gacctgacct cagataaagc agtggggtat  17520
attacatctg cagtacccta cagatctgta tcattgctgc attgtgacat tgaaattcct  17580
ccagggtcca atcaaagctt actagatcaa ctagctatca atttatctct gattgccatg  17640
cattctgtaa gggagggcgg ggtagtaatc atcaaagtgt tgtatgcaat gggatactac  17700
tttcatctac tcatgaactt gtttgctccg tgttccacaa aaggatatat tctctctaat  17760
ggttatgcat gtcgagggga tatggagtgt tacctggtat ttgtcatggg ttacctgggc  17820
gggcctacat ttgtacatga ggtggtgagg atggcaaaaa ctctggtgca gcggcacggt  17880
acgcttttgt ctaaatcaga tgagatcaca ctgaccaggt tattcacctc acagcggcag  17940
cgtgtgacag acatcctatc cagtccttta ccaagattaa taaagtactt gaggaagaat  18000
attgacactg cgctgattga agccgggga cagcccgtcc gtccattctg tgcggagagt  18060
ctggtgagca cgctagcgaa cataactcag ataacccaga tcatcgctag ccacattgac  18120
acagttatcc ggtctgtgat atatatggaa gctgagggtg atctcgctga cacagtattt  18180
ctatttaccc cttacaatct ctctactgac gggaaaaaga ggacatcact taaacagtgc  18240
acgagacaga tcctagaggt tacaatacta ggtcttagag tcgaaaatct caataaaata  18300
```

```
ggcgatataa tcagcctagt gcttaaaggc atgatctcca tggaggacct tatcccacta  18360

aggacatact tgaagcatag tacctgccct aaatatttga aggctgtcct aggtattacc  18420

aaactcaaag aaatgtttac agacacttct gtactgtact tgactcgtgc tcaacaaaaa  18480

ttctacatga aaactatagg caatgcagtc aaaggatatt acagtaactg tgactcctaa  18540

cgaaaatcac atattaatag gctccttttt tggccaattg tattcttgtt gatttaatta  18600

tattatgtta gaaaaaagtt gaactctgac tccttaggac tcgaattcga actcaaataa  18660

atgtctttaa aaaaggttgc gcacaattat tcttgagtgt agtctcgtca ttcaccaaat  18720

ctttgtttgg tggccggcat ggtcccagcc tcctcgct                          18758
```

<210> SEQ ID NO 25
<211> LENGTH: 15618
<212> TYPE: DNA
<213> ORGANISM: Artificial Sequence
<220> FEATURE:
<223> OTHER INFORMATION: chemically synthesized

<400> SEQUENCE: 25

```
accaaacaga gaatccgtga gtcgcgataa aaggcgaaag agcaattgaa gtcacacggg     60

tagaaggtgt gaatctcgag tgcgagcccg aagcacaaac tcgagaaagc cttctgccaa    120

catgtcttcc gtatttgatg agtacgaaca gctcctcgcg gctcagactc gccccaatgg    180

agctcatgga gggggagaaa aagggagtac cttaaaagta gacgtcccgg tattcactct    240

taacagtgat gacccagaag atagatggag ctttgtggta ttctgcctcc ggattgctgt    300

tagcgaagat gccaacaaac cactcaggca aggtgctctc atatctcttt tatgctccca    360

ctcacaggta atgaggaacc atgttgccct tgcagggaaa cagaatgaag ccacattggc    420

cgtgcttgag attgatggct ttgccaacgg cacgccccag ttcaacaata ggagtggagt    480

gtctgaagag agagcacaga gatttgcgat gatagcagga tctctccctc gggcatgcag    540

caacggaacc ccgttcgtca cagccggggc cgaagatgat gcaccagaag acatcaccga    600

taccctggat aggatcctct ctatccaggc tcaagtatgg gtcacagtag caaaagccat    660

gactgcgtat gagactgcag atgagtcgga aacaaggcga atcaataagt atatgcagca    720

aggcagggtc caaaagaaat acatcctcta ccccgtatgc aggagcacaa tccaactcac    780

gatcagacag tctcttgcag tccgcatctt tttggttagc gagctcaaga gaggccgcaa    840

cacggcaggt ggtacctcta cttattataa cctggtaggg gacgtagact catacatcag    900

gaataccggg cttactgcat tcttcttgac actcaagtac ggaatcaaca ccaagacatc    960

agcccttgca cttagtagcc tctcaggcga catccagaag atgaagcagc tcatgcgttt   1020

gtatcggatg aaaggagata atgcgccgta catgacatta cttggtgata gtgaccagat   1080

gagctttgcg cctgccgagt atgcacaact ttactccttt gccatgggta tggcatcagt   1140

cctagataaa ggtactggga aataccaatt tgccagggac tttatgagca catcattctg   1200

gagacttgga gtagagtacg ctcaggctca gggaagtagc attaacgagg atatggctgc   1260

cgagctaaag ctaaccccag cagcaaggag gggcctggca gctgctgccc aacgggtctc   1320

cgaggagacc agcagcatag acatgcctac tcaacaagtc ggagtcctca ctgggcttag   1380

cgaggggggg tcccaagctc tacaaggcgg atcgaataga tcgcaagggc aaccagaagc   1440

cggggatggg gagacccaat tcctggatct gatgagagcg gtagcaaata gcatgaggga   1500

ggcgccaaac tctgcacagg gcactcccca atcggggcct cccccaactc ctgggccatc   1560

ccaagataac gacaccgact gggggtattg atggacaaaa cccagcctgc ttccacaaaa   1620
```

-continued acatcccaat gccctcaccc gtagtcgacc cctcgatttg cggctctata tgaccacacc 1680
ctcaaacaaa catccccctc tttcctccct ccccctgctg tacaactccg cacgccctag 1740
ataccacagg cacaatgcgg ctcactaaca atcaaaacag agccgaggga attagaaaaa 1800
agtacgggta gaagagggat attcagagat cagggcaagt ctcccgagtc tctgctctct 1860
cctctacctg atagaccagg acaaacatgg ccacctttac agatgcagag atcgacgagc 1920
tatttgagac aagtggaact gtcattgaca acataattac agcccagggt aaaccagcag 1980
agactgttgg aaggagtgca atcccacaag gcaagaccaa ggtgctgagc gcagcatggg 2040
agaagcatgg gagcatccag ccaccggcca gtcaaggcaa ccccgatcga caggacagat 2100
ctgacaaaca accatccaca cccgggcaaa cgaccccgca tgacagcccg ccggccacat 2160
ccgccgacca gcccccccacc caggccacag acgaagccgt cgacacacag ctcaggaccg 2220
gagcaagcaa ctctctgctg ttgatgcttg acaagctcag caataaatcg tccaatgcta 2280
aaaagggccc atggtcgagc cccaagaggg ggaatcacca acgtccgact caacagcagg 2340
ggagtcaacc cagtcgcgga aacagtcagg aaagaccgca gaaccaagtc aaggccgccc 2400
ctggaaacca gggcacagac gtgaacacag catatcatgg acaatgggag gagtcacaac 2460
tatcagctgg tgcaacccct catgctctcc gatcaaggca gagccaagac aataccccttg 2520
tatctgcgga tcatgtccag ccacctgtag actttgtgca agcgatgatg tctatgatgg 2580
aggcgatatc acagagagta agtaaggtcg actatcagct agatcttgtc ttgaaacaga 2640
catcctccat ccctatgatg cggtccgaaa tccaacagct gaaaacatct gttgcagtca 2700
tggaagccaa cttgggaatg atgaagattc tggatcccgg ttgtgccaac atttcatctc 2760
tgagtgatct acgggcagtt gcccgatctc acccggtttt agtttcaggc cctggagacc 2820
cctctcccta tgtgacacaa ggaggcgaaa tggcacttaa taaactttcg caaccagtgc 2880
cacatccatc tgaattgatt aaacccgcca ctgcatgcgg gcctgatata ggagtggaaa 2940
aggacactgt ccgtgcattg atcatgtcac gcccaatgca cccgagttct tcagccaagc 3000
tcctaagcaa gttagatgca gccgggtcga tcgaggaaat caggaaaatc aagcgccttg 3060
ctctaaatgg ctaattgagg attaagaaaa aatacgggta gaatagttta gttgatagtt 3120
gtagccacct cacttatttt tagctagttg gtggaagaag gtacgtaggt ctgctaggaa 3180
cttctccatt gaagtagtgt tgcctgctgc cgtgggacat ggtgccttga gggaggtgct 3240
gctggcattc aggagctgac gcatgttgag gaagagaccc tgcaggttct tgtggcagtg 3300
ctggctctcc caaacaattg tggaggcttt gcataagagc tcagttttgt tatttgtctt 3360
attgtctgca aagatatctg tcacgttcat cttgacgcag gaaacctctc cctggatgtc 3420
attcactatc cggatgctct ccatcagcgg cactgagagc tgtaagcaca gcgtgggcac 3480
agccccaggg ccggccagca gcaccagcag tgccagcagg gtgggcagtg aggagctcat 3540
gacgtgtgta actaccgtgt actaagcccc actcacccag atcatcatga cacaaaaaac 3600
taatcgttac ctctctcgct tcctcagccc cactgaatga tcgcgtaacc gtaattaatc 3660
tagctacatt taagattaag aaaaaatacg ggtagaattg gagtgcccca attgtgccaa 3720
gatggactca tctaggacaa ttgggctgta ctttgattct gcccattctt ctagcaacct 3780
gttagcattt ccgatcgtcc tacaagacac aggagatggg aagaagcaaa tcgccccgca 3840
atataggatc cagcgccttg acttgtggac tgatagtaag gaggactcag tattcatcac 3900
cacctatgga ttcatctttc aagttgggaa tgaagaagcc actgtcggca tgatcgatga 3960

-continued

```
taaacccaag cgcgagttac tttccgctgc gatgctctgc ctaggaagcg tcccaaatac   4020
cggagacctt attgagctgg caagggcctg tctcactatg atagtcacat gcaagaagag   4080
tgcaactaat gctgagagaa tggtttttctc agtagtgcag gcaccccaag tgctgcaaag   4140
ctgtagggtt gtggcaaaca aatactcatc agtgaatgca gtcaagcacg tgaaagcgcc   4200
agagaagatt cccgggagtg gaaccctaga atacaaggtg aactttgtct ccttgactgt   4260
ggtaccgaag aaggatgtct acaagatccc tgctgcagta ttgaaggttt ctggctcgag   4320
tctgtacaat cttgcgctca atgtcactat taatgtggag gtagacccga ggagtccttt   4380
ggttaaatct ctgtctaagt ctgacagcgg atactatgct aacctcttct tgcatattgg   4440
acttatgacc accgtagata ggaaggggaa gaaagtgaca tttgacaagc tggaaaagaa   4500
aataaggagc cttgatctat ctgtcgggct cagtgatgtg ctcgggcctt ccgtgttggt   4560
aaaagcaaga ggtgcacgga ctaagctttt ggcacctttc ttctctagca gtgggacagc   4620
ctgctatccc atagcaaatg cttctcctca ggtggccaag atactctgga gtcaaaccgc   4680
gtgcctgcgg agcgttaaaa tcattatcca agcaggtacc caacgcgctg tcgcagtgac   4740
cgccgaccac gaggttacct ctactaagct ggagaagggg cacacccttg ccaaatacaa   4800
tcctttttaag aaataagctg cgtctctgag attgcgctcc gcccactcac ccagatcatc   4860
atgacacaaa aaactaatct gtcttgatta tttacagtta gtttacctgt ctatcaagtt   4920
agaaaaaaca cgggtagaag attctggatc ccggttggcg ccctccaggt gcaagatggg   4980
ctccagacct tctaccaaga acccagcacc tatgatgctg actatccggg ttgcgctggt   5040
actgagttgc atctgtccgg caaactccat tgatggcagg cctcttgcag ctgcaggaat   5100
tgtggttaca ggagacaaag ccgtcaacat atacacctca tcccagacag gatcaatcat   5160
agttaagctc ctcccgaatc tgcccaagga taaggaggca tgtgcgaaag ccccccttgga   5220
tgcatacaac aggacattga ccactttgct caccccccctt ggtgactcta tccgtaggat   5280
acaagagtct gtgactacat ctggaggggg gagacagggg cgccttatag gcgccattat   5340
tggcggtgtg gctcttgggg ttgcaactgc cgcacaaata acagcggccg cagctctgat   5400
acaagccaaa caaaatgctg ccaacatcct ccgacttaaa gagagcattg ccgcaaccaa   5460
tgaggctgtg catgaggtca ctgacggatt atcgcaacta gcagtggcag ttgggaagat   5520
gcagcagttt gttaatgacc aatttaataa aacagctcag gaattagact gcatcaaaat   5580
tgcacagcaa gttggtgtag agctcaacct gtacctaacc gaattgacta cagtattcgg   5640
accacaaatc acttcacctg ctttaaacaa gctgactatt caggcacttt acaatctagc   5700
tggtggaaat atggattact tattgactaa gttaggtgta gggaacaatc aactcagctc   5760
attaatcggt agcggcttaa tcaccggtaa ccctattcta tacgactcac agactcaact   5820
cttgggtata caggtaactc taccttcagt cgggaaccta aataatatgc gtgccaccta   5880
cttggaaacc ttatccgtaa gcacaaccag gggatttgcc tcggcacttg tcccaaaagt   5940
ggtgacacag gtcggttctg tgatagaaga acttgacacc tcatactgta tagaaactga   6000
cttagattta tattgtacaa gaatagtaac gttccctatg tcccctggta tttattcctg   6060
cttgagcggc aatacgtcgg cctgtatgta ctcaaagacc gaaggcgcac ttactacacc   6120
atacatgact atcaaaggtt cagtcatcgc caactgcaag atgacaacat gtagatgtgt   6180
aaaccccccg ggtatcatat cgcaaaacta tggagaagcc gtgtctctaa tagataaaca   6240
atcatgcaat gttttatcct taggcgggat aactttaagg ctcagtgggg aattcgatgt   6300
aacttatcag aagaatatct caatacaaga ttctcaagta ataataacag gcaatcttga   6360
```

tatctcaact gagcttggga atgtcaacaa ctcgatcagt aatgctttga ataagttaga 6420
ggaaagcaac agaaaactag acaaagtcaa tgtcaaactg actagcacat ctgctctcat 6480
tacctatatc gttttgacta tcatatctct tgtttttggt atacttagcc tgattctagc 6540
atgctaccta atgtacaagc aaaaggcgca acaaaagacc ttattatggc ttgggaataa 6600
tactctagat cagatgagag ccactacaaa aatgtgaaca cagatgagga acgaaggttt 6660
ccctaatagt aatttgtgtg aaagttctgg tagtctgtca gttcagagag ttaagaaaaa 6720
actaccggtt gtagatgacc aaaggacgat atacgggtag aacggtaaga gaggccgccc 6780
ctcaattgcg agccaggctt cacaacctcc gttctaccgc ttcaccgaca acagtcctca 6840
atcatggacc gcgccgttag ccaagttgcg ttagagaatg atgaaagaga ggcaaaaaat 6900
acatggcgct tgatattccg gattgcaatc ttattcttaa cagtagtgac cttggctata 6960
tctgtagcct ccctttata tagcatgggg gctagcacac ctagcgatct tgtaggcata 7020
ccgactagga tttccagggc agaagaaaag attacatcta cacttggttc caatcaagat 7080
gtagtagata ggatatataa gcaagtggcc cttgagtctc cgttggcatt gttaaaaact 7140
gagaccacaa ttatgaacgc aataacatct ctctcttatc agattaatgg agctgcaaac 7200
aacagtgggt gggggcacc tatccatgac ccagattata tagggggat aggcaaagaa 7260 ctcattgtag atgatgctag tgatgtcaca tcattctatc cctctgcatt tcaagaacat 7320
ctgaatttta tcccggcgcc tactacagga tcaggttgca ctcgaatacc ctcatttgac 7380
atgagtgcta cccattactg ctacacccat aatgtaatat tgtctggatg cagagatcac 7440
tcacattcat atcagtattt agcacttggt gtgctccgga catctgcaac agggagggta 7500
ttcttttcta ctctgcgttc catcaacctg gacgacaccc aaaatcggaa gtcttgcagt 7560
gtgagtgcaa ctcccctggg ttgtgatatg ctgtgctcga aagtcacgga gacagaggaa 7620
gaagattata actcagctgt ccctacgcgg atggtacatg ggaggttagg gttcgacggc 7680
cagtaccacg aaaaggacct agatgtcaca acattattcg gggactgggt ggccaactac 7740
ccaggagtag gggtggatc ttttattgac agccgcgtat ggttctcagt ctacggaggg 7800
ttaaaaccca attcacccag tgacactgta caggaaggga aatatgtgat atacaagcga 7860
tacaatgaca catgcccaga tgagcaagac taccagattc gaatggccaa gtcttcgtat 7920
aagcctggac ggtttggtgg gaaacgcata cagcaggcta tcttatctat caaggtgtca 7980
acatccttag gcgaagaccc ggtactgact gtaccgccca acacagtcac actcatgggg 8040
gccgaaggca gaattctcac agtagggaca tctcatttct tgtatcaacg agggtcatca 8100
tacttctctc ccgcgttatt atatcctatg acagtcagca acaaaacagc cactcttcat 8160
agtccttata cattcaatgc cttcactcgg ccaggtagta tcccttgcca ggcttcagca 8220
agatgcccca acccgtgtgt tactggagtc tatacagatc catatcccct aatcttctat 8280
agaaaccaca ccttgcgagg ggtattcggg acaatgcttg atggtgtaca agcaagactt 8340
aaccctgcgt ctgcagtatt cgatagcaca tcccgcagtc gcattactcg agtgagttca 8400
agcagtacca aagcagcata cacaacatca acttgtttta aagtggtcaa gactaataag 8460
acctattgtc tcagcattgc tgaaatatct aatactctct tcggagaatt cagaatcgtc 8520
ccgttactag ttgagatcct caaagatgac ggggttagag aagccaggtc tggctagttg 8580
agtcaattat aaaggagttg gaaagatggc attgtatcac ctatcttctg cgacatcaag 8640
aatcaaaccg aatgccggcg cgtgctcgaa ttccatgttg ccagttgacc acaatcagcc 8700

-continued agtgctcatg cgatcagatt aagccttgtc aatagtctct tgattaagaa aaaatgtaag 8760
tggcaatgag atacaaggca aaacagctca tggtaaataa tacgggtagg acatggcgag 8820
ctccggtcct gaaagggcag agcatcagat tatcctacca gagtcacacc tgtcttcacc 8880
attggtcaag cacaaactac tctattactg gaaattaact gggctaccgc ttcctgatga 8940
atgtgacttc gaccacctca ttctcagccg acaatggaaa aaaatacttg aatcggcctc 9000
tcctgatact gagagaatga tagaactcgg aagggcagta caccaaactc ttaaccacaa 9060
ttccagaata accggagtgc tccaccccag gtgtttagaa gaactggcta atattgaggt 9120
cccagattca accaacaaat ttcggaagat tgagaagaag atccaaattc acaacacgag 9180
atatggagaa ctgttcacaa ggctgtgtac gcatatagag aagaaactgc tggggtcatc 9240
ttggtctaac aatgtccccc ggtcagagga gttcagcagc attcgtacgg atccggcatt 9300
ctggtttcac tcaaaatggt ccacagccaa gtttgcatgg ctccatataa aacagatcca 9360
gaggcatctg atggtggcag ctaggacaag gtctgcggcc aacaaattgg tgatgctaac 9420
ccataaggta ggccaagtct ttgtcactcc tgaacttgtc gttgtgacgc atacgaatga 9480
gaacaagttc acatgtctta cccaggaact tgtattgatg tatgcagata tgatggaggg 9540
cagagatatg gtcaacataa tatcaaccac ggcggtgcat ctcagaagct tatcagagaa 9600
aattgatgac attttgcggt taatagacgc tctggcaaaa gacttgggta atcaagtcta 9660
cgatgttgta tcactaatgg agggatttgc atacggagct gtccagctac tcgagccgtc 9720
aggtacattt gcaggagatt tcttcgcatt caacctgcag gagcttaaag acattctaat 9780
tggcctcctc cccaatgata tagcagaatc cgtgactcat gcaatcgcta ctgtattctc 9840
tggtttagaa cagaatcaag cagctgagat gttgtgtctg ttgcgtctgt ggggtcaccc 9900
actgcttgag tcccgtattg cagcaaaggc agtcaggagc caaatgtgcg caccgaaaat 9960
ggtagacttt gatatgatcc ttcaggtact gtctttcttc aagggaacaa tcatcaacgg 10020
gtacagaaag aagaatgcag gtgtgtggcc gcgagtcaaa gtggatacaa tatatgggaa 10080
ggtcattggg caactacatg cagattcagc agagatttca cacgatatca tgttgagaga 10140
gtataagagt ttatctgcac ttgaatttga gccatgtata gaatatgacc ctgtcaccaa 10200
cctgagcatg ttcctaaaag acaaggcaat cgcacacccc aacgataatt ggcttgcctc 10260
gtttaggcgg aaccttctct ccgaagacca gaagaaacat gtaaaagaag caacttcgac 10320
taatcgcctc ttgatagagt ttttagagtc aaatgatttt gatccatata aagagatgga 10380
atatctgacg acccttgagt accttagaga tgacaatgtg gcagtatcat actcgctcaa 10440
ggagaaggaa gtgaaagtta atggacggat cttcgctaag ctgacaaaga agttaaggaa 10500
ctgtcaggtg atggcggaag ggatcctagc cgatcagatt gcacctttct ttcagggaaa 10560
tggagtcatt caggatagca tatccttgac caagagtatg ctagcgatga gtcaactgtc 10620
ttttaacagc aataagaaac gtatcactga ctgtaaagaa agagtatctt caaaccgcaa 10680
tcatgatccg aaaagcaaga accgtcggag agttgcaacc ttcataacaa ctgacctgca 10740
aaagtactgt cttaattgga gatatcagac gatcaaattg ttcgctcatg ccatcaatca 10800
gttgatgggc ctacctcatt tcttcgagtg gattcaccta agactgatgg acactacgat 10860
gttcgtagga gacccttca atcctccaag tgaccctact gactgtgacc tctcaagagt 10920
ccctaatgat gacatatata ttgtcagtgc cagagggggt atcgaaggat tatgccagaa 10980
gctatggaca atgatctcaa ttgctgcaat ccaacttgct gcagctagat cgcattgtcg 11040
tgttgcctgt atggtacagg gtgataatca agtaatagca gtaacgagag aggtaagatc 11100
agatgactct ccggagacgg tgttgacaca gttgcatcaa gccagtgata atttcttcaa 11160
ggaattaatc catgtcaatc atttgattgg ccataatttg aaggatcgtg aaaccatcag 11220
gtcagacaca ttcttcatat acagcaaacg aatcttcaaa gatggagcaa tcctcagtca 11280
agtcctcaaa aattcatcta aattagtgct agtgtcaggt gatctcagtg aaaacactgt 11340
aatgtcctgt gccaacattg cctctactgt agcacggcta tgcgagaacg ggcttcccaa 11400
agacttctgt tactatttaa actatataat gagttgtgtg cagacatact ttgactctga 11460
gttctccatc accaacaatt cgcaccccga tcttaatcag tcgtggattg aggacatctc 11520
ttttgtgcac tcatatgttc tgactcctgc ccaattaggg ggactgagta accttcaata 11580
ctcaaggctc tacactagaa atatcggtga cccggggact actgcttttg cagagatcaa 11640
gcgactagaa gcagtgggat tactgagtcc taacattatg actaatatct taactaggcc 11700
gcctgggaat ggagattggg ccagtctgtg caacgaccca tactctttca attttgagac 11760
tgttgcaagc ccaaatattg ttcttaagaa acatacgcaa agagtcctat ttgaaacttg 11820
ttcaaatccc ttattgtctg gagtgcacac agaggataat gaggcagaag agaaggcatt 11880
ggctgaattc ttgcttaatc aagaggtgat tcatccccgc gttgcgcatg ccatcatgga 11940
ggcaagctct gtaggtagga gaaagcaaat tcaagggctt gttgacacaa caaacaccgt 12000
aattaagatt gcgcttacta ggaggccatt aggcatcaag aggctgatgc ggatagtcaa 12060
ttattctagc atgcatgcaa tgctgtttag agacgatgtt ttttcctcca gtagatccaa 12120
ccacccctta gtctcttcta atatgtgttc tctgacactg gcagactatg cacggaatag 12180
aagctggtca cctttgacgg gaggcaggaa aatactgggt gtatctaatc ctgatacgat 12240
agaactcgta gagggtgaga ttcttagtgt aagcggaggg tgtacaagat gtgacagcgg 12300
agatgaacaa tttacttggt tccatcttcc aagcaatata gaattgaccg atgacaccag 12360
caagaatcct ccgatgaggg taccatatct cgggtcaaag acacaggaga ggagagctgc 12420
ctcacttgca aaaatagctc atatgtcgcc acatgtaaag gctgccctaa gggcatcatc 12480
cgtgttgatc tgggcttatg gggataatga agtaaattgg actgctgctc ttacgattgc 12540
aaaatctcgg tgcaatgtaa acttagagta tcttcggtta ctgtcccctt tacccacggc 12600
tgggaatctt caacatagac tagatgatgg tataactcag atgacattca cccctgcatc 12660
tctctacagg gtgtcacctt acattcacat atccaatgat tctcaaaggc tgttcactga 12720
agaaggagtc aaagagggga atgtggttta ccaacagatc atgctcttgg gtttatctct 12780
aatcgaatcg atctttccaa tgacaacaac caggacatat gatgagatca cactgcacct 12840
acatagtaaa tttagttgct gtatcagaga agcacctgtt gcggttcctt tcgagctact 12900
tggggtggta ccggaactga ggacagtgac ctcaaataag tttatgtatg atcctagccc 12960
tgtatcggag ggagactttg cgagacttga cttagctatc ttcaagagtt atgagcttaa 13020
tctggagtca tatcccacga tagagctaat gaacattctt tcaatatcca gcgggaagtt 13080
gattggccag tctgtggttt cttatgatga agatacctcc ataaagaatg atgccataat 13140
agtgtatgac aatacccgaa attggatcag tgaagctcag aattcagatg tggtccgcct 13200
atttgaatat gcagcacttg aagtgctcct cgactgttct taccaactct attacctgag 13260
agtaagaggc ctagacaata ttgtcttata tatgggtgat ttatacaaga atatgccagg 13320
aattctactt tccaacattg cagctacaat atctcatcct gtcattcatt caaggttaca 13380
tgcagtgggc ctggtcaacc atgacggatc acaccaactt gcagatacgg attttatcga 13440

-continued

```
aatgtctgca aaactgttag tatcttgcac ccgacgtgtg atctccggct tatattcagg  13500
aaataagtat gatctgctgt tcccatctgt cttagatgat aacctgaatg agaagatgct  13560
tcagctgata tcccggttat gctgtctgta cacggtactc tttgctacaa caagagaaat  13620
cccgaaaata agaggcttaa ctgcagaaga gaaatgttca atactcactg agtatttact  13680
gtcggatgct gtgaaaccat tacttagccc cgatcaagtg agctctatca tgtctcctaa  13740
cataattaca ttcccagcta atctgtacta catgtctcgg aagagcctca atttgatcag  13800
ggaaagggag gacagggata ctatcctggc gttgttgttc ccccaagagc cattattaga  13860
gttcccttct gtgcaagata ttggtgctcg agtgaaagat ccattcaccc gacaacctgc  13920
ggcatttttg caagagttag atttgagtgc tccagcaagg tatgacgcat tcacacttag  13980
tcagattcat cctgaactca catctccaaa tccggaggaa gactacttag tacgatactt  14040
gttcagaggg atagggactg catcttcctc ttggtataag gcatcccatc tcctttctgt  14100
acccgaggta agatgtgcaa gacacgggaa ctccttatac ttggctgaag gaagcggagc  14160
catcatgagt cttcttgaac tgcatgtacc acatgaaact atctattaca atacgctctt  14220
ttcaaatgag atgaaccccc cgcaacgaca tttcgggccg accccaactc agtttttgaa  14280
ttcggttgtt tataggaatc tacaggcgga ggtaacatgc aaggatggat ttgtccaaga  14340
gttccgtcca ttatggagag aaaatacaga ggaaagtgac ctgacctcag ataaagcagt  14400
ggggtatatt acatctgcag taccctacag atctgtatca ttgctgcatt gtgacattga  14460
aattcctcca gggtccaatc aaagcttact agatcaacta gctatcaatt tatctctgat  14520
tgccatgcat tctgtaaggg agggcggggt agtaatcatc aaagtgttgt atgcaatggg  14580
atactacttt catctactca tgaacttgtt tgctccgtgt tccacaaaag gatatattct  14640
ctctaatggt tatgcatgtc gaggggatat ggagtgttac ctggtatttg tcatgggtta  14700
cctgggcggg cctacatttg tacatgaggt ggtgaggatg gcaaaaactc tggtgcagcg  14760
gcacggtacg cttttgtcta aatcagatga gatcacactg accaggttat tcacctcaca  14820
gcggcagcgt gtgacagaca tcctatccag tcctttacca agattaataa agtacttgag  14880
gaagaatatt gacactgcgc tgattgaagc cgggggacag cccgtccgtc cattctgtgc  14940
ggagagtctg gtgagcacgc tagcgaacat aactcagata acccagatca tcgctagcca  15000
cattgacaca gttatccggt ctgtgatata tatggaagct gagggtgatc tcgctgacac  15060
agtatttcta tttacccctt acaatctctc tactgacggg aaaaagagga catcacttaa  15120
acagtgcacg agacagatcc tagaggttac aatactaggt cttagagtcg aaaatctcaa  15180
taaaataggc gatataatca gcctagtgct taaaggcatg atctccatgg aggaccttat  15240
cccactaagg acatacttga agcatagtac ctgccctaaa tatttgaagg ctgtcctagg  15300
tattaccaaa ctcaaagaaa tgtttacaga cacttctgta ctgtacttga ctcgtgctca  15360
acaaaaattc tacatgaaaa ctataggcaa tgcagtcaaa ggatattaca gtaactgtga  15420
ctcctaacga aaatcacata ttaataggct cctttttttgg ccaattgtat tcttgttgat  15480
ttaattatat tatgttagaa aaaagttgaa ctctgactcc ttaggactcg aattcgaact  15540
caaataaatg tctttaaaaa aggttgcgca caattattct tgagtgtagt ctcgtcattc  15600
accaaatctt tgtttggt                                                15618
```

<210> SEQ ID NO 26
<211> LENGTH: 31
<212> TYPE: DNA
<213> ORGANISM: Artificial Sequence -continued

```
<220> FEATURE:
<223> OTHER INFORMATION: chemically synthesized

<400> SEQUENCE: 26

aacgctctag agggtgaaat gacgctcaat a                              31


<210> SEQ ID NO 27
<211> LENGTH: 29
<212> TYPE: DNA
<213> ORGANISM: Artificial Sequence
<220> FEATURE:
<223> OTHER INFORMATION: chemically synthesized

<400> SEQUENCE: 27

cgtgcaagct tttgccacca gctaaatta                                 29
```

ALTERED AVIAN VIRUS FOR IN-OVO INOCULATION AND METHODS OF USE THEREOF

CROSS REFERENCE TO RELATED APPLICATION

This application is related to and claims priority to U.S. Patent Application 62/459,254 filed on Feb. 15, 2017, the contents of which are incorporated herein.

BACKGROUND OF THE INVENTION

Sequence Listing

The Sequence Listing submitted via EFS-Web as ASCII compliant text file format (.txt) filed on Feb. 7, 2018, named "Sequence_Listing_ST25", (created on Feb. 7, 2018, 132 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

FIELD OF THE INVENTION

This invention relates to an altered Newcastle Disease Virus (NDV) containing the coding sequence of avian interleukin-4 (IL-4), or a portion thereof, in the reverse orientation and to an immunogenic composition containing this altered NDV. After infecting a host's cell, the altered NDV produces RNA having the reverse complement sequence of IL-4, or a portion thereof, or dsRNA for avian IL-4, thereby silencing IL-4 production via RNAi. This invention also relates to a method of generating a stronger and earlier immune response in a hatchling chick against the wild-type NDV by inoculating the avian embryo in-ovo with the altered NDV. The NDV can also encode a heterologous antigen from a heterologous avian pathogen.

DESCRIPTION OF RELATED ART

Newcastle disease (ND) continues to be a threat to the poultry industry world-wide. Current biosecurity measures, commercialized vaccines, and vaccination protocols have been unable to stop the occurrence of outbreaks of virulent Newcastle disease virus (vNDV) around the world. See, e.g., Nath, et al., *Microb. Pathog.* 91:85-91 (2016); Sun, et al., *Genome Announc.* 1(3):e00169-13 (2013); Shabbir, et al., *Virology J.* 10:170 (2013); Kammon, et al., *Avian Diseases* 59:422-430 (2015); and Jaganathan, et al., *BMC Vet. Res.* 11:219 (2015). Developing countries are being particularly hit hard by vNDV. See, Ganar, et al., *Virus Research* 184:71-81 (2014). It is imperative that an effective immunogenic composition and/or NDV which is able to overcome or reduce maternal antibody inhibition and protect animals at early stages of life against vNDV is created. Such an immunogenic composition must be able to boost the animal's cellular and humoral immune responses to achieve clearance of the virus and reduce viral transmission without compromising the animals' health.

People attempted to develop improved immunogenic compositions by using viruses that are homologous to the vNDV strains. However, while these vaccines reduce viral shedding, they are not currently commercially available nor protect vaccinated animals very early in life. See, e.g., Cardenas-Garcia, et al., *Biologicals J. Intern. Assoc. Biol. Standard.* 43:136-145 (2015); Miller, et al., *Avian Diseases* 53:39-49 (2009); Kim, et al., *PloS ONE* 8:e74022 (2013); and Miller, et al., *Develop. Comp. Imm.* 41:505-513 (2013).

In-ovo vaccination has been explored as an option to confer protection early in life. Currently, two vaccines can be administered in-ovo. One vaccine is a recombinant herpes virus from turkey (rHVT) expressing the F protein from NDV. This rHVT confers long-lasting protection against challenge with vNDV after a single application without causing clinical signs (Palya, et al., *Vet. Immun. Immunopath.,* 158:105-115 (2014); and Palya, et al., *Avian Diseases,* 56:282-287 (2012)). Unfortunately, this vaccine takes at least four weeks to generate a protective immune response in the animal (Palya, et al. (2012); and Esaki, et al., *Avian Diseases,* 57:750-755 (2013)) which compromises flocks during an outbreak. Further, no reliable test for determining and monitoring a vaccinated animal's antibody response exists. The second vaccine contains live NDV conjugated to an antibody. The antibody is slowly released from the virus over time, and prevents the usual mortality observed when administering a live NDV vaccine in-ovo (Kapczynski, et al., *Avian Diseases,* 56:555-560 (2012)). However, the efficacy of this vaccine is inconsistent.

Live NDV vaccines are inexpensive to produce and usually induce a strong cell-mediated immune response. They generate neutralizing immunity when given by mouth or eye within two weeks after hatching and mucosal immunity. The poultry industry is familiar with live NDV vaccines. However, some live NDV vaccines (e.g., LaSota strain) cause mild to moderate respiratory disease and reduce productivity (Gallili, et al., *Biotech. Advances,* 16:343-366 (1998)). Also, live NDV vaccines are lethal to embryos and cannot be administered in-ovo.

Inactivated NDV vaccines do not replicate in the host and therefore, do not induce clinical disease. Such vaccines do not elicit a strong cell-mediated immune response (Virgil, et al., *Practical Aspects of Poultry Vaccination* (pp. 345-362) in *Avian Immunology,* 2nd ed., Schat, et al. (eds.) Elsevier Science (2013)), but they induce long-lasting antibody response (Jansen, et al., *Vaccine,* 23:1053-1060 (2005). However, both cellular-mediated immunity (CMI) and antibody-mediated immunity (or humoral immunity) are important for NDV clearance and neutralization. CMI is crucial for clearance of viral particles through activation of macrophages or by destroying infected cells through activation of cytotoxic T lymphocytes. Antibody-mediated immune response is important for neutralization of free circulating viral particles and newly developed viral progeny. Antigen-specific antibodies opsonize free viral particles and facilitate neutralization and destruction through phagocytosis, mainly by macrophages to avoid further reinfection of host cells. See, Kaiser, P, *Avian Path. J. of WVPA,* 39:309-324 (2010).

NDV is an avian paramyxovirus. Avian paramyxoviruses are very common viruses normally isolated from wide range of avian species around the world. Most avian paramyxoviruses are not economically significant because they can replicate in avian species of commercial interest (chicken, ducks, turkeys) without causing clinical signs or disease. There are currently 13 recognized serotypes of avian paramyxoviruses named APMV-1 to APMV-13. These viruses that belong to the Paramyxoviridae family have potential as vaccine vectors to protect against Newcastle disease and other avian, and mammalian diseases. See, Dimitrov, et al., *Vet Microbiol.* S0378-1135(16)30804-5 (2016); and Kim, et al., *Viruses* 8(7) (2016). The use of a recombinant APMV that expresses a heterologous antigen from an avian pathogen vaccine is attractive because of the recombinant APMV has low or non-existent capacity to recombine or to integrate into the host's genome.

Thus, a need exists for an altered NDV, and an immunogenic composition containing the altered NDV, that is able to confer strong cell-mediated and strong antibody-mediated immune responses in hatchling chicks in order to decrease virulent virus replication and shedding to a level that inhibits or decreases horizontal transmission, which is difficult to achieve without compromising a bird's health and productivity. Further, a need exists for an altered NDV, and an immunogenic composition containing the altered NDV, that can be administered safely in-ovo so that animals are protected at an early stage of life.

BRIEF SUMMARY OF THE INVENTION

It is an object of this invention to have an altered NDV that encodes anti-sense interleukin 4 (IL-4) or a fragment thereof. Chicken IL-4 or fragment thereof can be SEQ ID NO: 1 or 4. The anti-sense chicken IL-4 or fragment thereof can be SEQ ID NO: 2, 3, 5, or 23 or the reverse, complementary sequence of SEQ ID NO: 1. It is another object of this invention that the altered NDV contain the reverse, complementary RNA equivalent sequence of SEQ ID NO: 2, 3, 5, or 23. It is another object of this invention that the altered NDV contains the RNA sequence of SEQ ID NO: 1 which is transcribed into anti-sense IL-4 with reverse, complementary RNA equivalent of SEQ ID NO: 1. It is further object of this invention that the altered NDV encodes a heterologous antigen from a heterologous avian pathogen and produces that heterologous antigen after infecting the bird's cells. Another object of the invention involves the altered NDV being attenuated.

It is an object of this invention to have an immunogenic composition containing the above described altered NDV and a pharmaceutically acceptable carrier. Another object of this invention is that the immunogenic composition contains an adjuvant.

It is another object of this invention to have a plasmid that encodes the altered NDV that encodes and produces anti-sense IL-4 (full-length or fragment). It is a further object of this invention that the plasmid encodes a lentogenic or attenuated NDV that can produce anti-sense IL-4 after the altered NDV infects a bird's cells. It is a further object of this invention that the plasmid encoding the altered NDV also contains the coding sequence of one or more heterologous antigens from a heterologous avian pathogen such that after the altered NDV infects a bird's cells, anti-sense IL-4 and the one or more heterologous antigens are produced. Two such possible heterologous antigens are gB and/or gD from infectious laryngotracheitis virus (ILTV). It is a further object of this invention that the plasmid contains the reverse, complementary sequence of SEQ ID NO: 1, or one of SEQ ID NOs: 2, 3, 5, or 23 so that anti-sense IL-4 can be produced; and a sequence that encodes ILTV's gB protein (SEQ ID NO: 12) and/or gD protein (SEQ ID NO: 14). In another embodiment, the plasmid has SEQ ID NO: 16 or 24.

Another object of this invention is a method to protect a hatchling chick from a disease caused by an avian pathogen, such as, but not limited to NDV, by administering to an embryonic bird in-ovo an effective dosage of the altered NDV described above or the immunogenic composition containing the altered NDV described above and incubating the in-ovo inoculated embryonic bird to hatch and become an in-ovo inoculated hatchling chick. It is a further object of this invention that the altered NDV produces in-ovo (i) at least one NDV antigen, (ii) RNA with a sequence that is complementary to mRNA for IL-4 or a fragment thereof produced by the animal, and (iii) optionally a heterologous antigen. It is a further object of this invention that the RNA complementary to mRNA for IL-4 or a fragment thereof reduces IL-4 production in the inoculated embryonic bird in-ovo via RNAi, and that the in-ovo inoculated hatchling chick produces antibodies against the avian pathogen antigen, and the optional heterologous antigen, that protect the in-ovo inoculated hatching bird from the avian pathogen, and the heterologous pathogen. It is another object of this invention that the altered NDV produces RNA complementary to mRNA of SEQ ID NO: 1 or 4; or produces RNA based on the RNA equivalent sequence of SEQ ID NO: 2, 3, 5, or 23. It is another object of the invention that the altered NDV contains a polynucleotide (RNA) that encodes one or more heterologous antigens from an avian pathogen and produces the one or more heterologous antigens (such as ILTV's gB and/or gD proteins). In an alternative embodiment, the altered NDV produces dsRNA for IL-4 or a fragment thereof.

It is a further object of this invention of increasing an in-ovo inoculated hatchling chick's survival rate after exposure to an avian pathogen compared to a non-inoculated hatchling chick's survival rate after exposure to an avian pathogen by administering to an embryonic bird in-ovo an effective dosage of the altered NDV described above or the immunogenic composition described above to produce an inoculated embryonic bird and incubating the inoculated embryonic bird until it hatches thus generating an in-ovo inoculated hatchling chick. It is another object of this invention that the altered NDV or in the immunogenic composition produces in-ovo at least one antigen from the NDV. It is another object of this invention that the altered NDV produces in-ovo RNA complementary to mRNA for IL-4 or a fragment thereof, that the RNA complementary to mRNA for IL-4 or a fragment thereof reduces IL-4 production in the embryonic bird in-ovo via RNAi, and that the in-ovo inoculated hatchling chick has protective immunity against NDV and increased survival rate after exposure to NDV compared to the survival rate of a non-inoculated hatchling chick after exposure to NDV. It is another object of this invention that the altered NDV produces RNA complementary to mRNA of SEQ ID NO: 1 or 4; or RNA based on the RNA equivalent sequence of SEQ ID NO: 2, 3, 5, or 23. It is another object of the invention that the altered NDV contains a polynucleotide (RNA) that encodes a heterologous antigen from a heterologous avian pathogen, produces that heterologous antigen, and that the in-ovo inoculated hatchling chick has a protective immune response against that heterologous pathogen, thus increasing the survival rate. In an alternative embodiment, the altered NDV produces dsRNA for IL-4 or a fragment thereof.

It is an object of this invention to have a method for increasing the humoral immune response against an avian pathogen in vaccinated in-ovo embryo birds and hatchlings compared to the humoral immune response against the avian pathogen in non-vaccinated embryo birds and hatchlings. It is another object of this invention that the method involves administering to bird embryos in-ovo an altered NDV that produces anti-sense RNA or dsRNA for IL-4 which increases the humoral immune response of the vaccinated embryos and hatchlings to NDV (compared to the humoral immune response in unvaccinated embryos and hatchlings to NDV). It is another object of this invention that the altered NDV encodes a heterologous antigen from a heterologous avian pathogen (an avian pathogen other than NDV) and produces that heterologous antigen after in-ovo administration, thereby increasing the humoral response against that heterologous antigen and heterologous avian pathogen (compared to the humoral immune response in unvaccinated embryos and hatchlings to that heterologous antigen and heterologous avian pathogen).

BRIEF DESCRIPTION OF THE SEVERAL VIEWS OF THE DRAWINGS

FIG. 2A is the survival rate of hatchling chicks vaccinated with the indicated viruses at 18 days of embryonation (doe) with $10^{4.5}$ $EID_{50}$ per egg.

FIG. 2B is the survival rate of hatchling chicks vaccinated with the indicated viruses at 18 doe with $10^5$ $EID_{50}$ per egg. FIG. 2C is the survival rate of hatchling chicks vaccinated with the indicated viruses at 18 doe with $10^{7.5}$ $EID_{50}$ per egg. FIG. 2D is the survival rate of hatchling chicks vaccinated with the indicated viruses at 19 doe with $10^{3.5}$ $EID_{50}$ per egg. Curves sharing letters are not significantly different from one another when analyzed using the Long-Rank test at a level of significance of 5%.

FIG. 5A shows the average body weight of in-ovo vaccinated hatchling chicks at 1, 8, 14 dph. FIG. 5B shows the average body weight of in-ovo vaccinated chickens at 14 dpc. Significant differences between groups are denoted by different letters, columns sharing letters are not significantly different from one another after being analyzed with the Tukey's test for multiple comparisons with a level of significance of 5%.

DETAILED DESCRIPTION OF THE INVENTION

Figure 1:
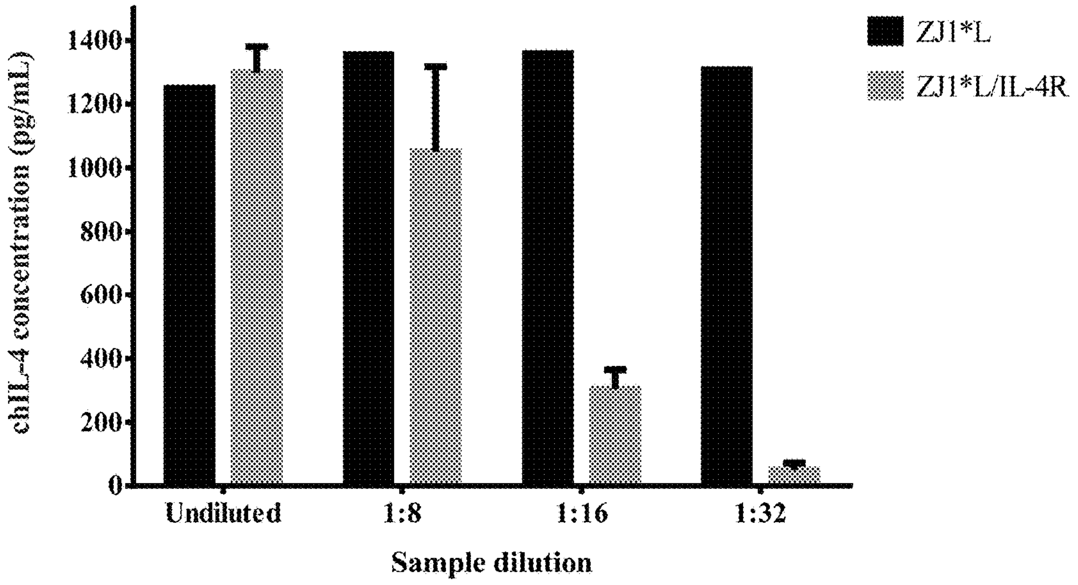
FIG. 1 shows the level of chicken IL-4 expression in ten-day-old specific-pathogen-free (SPF) embryonating chicken eggs (ECEs) after infection with either ZJ1*L (vNDV) or ZJ1*L/IL-4R, as determined by ELISA of infective allantoic fluids.

A need exists for an altered NDV, and an immunogenic composition containing that altered NDV, that protects birds immediately (or within a few days) after hatching against avian viruses, including, but not limited to, NDV. This invention involves an altered NDV that produces anti-sense RNA for avian IL-4 (i.e., RNA that is complementary to mRNA encoding avian IL-4 or a fragment thereof), or dsRNA for avian IL-4. The altered NDV thus contains a RNA equivalent of avian IL-4 or a fragment thereof in the reverse orientation or contains a RNA equivalent of a sense region and the complementary anti-sense region of avian IL-4. In one embodiment, the IL-4 being silenced is chicken IL-4 (chIL-4). In another embodiment, the IL-4 being silenced is the IL-4 specific for the avian species of the bird being inoculated. The altered NDV can also encode an antigen from a heterologous virus, bacteria, or other pathogen that infects birds. An immunogenic composition containing the altered NDV is part of this invention.

In one embodiment, this invention involves an immunogenic composition containing the altered NDV of this invention and a pharmaceutically acceptable carrier. In another embodiment, the immunogenic composition also contains an adjuvant. In yet another embodiment, the immunogenic composition contains a heterologous avian pathogen. The heterologous avian pathogen may be attenuated or inactivated. Examples of heterologous avian pathogens can include, but are not limited to, avian influenza, infectious laryngotracheitis virus (ILTV), avian pox virus, Gallid herpesvirus, avian rhinotracheitis virus, avian encephalomyelitis virus, *Cryptosporidium* spp., *Giardia* spp. *Chlamydia* spp., *Salmonella* spp., *Campilobacter* spp., and *Clostridium* spp. In yet another embodiment, the altered NDV also encodes a heterologous antigen (i.e., an antigen from a heterologous avian pathogen). For example, the altered NDV can encode the gB protein or gD protein from ILTV and cause the production of the encoded antigen after administration to a bird or egg.

After administering this immunogenic composition to an embryonic bird in-ovo, the altered NDV induces an infected cell to produce (i) a RNA that is complementary to the sequence of IL-4 mRNA (or a portion thereof); (ii) one RNA containing a set of IL-4 complementary sequences (sense and anti-sense sequences) such that the complementary sequences can bind together in a hair-pin loop structure, or (iii) two distinct RNAs—one RNA encoding a sense IL-4 sequence and the other RNA encoding an anti-sense IL-4 sequence that are complementary to each other, which bind to each other and form dsRNA. After in-ovo inoculation, an embryonic bird produces antibodies against the altered NDV (and any heterologous antigen produced by the altered NDV) and has a strong immune response at an earlier age after hatching compared to the immune response of a bird inoculated in-ovo with the wild-type NDV (which lacks the ability to produce anti-sense IL-4 RNA), and if applicable, to the pathogen from which the heterologous antigen belongs. Further, this altered avian virus can be administered at a lower dosage in-ovo than a wild-type avian virus that encodes for anti-sense IL-4 (or dsRNA for IL-4) or fragment thereof, and this altered avian virus does not kill the embryonic bird nor the hatchling chick.

While the altered NDV described in the examples below discuss attenuated NDV which contains a RNA equivalent of chicken IL-4 in the reverse orientation, one can use the RNA equivalent of IL-4 cds from the animal which is to receive this immunogenic composition. Such animals include, but are not limited to, domestic, wild and game birds such as chickens, turkeys and other gallinaceous birds, ducks, and geese. In addition, although the examples below describe using a specific strain of NDV, any NDV strain can be used in this invention.

For this invention, the coding sequence of chIL-4 is found at GenBank accession number NM_001007079.1 and is in SEQ ID NO: 1 (411 nt long). SEQ ID NO: 2 contains the reverse complementary sequence of SEQ ID NO: 2 which is used to silence the avian IL-4 gene expression. SEQ ID NO: 3 also can be used to silence avian IL-4 expression, and is the reverse complementary sequence of SEQ ID NO: 1 plus three additional nucleotides at the 5' end (414 nt long). Thus, SEQ ID NO: 3 is slightly different from SEQ ID NO: 2. A short sequence of anti-sense IL-4 that is highly conserved among birds and can be used to modulate the response of a broad number of avian species is nucleotides 330 to 351 of GenBank accession NM_001007079 which correspond to the sense sequence 5'-GGCAGCAGGCAACACTACTTCAATG-3' (SEQ ID NO: 4) and its anti-sense sequence (reverse, complementary sequence) 5'-CATTGAAGTAGTGTTGCCTGCTGCC-3' (SEQ ID NO: 5). NDV is a member of the avian paramyxovirus family of viruses which has a genome contains a non-segmented, negative-sense, single-strand of RNA. Thus, when discussed herein that a particular altered NDV genomic sequence is SEQ ID NOs: 18 or 25, the altered NDV genomic sequence really is an RNA sequence that is the reverse, complementary sequence of SEQ ID NOs: 18 or 25. Similarly, when discussed herein that an altered NDV contains a heterologous DNA sequence (such as SEQ ID NOs: 2, 3, 5, 13, 15, or 23), then the altered NDV genomic sequence is an RNA sequence that contains the reverse, complementary sequence of such heterologous DNA sequence. Every attempt is made herein to clarify these subtle distinctions when referring to the sequences.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids containing known nucleotide analogs or modified backbone residues or linkages, which can be synthetic, naturally occurring, or non-naturally occurring, which have similar binding properties similar to the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs). "Polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein, unless the context is understood to be specific to the particular nucleic acid mentioned. For the sake of clarity, "DNA" means a polymer of deoxyribonucleotides, and "RNA" means a polymer of ribonucleotides.

The term "primer" as used herein, refers to short nucleic acids, typically a DNA oligonucleotide approximately 15 nucleotides in length. In one embodiment, primers are annealed to a complementary target DNA or RNA strand by nucleic acid hybridization to form a hybrid between the primer and the target DNA or RNA strand. Annealed primers are then extended along the target strand by a DNA polymerase or a reverse transcriptase. Primer pairs can be used for amplification of a nucleic acid sequence, e.g., by the polymerase chain reaction (PCR) or other nucleic-acid amplification methods known in the art.

An "immunogenic composition" contains an antigen that, when administered to a subject, results in an immune response. The subject's immune response may be a humoral and/or a cellular immune response. The immune response can be an increase or decrease of humoral and/or cellular immunity. For this invention, the immunogenic composition contains an altered NDV which produces anti-sense RNA or dsRNA for IL-4 as described herein (with or without production of a heterologous antigen). The immunogenic composition can optionally containing a diluent, an adjuvant, and/or a pharmaceutically acceptable carrier. In one embodiment, the altered NDV is a lentogenic strain, an attenuated mesogenic strain, or an attenuated velogenic strain.

An "immunological response" or "immune response" to an antigen or immunogenic composition is a change in a subject's humoral and/or cellular immune response to the antigen(s) present in the immunogenic composition. The immune response may be an increased (enhanced) or decreased (suppressed) response by the host's immune system. The immune response may be a systemic and/or a mucosal immune response. The immune response may be a humoral immune response and/or a cellular immune response. "Humoral" immunity refers to an immune response mediated by antibodies and B-cells, while "cellular" immunity refers to an immune response mediated by T-lymphocytes and/or other white blood cells. The invention described herein, when administered to eggs, increases the humoral immune response in the vaccinated embryos and hatchlings compared to the humoral immune response level in unvaccinated embryos and hatchlings.

One important aspect of cellular mediated immunity (CMI) involves an antigen-specific response by cytolytic T-cells ("CTL" or "CTLs"). CTLs have specificity for peptide antigens that are presented in association with proteins encoded by the major histocompatibility complex ("MHC") and which are expressed on the surfaces of cells. CTLs induce and promote the destruction of intracellular microbes, or the lysis of cells infected with such microbes. Another aspect of cellular immune response involves an antigen-specific response by helper T-cells (Th cells). Th cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+ T-cells.

Th cells include Th1 cells and/or Th2 cells. A Th1 cell immune response may include one or more of the following: an increase or decrease in CD8+ CTLs; an increase or decrease in one or more of the cytokines associated with a Th1 cell immune response (such as IL-12, IFN-γ, and TNF-β); an increase or decrease in activated macrophages; an increase or decrease in NK activity; and/or an increase or decrease in the production of IgG2a. In one embodiment, the enhanced or suppressed Th1 cell immune response will include an increase or decrease in IL-12 and IgG2a production, respectively. In another embodiment, an enhanced or suppressed Th1 cell immune response includes an increase or decrease in CD8+ CTLs, respectively. Activated Th2 cells enhance antibody production and are therefore of value in responding to certain types of extracellular infections. Activated Th2 cells may secrete one or more of IL-4, IL-5, IL-6, and IL-10. A Th2 cell immune response may result in the production of IgG1, IgE, IgA and memory B cells for future protection (a humoral immune response). However, in some cases, it is beneficial to suppress or reduce Th2 cells' secretion of one or more of IL-4, IL-5, IL-6, and IL-10. In this particular invention, a decrease in the secretion of IL-4 is desired. Not wishing to be bound to any particular hypothesis, it is possible that such a decrease is caused using RNAi technology in which RNA having a sequence that is the reverse, complement of IL-4 (or a fragment thereof) is produced and which binds to mRNA encoding IL-4 or dsRNA for IL-4 is produced.

The ability of a particular antigen or immunogenic composition to stimulate CMI may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* 151:4189-4199 (1993); Doe et al., *Eur. J. Immunol.* 24:2369-2376 (1994). Recent methods of measuring cell-mediated immune response include measurement of intracellular cytokines or cytokine secretion by T-cell populations, or by measurement of epitope specific T-cells (e.g., by the tetramer technique)(reviewed by McMichael and O'Callaghan, *J. Exp. Med.* 187(9) 1367-1371 (1998); Mcheyzer-Williams et al., *Immunol. Rev.* 150:5-21 (1996); Lalvani et al., *J. Exp. Med.* 186:859-865 (1997)).

Humoral mediated immunity results in the production of antibodies (e.g., neutralizing antibodies that block bacterial toxins and pathogens such as viruses entering cells and replicating by binding to toxins and pathogens, typically protecting cells from infection and destruction). Hence, humoral mediated immunity may include one or more of the following effects: the production of antibodies by B-cells; and/or the activation of suppressor T-cells and/or memory/effector T-cells directed specifically to an antigen or antigens present in the immunogenic composition or vaccine. These responses may serve to neutralize infectivity, and/or mediate antibody-complement, or antibody dependent cell cytotoxicity (ADCC) to provide protection to an immunized subject. Such responses can be determined using standard immunoassays and neutralization assays, well known in the art. See, e.g., Montefiori et al., *J. Clin Microbiol.* 26:231-235 (1988); Dreyer et al., *AIDS Res. Hum. Retroviruses* 15(17): 1563-1571 (1999). The innate immune system of the subject also recognizes and responds to molecular features of pathogenic organisms via activation of Toll-like receptors and similar receptor molecules on immune cells. Upon activation of the innate immune system, various non-adaptive immune response cells are activated to produce, e.g., various cytokines, lymphokines, and chemokines. Cells activated by an innate immune response include immature and mature dendritic cells, as well as gamma, delta, alpha and beta T cells and B cells and the like. Thus, the present invention also contemplates an immune response wherein the immune response involves both an innate and adaptive response. In the present invention, it is hypothesized that the production of IL-4 is reduced while the production of other cytokines are not negatively impacted.

"Vaccination" or "immunization" or "inoculation" is the administration of the altered avian virus or the immunogenic composition to the subject. Routes of administration include, but not limited to, in-ovo administration, intramuscular injection, intraperitoneal injection, subdermal injection, subcutaneous injection, intravenous injection, oral administration, sublingual administration, inhalation administration, intraocular administration, or transcutaneous adsorption. One embodiment involves in-ovo administration. Another embodiment involves spraying the immunogenic composition.

The immunogenic composition may be prepared for administration by formulating an effective immunization dosage of the antigen (altered avian virus with or without heterologous antigen being produced) with a pharmaceutically acceptable carrier or diluent, such as physiological saline or tissue culture medium. The expression "effective immunization dosage" is that amount which will induce immunity in a bird against challenge by a virulent strain of a virus or that amount which will induce immunity in a subject against a challenge with a virulent virus. Immunity is considered as having been induced in a subject when the level of protection for the immunized subject is significantly higher than that of an unvaccinated control group. For NDV, one measure of the level of protection is the hemagglutination inhibition assay (HI), which is calculated as in the examples infra. Another measure of protection is viral shedding and mortality rates after challenge with the virus. The effective immunization dose of the immunogenic composition of the present invention depends on several variables such as the presence and quantity of maternal antibodies, the formulation, the route of administration, the subject's age, the subject's weight, the time of administration, the excretion rate, and reaction irritability. In one embodiment, the effective immunization dosage of the immunogenic composition of this invention ranges from approximately 10 $EID_{50}$ per egg to approximately $10^8$ $EID_{50}$ per egg. In another embodiment, the effective immunization dosage ranges from approximately 100 $EID_{50}$ per egg to approximately $10^5$ $EID_{50}$ per egg. In yet another embodiment, the effective immunization dosage ranges from approximately $10^3$ $EID_{50}$ per egg to approximately $10^{4.5}$ $EID_{50}$ per egg. In another embodiment, the effective immunization dosage ranges from approximately $10^3$ $EID_{50}$ per egg to approximately $10^4$ $EID_{50}$ per egg. The dosage for hatchling chicks can range from approximately 10 $EID_{50}$ per hatchling chick to approximately $10^{10}$ $EID_{50}$ per hatchling chick. In another embodiment, the effective immunization dosage ranges from approximately $10^2$ $EID_{50}$ per hatchling chick to approximately $10^8$ $EID_{50}$ per hatchling chick. In yet another embodiment, the effective immunization dosage ranges from approximately $10^3$ $EID_{50}$ per hatchling chick to approximately $10^6$ $EID_{50}$ per hatchling chick. In another embodiment, the effective immunization dosage ranges from approximately $10^3$ $EID_{50}$ per hatchling chick to approximately $10^5$ $EID_{50}$ per hatchling chick. These ranges of effective dosages can change depending the amount of maternal antibodies that bind to the virus present in the animal being vaccinated.

"Antibody" or "antibodies" encompass polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al., *Nature* 349:293-299 (1991); and U.S. Pat. No. 4,816,567); $F(ab')_2$ and F(ab) fragments; Fv molecules (noncovalent heterodimers, see, for example, Inbar et al., *Proc. Natl. Acad. Sci. USA* 69:2659-2662 (1972); and Ehrlich et al., *Biochem.* 19:4091-4096 (1980)); single-chain Fv molecules (sFv) (see, e.g., Huston et al., *Proc. Natl. Acad. Sci. USA* 85:5879-5883 (1988)); dimeric and trimeric antibody fragment constructs; minibodies (see, e.g., Pack et al., *Biochem.* 31:1579-1584 (1992); Cumber et al., *J. Immunology* 149B: 120-126 (1992)); humanized antibody molecules (see, e.g., Riechmann et al., *Nature* 332:323-327 (1988); Verhoeyan et al., *Science* 239:1534-1536 (1988); and U.K. Patent Publication No. GB 2,276,169, published 21 Sep. 1994); and, any functional fragments obtained from such molecules, wherein such fragments retain specific-binding properties of the parent antibody molecule, unless the content of the text suggests that only monoclonal and/or polyclonal antibodies are intended.

A "subject" or "recipient" is any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like; and fish such as salmon, catfish, trout, tuna, goldfish, and other types of fish. The term does not denote a particular age. Thus, both adult and newborn animals are intended to be covered. In one embodiment, the subject being inoculated is an embryonic bird. In another embodiment, the subject being inoculated is a hatchling chick. A hatchling chick is any bird that is less than 4 weeks post-hatching.

"Treatment" refers to any of (i) the prevention of infection or reinfection, as in a traditional vaccine or immunogenic composition, (ii) the reduction or elimination of symptoms, (iii) the substantial or complete elimination of the pathogen in question, and (iv) an enhanced immune response to the antigen or immunogenic composition administered to the subject. Treatment may be effected prophylactically (prior to infection) or therapeutically (following infection).

One method of assessing efficacy of an immunogenic composition involves monitoring infection after administration of the immunogenic composition. One method of assessing efficacy of prophylactic administration of the immunogenic composition involves monitoring immune responses against the antigens in the immunogenic composition after administration of the immunogenic composition. Another method of assessing the immunogenicity of the proteins of the immunogenic composition is to express recombinantly the proteins and to screen a subject's sera or mucosal secretions by immunoblot. A positive reaction between the protein and the subject's serum indicates that the subject previously mounted an immune response to the protein in question—that is, the protein is an immunogen. This method may also be used to identify immunodominant proteins and/or epitopes. Survival rates of immunized animals after challenge with a virulent strain of the microorganism, shedding of the microorganism, disease symptoms, and antibody titers are other assays for assessing efficacy of an immunogenic composition. With NDV, HI assays also assess efficacy. Systemic immune response involves $IgG_1$ and $IgG_{2a}$ production; mucosal immune response involves IgA production. Typically, serum-specific antibody responses are determined post-immunization but not pre-challenge, whereas mucosal-specific antibody body responses are determined post-immunization and post-challenge.

Immunogenic compositions of the present invention may be used either alone or in combination with other antigens and/or optionally with an immunoregulatory agent ("adjuvant") capable of eliciting humoral and/or cellular immune response. An immunogenic composition of this invention includes the antigens of this invention and one or more adjuvants. Non-limiting examples of adjuvants include oil-in-water emulsion, water-in-oil-in-water emulsion, aluminum hydroxide, aluminum phosphate, squalene and squalene-like compounds, Freund's complete adjuvant, Freund's incomplete adjuvant, muramyl dipeptide, monophosphoryl lipid A, polyphosphazine, *E. coli* LT (or LT-B, native or toxoid), CpG motif containing oligonucleotide, and compounds that interact with Toll-like Receptors (TLR). Adjuvants which are capable of preferential stimulation of the Th1 cell response are described in International Patent Application No. WO 94/00153 and WO 95/17209.

The invention also provides for the immunogenic composition described herein to be used as a medicament. A medicament is preferably able to generate an immune response in a subject. The invention also provides for the use of the immunogenic composition of the invention in the manufacture of a medicament for generating an immune response in a subject. In one embodiment, the medicament is a vaccine or an immunogenic composition. In one embodiment, the immunogenic composition is used to prevent and/or treat a viral infection.

The immunogenic composition of this invention may also contain one or more pharmaceutically acceptable carriers. Non-limited examples of such carriers include phosphate buffered saline (PBS), lactose, dextrose, sucrose, sorbitol, mannitol, starch, acacia gum, calcium phosphate, calcium silicate, calcium silicate, water, syrup, methyl cellulose, methyl hydroxybenzoate, propyl hydroxybenzoate, talc, stearic acid, magnesium, mineral oils, and polymers such as alginate, gelatin, cellulose, microcrystalline cellulose, methyl cellulose, polyvinylpyrrolidone, poly-lactic acid (PLA), poly-glycolic acid (PGA), and poly-lactic-co-glycolic acid (PLGA). In addition to the above ingredients of the immunogenic composition according to the present invention may further comprise lubricants, wetting agents, sweetening agents, flavoring agents, emulsifiers, suspending agents, preservatives, etc. Suitable pharmaceutically acceptable carriers and formulations are described in detail in *Remington's Pharmaceutical Sciences* (19th ed., 1995). While the immunogenic compositions of the present invention can be used in animals but not humans, "pharmaceutically acceptable" refers to those items, compounds, etc. that are approved for use in human and/or in animals.

The invention also provides for methods for inducing or increasing an immune response using the altered NDV and/or the immunogenic composition containing the altered NDV. The immune response is preferably protective and can include antibodies and/or cell-mediated immunity (including systemic and mucosal immunity). Immune responses include booster responses.

The invention also includes kits containing one or more containers of the immunogenic composition of the invention or one or more of the altered NDV. The immunogenic composition can be in liquid form or can be lyophilized, as can individual antigens. Suitable containers for the compositions include, for example, bottles, jugs, vials, syringes, and test tubes. Containers can be formed from a variety of materials, including glass or plastic. A container may have a sterile access port (for example, the container may be an intravenous solution bag or a vial having a stopper pierceable by a hypodermic injection needle). The kit can also contain a second container inside of which is a pharmaceutically-acceptable buffer, such as phosphate-buffered saline, Ringer's solution, or dextrose solution. The kit can also contain other materials useful to the end-user, including other pharmaceutically acceptable formulating solutions such as buffers and/or diluents, filters, needles, and syringes or other delivery devices. The kit may optionally include an adjuvant in a container. The kit can also contain written instructions for administering the immunogenic composition and other contents of the kits to subjects. The written instructions may describe methods for inducing an immune reaction or methods for treating infections. The invention also includes a delivery device pre-filled with the immunogenic composition of the invention.

In the examples below, an RNA sequence that is equivalent to the reverse, complementary coding sequence of chIL-4 (SEQ ID NO: 1) is placed between the P and M genes of the NDV genome, within the untranslated regions of the P gene. In such orientation, the altered NDV produces mRNA that is complementary to IL-4 mRNA produced by the animal. However, the heterologous polynucleotide can be placed at any point in the NDV genome. Location of placement of the heterologous polynucleotide can depend on the desired amount of RNA to be produced. See, Zhao, et al., *J. Gen. Virology,* 96:40-45 (2015) and Zhang, et al., *J. Gen. Virology,* 96:2028-2035 (2015) for protocols (contents of both articles are expressly incorporated herein).

In addition, the genome of the altered NDV can also contain the reverse, complementary RNA equivalent of the coding sequence of an antigen from another microorganism (e.g., virus, bacterium, parasite, or other pathogen) that infects birds. Such an reverse, complementary RNA equivalent is necessary so that the virus would generate mRNA that would be used to produce the heterologous antigen. Such an altered NDV can be administered in-ovo and result in protective immunity against NDV and the heterologous microorganism in the hatchling chicks inoculated with the altered NDV encoding the heterologous antigen. Non-limiting examples of such heterologous pathogen for which the sequence encoding a heterologous antigen can be placed in the altered NDV include ILTV, infectious bronchitis virus, Mareks disease virus, avian influenza virus, Gumboro or infectious bursal disease virus, chicken anemia virus, *Cryptosporidium* spp., *Eimeria* spp., *Giardia* sp., and *Trichomonas* spp. Genes normally used to produce antigenic protection against those pathogens include, but are not limited to, the surface protein and structural protein for these pathogens. Most commonly, for avian influenza, the HA gene is used, for Gumboro the gene encoding for the VP2 capsid protein, and for chicken anemia the VP1 gene. For ILTV, one can use the gB protein (SEQ ID NO: 12) and/or gD protein (SEQ ID NO: 14). The coding sequence for gB is SEQ ID NO: 13. The coding sequence for gD is SEQ ID NO: 15. The reverse, complementary RNA equivalent of SEQ ID NO: 13 or 15 can be inserted into NDV between the NP and P genes, between the M and F genes, between the F and HN genes, between the HN and L genes, or after the L gene. See Zhao, et al. (2015); Zhang, et al. (2015); and U.S. Patent App. Pub. 2017-0072046. To generate such an altered NDV, one can use the methods described in these prior art documents and described below to generate a plasmid that encodes for the altered NDV and use plasmid rescue techniques with the plasmid to produce the altered NDV. This altered NDV, when it infects cells, will produce the heterologous antigen (for ILTV, gB (SEQ ID NO: 12) and/or gD (SEQ ID NO: 14)).

"dsRNA" refers to double-stranded RNA that comprises a sense region and an anti-sense region of a selected target gene (or sequences with high sequence identity thereto so that gene silencing can occur), as well as any smaller double-stranded RNAs formed therefrom by RNAse or Dicer activity. Such dsRNA can include portions of single-stranded RNA, but contains at least 18 base pairs of dsRNA. A dsRNA after been processed by Dicer generates siRNAs (18-25 bp in length) that are double-strand, and could contain ends with 2 nucleotide overhangs, which will be single-stranded. It is predicted that usually siRNA around 21 nt in length (or, alternatively, between 17 and 27 nt in length), will be incorporated into RISC. In one embodiment, the sense region and the anti-sense region of a dsRNA are on the same strand of RNA and are separated by a linker. In this embodiment, when the sense region and the anti-sense region anneal together, the dsRNA contains a loop which is the linker. One promoter operably linked to the DNA or RNA encoding both the sense region and the anti-sense region is used to produce the one RNA molecule containing both the sense region and the anti-sense region. In another embodiment, the sense region and the anti-sense region are present on two distinct strands of RNA (a sense strand and the anti-sense strand which is complementary to the sense strand) which anneal together to form the dsRNA. In this embodiment, a promoter is operably linked to each strand of DNA or RNA; where one DNA or RNA strand encodes the RNA containing the sense region and the other strand of DNA or RNA encodes the RNA containing the anti-sense region. In this embodiment, the promoter on each strand can be the same as or different from the promoter on the other strand. After the RNAs are transcribed, two RNA strands anneal together because the sense region and the anti-sense region are complementary to each other, thus forming the dsRNA. In yet another embodiment, one strand of DNA or RNA can encode both the sense region and the anti-sense region of the dsRNA. However, the DNA or RNA coding each region are separated from each other so that two promoters are necessary to transcribe each region. That is, the DNA or RNA encoding the anti-sense region and the DNA or RNA encoding the sense region are operably linked to their own promoter. Again, the two promoters can be the same promoter or different promoters.

In one embodiment of the invention, a recombinant NDV produces the anti-sense IL-4 (also referred to herein as the reverse complementary sequence of IL-4) or a fragment of IL-4. As such, the genome of recombinant NDV of this invention contains only one RNA polynucleotide (negative strand/anti-sense region) with the host animal cells producing the other RNA polynucleotide (positive strand/sense region). In this embodiment, the recombinant NDV can encode a fragment of or the full-length IL-4 sequence such that the produced polynucleotide (anti-sense region) can bind to the host cell's mRNA (positive strand/sense region) to generate dsRNA. In another embodiment, the recombinant NDV virus' genome can contain encode both the sense region and the anti-sense region for IL-4 as described supra to generate dsRNA—such as SEQ ID NO: 4 and 5, respectively, or another fragment of SEQ ID NO: 1 and the reverse complement of the fragment. In another embodiment, the altered NDV encodes the reverse, complementary RNA sequence of SEQ ID NOs: 2, 3, or fragments thereof (such as SEQ ID NO: 5).

In one embodiment, the dsRNA can be any 16, 17, 18, 19, 20, 21, 22, 23, 24, 25, 26, 27, 28, 29, 30, 31, 32, 33, 34, 35, 36, 37, 38, 39, 40, 45, 50, 55, 60, or longer contiguous nucleotides. In alternative embodiments, the dsRNA can range in length between 16 bp and 30 bp, between 16 bp and 25 bp, between 18 and 30 bp, and between 19 bp and 28 bp. In yet another embodiment, RNA forms that are created by RNAse III family (Dicer or Dicer-like ribonuclease) or Dicer activity that are longer dsRNA are within the scope of this invention.

One can use computer programs to predict dsRNA sequences that will be effective in reducing production of the desired gene/protein (in this embodiment IL-4). Information about such computer programs can be found at genelink-.com/siRNA/RNAiwhatis.asp and at rnaiweb.com/RNAi/RNAi_Web_Resources/RNAi_Tools_Software/Online_siRNA_Design_Tools/index.html. Using such computer programs, one can obtain sequences that differ from SEQ ID NOs: 1 or 2 which can be used to generate dsRNA via binding to chicken IL-4 mRNA or via binding to its own reverse complementary sequence.

siRNA can be synthetically made, expressed and secreted directly from a transformed cell, or microbe, or can be generated from a longer dsRNA by enzymatic activity. These siRNAs can be blunt-ended or can have 1 bp to 4 bp overlapping ends of various nucleotide combinations. Also modified microRNAs comprising a portion of IL-4 (or chIL-4) and its reverse complementary sequence are included herein as dsRNAs. In another embodiment of the invention, the dsRNA is produced by an organism other than the recombinant NDV described herein; or it is synthetically produced and then applied together with the desired avian RNA virus (NDV) (an immunogenic composition of the desired avian RNA virus and dsRNA) to the egg. Alternatively, a microorganism that is not an avian RNA virus can be generated which produced the dsRNA for IL-4 and is combined with the desired avian RNA virus into an immunogenic composition which is administered to eggs.

This invention utilizes routine techniques in the field of molecular biology. Basic texts disclosing the general methods of use in this invention include Sambrook et al., *Molecular Cloning—A Laboratory Manual* (2nd Ed.), Vol. 1-3, Cold Spring Harbor Laboratory, Cold Spring Harbor, N.Y. (1989); Kriegler, *Gene Transfer and Expression: A Laboratory Manual* (1990); and Ausubel et al. (eds.), *Current Protocols in Molecular Biology* (1994). Unless otherwise noted, technical terms are used according to conventional usage. Definitions of common terms in molecular biology maybe found in e.g., Benjamin Lewin, *Genes IX*, published by Oxford University Press (2007) (ISBN 0763740632); Krebs, et al. (eds.), *The Encyclopedia of Molecular Biology*, published by Blackwell Science Ltd. (1994) (ISBN 0-632-02182-9); and Robert A. Meyers (ed.), *Molecular Biology and Biotechnology: a Comprehensive Desk Reference*, published by VCH Publishers, Inc. (1995) (ISBN 1-56081-569-8).

The term "nucleic acid consisting essentially of", "polynucleotide consisting essentially of", and "RNA consisting essentially of", and grammatical variations thereof, means a polynucleotide that differs from a reference nucleic acid sequence by 20 or fewer nucleotides and also perform the function of the reference polynucleotide sequence. Such variants include sequences which are shorter or longer than the reference nucleic acid sequence, have different residues at particular positions, or a combination thereof.

The terms "approximately" and "about" refer to a quantity, level, value or amount that varies by as much as 30% in one embodiment, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

For some examples below, the altered NDV is a velogenic NDV (ZJ1 strain) that has been altered to become attenuated. In other examples below, the altered NDV is a lentogenic LaSota strain that has low pathogenicity. For the examples using an attenuated ZJ1 strain NDV, virulent NDV (vNDV) ZJ1 (Goose/China/ZJ1/2000; GB AF431744.3), a genotype VIId virus, is used as a challenge virus in the in-ovo vaccination experiments. vNDV CA02 (gamefowl/US(CA)/212676/2002; GB EF520718.1) is used as heterologous (genotype V) challenge virus for the vaccination experiment performed in 4-week-old chicken. NDV strain LaSota (LS) is used worldwide as a live or inactivated vaccine and is used as a comparison vaccine in the immunization-challenge experiments. Recombinant ZJ1*L (ZJ1*L) is an attenuated version of NDV ZJ1 and its generation is described below. ZJ1*L is used as a comparison vaccine for all the characterization and immunization experiments described below. All NDV are propagated and titrated in 9-11 day-old specific-pathogen-free (SPF) embryonating chicken eggs (ECEs).

All 9-day old to 11-day-old ECEs and white leghorn chickens are obtained from the Southeast Poultry Research Laboratory (SEPRL, USDA-ARS, Athens, Ga.) SPF flocks. Birds are bred in brooder cages and transferred into negative pressure isolators either in Biosecurity Level 2 Enhanced (BSL-2E) or BSL-3E animal facilities before starting any vaccination and or challenge experiment. Birds are provided food and water ad libitum.

HI antibody titers and virus titers are expressed as arithmetic means plus or minus the standard error of the mean for each group of vaccinated birds. Animals negative for HI are also included in the group mean. Group means are analyzed by ANOVA and Tukey's test for multiple comparisons when appropriate, and using Student's t-test when comparing only two groups at a time. The survival curves are analyzed using the log-rank test. The level of significance used to determine statistical differences among groups is 5% ($\alpha$=0.05).

Example 1. Generation of Attenuated, Recombinant NDV Expressing Anti-Sense chIL-4 (ZJ1*L/IL-4R)

The cds of chIL-4 is obtained from GenBank accession number NM_001007079.1; see SEQ ID NO: 1. Total RNA of bacterial cells is isolated, and a cDNA of chIL-4 is generated using the SuperScript III One-Step RT-PCR System with Platinum Taq DNA polymerase kit (Invitrogen, Carlsbad, Calif.) according to the manufacturer's recommended protocol. Forward primer (5'-ctgggccctcttagaaaaaatacgggtagaagtaccATGAGCTCCTCACTGCCCA-3' SEQ ID NO: 6) and reverse primer (5'-ggccggttgggccctcgttTCACTTATTTTTAGCTAGTTGGTGGAAGAAGG-3' SEQ ID NO: 7) are used to generate the amplicon. The amplicon contains sequences corresponding to the NDV genome intergenic regions located between the genes P and M and the 411 nt of the chIL-4 cds (lower case letters are modified NDV sequences, capital letters are IL-4 sequences). The amplicon is purified prior to PCR and PCR conducted under standard conditions to amplify the IL4 coding sequence flanked by NDV sequences. The produced amplicon is cloned into the pCR2.1 vector (Invitrogen, Carlsbad, Calif.) at the TA site and then digested with the Apa I enzyme, and the correct sequence is confirmed by Sanger sequencing using an ABI sequencer (Carlsbad, Calif.). The "gene start" (GS) (SEQ ID NO: 8), "gene end" (GE) (SEQ ID NO: 9), and the ApaI restriction sites sequences are added to chIL-4 cds by PCR amplification using the High Fidelity PCR kit (Promega, Madison, Wis.) according to manufacturer's recommended protocol. An additional stop codon is inserted at the end of the chIL-4 open reading frame to maintain the number of nucleotides between the two ApaI sites as a multiple of six. (The length of any nucleic acid inserted into Newcastle disease virus needs to be a multiple of six for the virus to be able to replicate effectively.) The resulting plasmid is named pCRIL-4.

The plasmid pNDV/ZJ1 contains the entire genomic sequences of the wild type NDV ZJ1. See, Liu, et al., *Archives Virology,* 152:1241-1249 (2007). pNDV/ZJ1 is used as a backbone to construct the altered NDV containing an anti-sense chIL-4 cds. Briefly, the Fusion protein cleavage site from pNDV/ZJ1 is attenuated through site directed mutagenesis using the Phusion Site-Directed Mutagenesis kit (New England Biolabs, Inc., Ipswich, Mass.) according to the manufacturer's recommended protocol, generating pNDV/ZJ1*L. See Table 1, infra, for the amino acid mutation generated, and SEQ ID NO: 16 for the DNA sequence of pNDV/ZJ1*L. The genome of the altered NDV made from pNDV/ZJ1*L has a sequence that is the reverse, complementary RNA equivalent of SEQ ID NO: 16.

The 2857-5637 region of the genome is amplified from pNDV/ZJ1*L, via PCR using forward primer FwZJ1_2849 (5'-aacgctctagaGGGTGAAATGACGCTCAATA-3' (SEQ ID NO: 26)) and reverse primer RvZJ1_5283 (5'-cgtgcaagcttTTGCCACCAGCTAAATTA-3' (SEQ ID NO: 27)) which are homologous to the ZJ1 virus, and cloned by blunt end ligation into pCR2.1 (Invitrogen, Carlsbad, Calif.) using manufacture's recommended protocol. This 2857-5637 nt region is sub-cloned into pUC19 (Invitrogen, Carlsbad, Calif.) using the HindIII and XbaI restriction enzymes of the pCR2.1 polylinker resulting in pUCZJ1. The chIL-4 cds is then transferred from pCRIL-4 into pUCZJ1 by ligation of the insert through the unique ApaI restriction site existing in pUCZJ1. As a result of this ligation, the chIL-4 is placed in the reverse orientation between two NDV genomic regions, and the resulting plasmid is named pUCZJ1-IL-4R. The pUCZJ1-IL-4R plasmid is then digested with AgeI and PsiI restriction enzymes to replace the modified construct into the AgeI and PsiI sites on the vector according to manufacturer's recommended protocol. Thus, the polynucleotide containing chIL-4 with GS, GE, and ApaI restriction sites is ligated into plasmids, digested, isolated on an agarose gel, ligated into the full-length pNDV/ZJ1*L between the P and M genes of the ZJ1 genome, within the untranslated regions (UTRs) of the P gene, and is named pNDV/ZJ1*L-IL-4R (SEQ ID NO: 17) and contains SEQ ID NO: 3. See, also, Susta, et al., *Microbial Pathogenesis,* 61-62:73-83 (2013), and Cardenas-Garcia, et al., PLOS ONE, 11(7):e0159153 (2016), the contents of which are incorporated herein.

The altered NDV, ZJ1*L/IL-4R, is generated using plasmid rescue techniques using pNDV/ZJ1*L-IL-4R. The plasmid containing the NDV genome with the anti-sense IL-4 and the auxiliary plasmid that are normally used to rescue NDV (nucleocapsid, phosphoprotein and polymerase expressing plasmids; see, Peeters, et al., *J. Virol.* 73(6):5001-5009 (1999)) are transfected into Hep-2 cells grown and maintained in Dulbeco's Modified Eagle Medium (DMEM) (Corning Cellgro, Invitrogen, Carlsbad, Calif.), supplemented with 5% Fetal Bovine Serum (FBS) and antibiotics (100 U/ml penicillin and 100 µg/ml streptomycin), at 37° C. with a 5% $CO_2$ atmosphere as described in Cardenas-Garcia, et al. (2015). The rescued virus is designated as ZJ1*L/IL-4R (with a sequence that is the reverse, complementary RNA equivalent of SEQ ID NO: 18 (which contains SEQ ID NO: 3)) and further subjected to RNA extraction, RT-PCR and sequencing to confirm its identity and that the attenuation mutation in F protein cleavage site.

Example 2 ZJ1*L/IL-4R In-Vivo Characterization

One characterization of ZJ1*L/IL-4R is intracerebral pathogenicity index (ICPI) assay. For this assay, one day-old SPF hatchling chicks are inoculated intracerebrally with 50 µl of a 1:10 dilution of allantoic fluid (AF) harvested from embryonating chicken eggs (ECEs) infected with NDV virus strains vZJ1, LS, ZJ1*L (attenuated), and ZJ1*L/IL-4R (see Example 1). Birds are monitored every 24 hours during 8 days and scored as follows: 0=normal, 1=sick or 2=dead. An equation is used to calculate the ICPI and any virus with a value ≥0.7 is considered virulent. See, Alexander and Senne, *Newcastle Disease and other Paramyxoviruses*, in *A Laboratory Manual for the Isolation Identification and Characterization of Avian Pathogens*, (5th ed.) Swayne, et al., (eds.), OmniPress, Inc., 135-141 (2008) and OIE World Organization for Animal Health, *Manual of diagnostic tests and vaccines for terrestrial animals*, in *Book Manual of Diagnostic Tests and Vaccines for Terrestrial Animals* (2012). Results are presented in Table 1, infra.

Another characterization of ZJ1*L/IL-4R is mean death time (MDT) assay. Nine to eleven day-old SPF ECEs are inoculated as described supra with vZJ1, LS, ZJ1*L and ZJ1*L/IL-4R. Allantoic fluids are harvested after death or at the end of the experimental period (6 days post-inoculation)

from chilled eggs and used to determine virus titers by HI31 assay and using the Spearmann-Karber method to calculate the $EID_{50}$ per ml. See, Karber G., *Arch. Exp. Pathol. Pharmak.,* 162:480-483 (1931). Results are presented in Table 1, infra.

TABLE 1

| Virus Strain | ICPI[a] Value | MDT[b] (hours) | MLD[c] ($EID_{50}$/0.1 mL) | Fusion Protein Amino Acid Cleavage Site |
|---|---|---|---|---|
| PBS | 0.00 | — | — | — |
| LS-wt[d] | 0.30 | 153.25 | $10^6$ | $_{112}$GRQGRL$_{117}$ (SEQ ID NO: 10) |
| LS/IL-4R | 0.30 | >175 | Undetermined | $_{112}$GRQGRL$_{117}$ (SEQ ID NO: 10) |
| ZJ1*L | 0.35 | >175 | Undetermined | $_{112}$GRQGRL$_{117}$ (SEQ ID NO: 10) |
| ZJ1*L/IL-4R | 0.25 | >175 | Undetermined | $_{112}$GRQGRL$_{117}$ (SEQ ID NO: 10) |
| vZJ1 | 1.83 | 54.5 | $10^8$ | $_{112}$RRQKRF$_{117}$ (SEQ ID NO: 11) |

[a]Intracerebral pathogenicity index
[b]Mean death time in eggs
[c]Mean lethal dose
[d]Wild-type LS In summary, ZJ1*1/IL-4R has ICPI value compatible with NDV strains of low virulence (0.25), while the parental virulent virus (vZJ1) exhibited high ICPI (1.83). The cleavage site for ZJ1*1/IL-4R is confirmed to be identical to the low virulence cleavage site from the LS strain ($_{112}$GRQGRL$_{117}$) (SEQ ID NO: 10). Furthermore, the MDT value for ZJ1*L/IL-4R (>175 hrs.) confirms its classification as low virulent NDV.

The third characterizing assay of ZJ1*L/IL-4R is examining impaired expression of chIL-4 in ECEs. Ten-day-old ECEs are inoculated with 1:1000 dilution of AF infected with ZJ1*L or ZJ1*L/IL-4R, and incubated for 6 days at 37° C. Fluids are collected, and HA tested to confirm infection. Thereafter, clean AF, AF from ECE infected with ZJ1*L, and AF from ECE infected with ZJ1*L/IL-4R are analyzed for chIL-4 expression through Western blotting using 8-16% polyacrylamide gels (Bio-Rad, Hercules, Calif.) and anti-chIL-4 polyclonal antibodies (Cloud-Clone Corp, Houston, Tex.; and Wuhan USCN Life Science Inc., Wuhan, Conn.) using manufacturer's recommended protocol. Additionally, anti-chicken IL-4 ELISA test is performed to assess for the presence of chIL-4 (USBiological Life Sciences, Salem, Mass.) from diluted (1:16 and 1:32) in ZJ1*L and ZJ1*L/IL-4R-infected AFs using manufacturer's recommended protocol. Decreasing levels of chIL-4 are detected in the ZJ1*L/IL-4R-infected AF compared to the ZJ1*L-infected AF (FIG. 1). This observation suggests that the anti-sense ZJ1*L/IL-4R is inhibiting production of chIL-4 in viral-infected ECEs.

Example 3 ZJ1*L/IL-4R In-Ovo Vaccination

In order to determine the capabilities of ZJ1*L/IL-4R as an in-ovo vaccine and its effect on immune response modulation, 18-19-day-old SPF ECEs are vaccinated. The effect of administration of the immunogenic composition at two different embryo stages (18 and 19 doe), and the effect of multiple doses of the immunogenic compositions, including ZJ1*L/IL-4R and the commercially available LS strain, are evaluated. These assays allow assessment of several important parameters for an effective in-ovo vaccine, survival rate after hatching. The results of these assays are in FIGS. 2A, 2B, 2C and 2D.

Fresh (less than 24 hours old) eggs laid by SPF White Leghorn chicken are collected and washed, then incubated until 18-19 days of embryonation (doe). At 18 or 19 doe, ECEs are randomly assigned to either one of four groups: 1) brain and heart infusion (BHI) (negative control), 2) LS, 3) ZJ1*, and 4) ZJ1*L/IL-4R. Different doses of the immunogenic compositions are evaluated ($10^{3.5}$, $10^{4.5}$, $10^5$ and $10^{7.5}$ $EID_{50}$ per egg mixed with BHI broth). Regardless of the treatment, eggs are manually inoculated with 100 μl of the corresponding immunogenic composition or uninfected inoculum through the amniotic route or the intraembryonic route, using 1 mL syringes with 24 G×½". After vaccination, each group of vaccinated eggs are placed in an incubator (2362E Turbofan Hova-Bator Incubator by GQF, Savannah, Ga.). Each incubator is placed inside a BSL2 isolator. Temperature and humidity are monitored until 21 doe and are kept at approximately 99.5° F. and between 65% and 73%, respectively. After hatching, hatchling chicks are monitored daily for survival and clinical signs until 14 dph. At 14 dph, 12 chickens from each group are individually identified, and serum is collected for serology. Thereafter, these birds are challenged with $10^{4.9}$ $EID_{50}$/bird of vZJ1 by the oculo-nasal route (100 μl). Challenged chickens are monitored daily for two weeks after challenge for clinical signs (depression, swelling of the head, conjunctivitis, and neurological signs) and mortality. Oropharyngeal and cloacal swabs are taken at 2 dpc and 4 dpc. Two weeks after challenge, the remaining birds are bled for post-challenge serology and euthanized. Pre-challenge and post-challenge antibody titers are determined by HI assay. See, Alexander and Senne, *Newcastle Disease and other Paramyxoviruses*, in *A Laboratory Manual for the Isolation Identification and Characterization of Avian Pathogens*, (5th ed.) Swayne, et al., (eds.), OmniPress, Inc., 135-141 (2008) and OIE World Organization for Animal Health, *Manual of diagnostic tests and vaccines for terrestrial animals*, in *Book Manual of Diagnostic Tests and Vaccines for Terrestrial Animals* (2012).

Figure 2A:
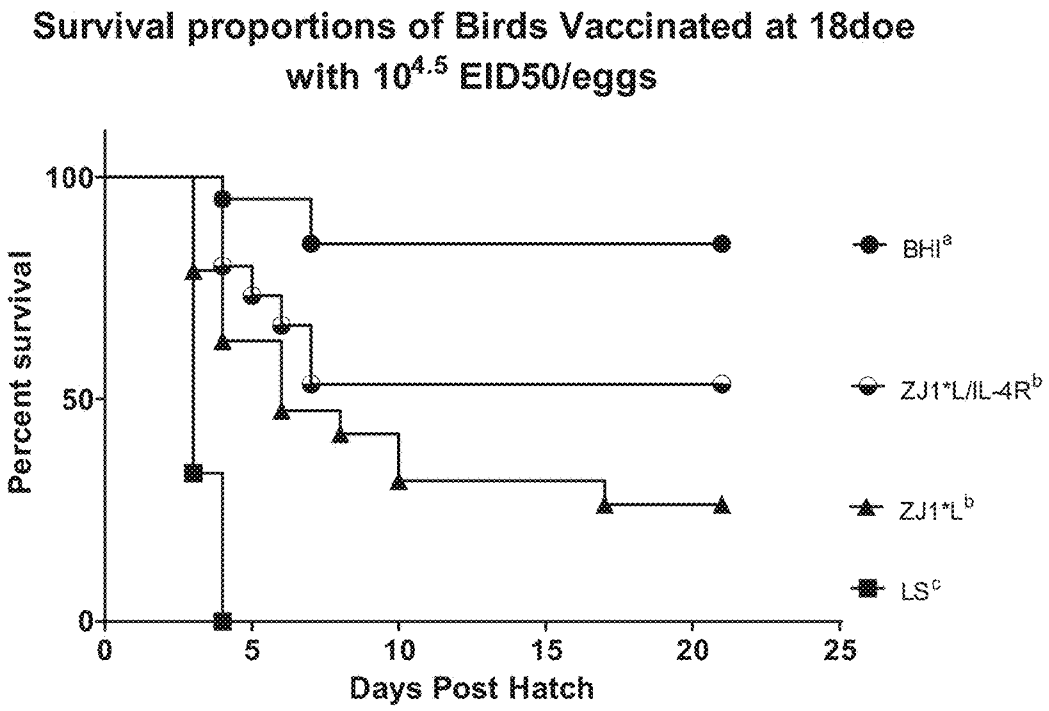
FIGS. 2A, 2B, 2C, and 2D show the survival of hatchling chicks after in-ovo vaccination with brain and heart infusion (BHI; negative control/sham vaccine), ZJ1-L, a LaSota strain NDV (LS), or ZJ1*L/IL-4R at different doses.
Figure 2B:
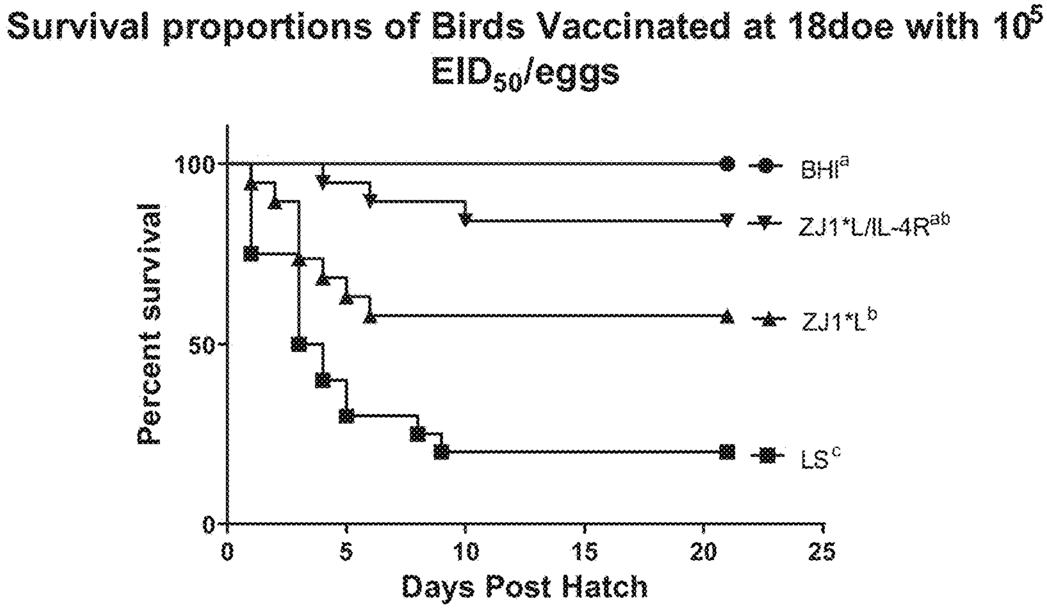
Figure 2C:
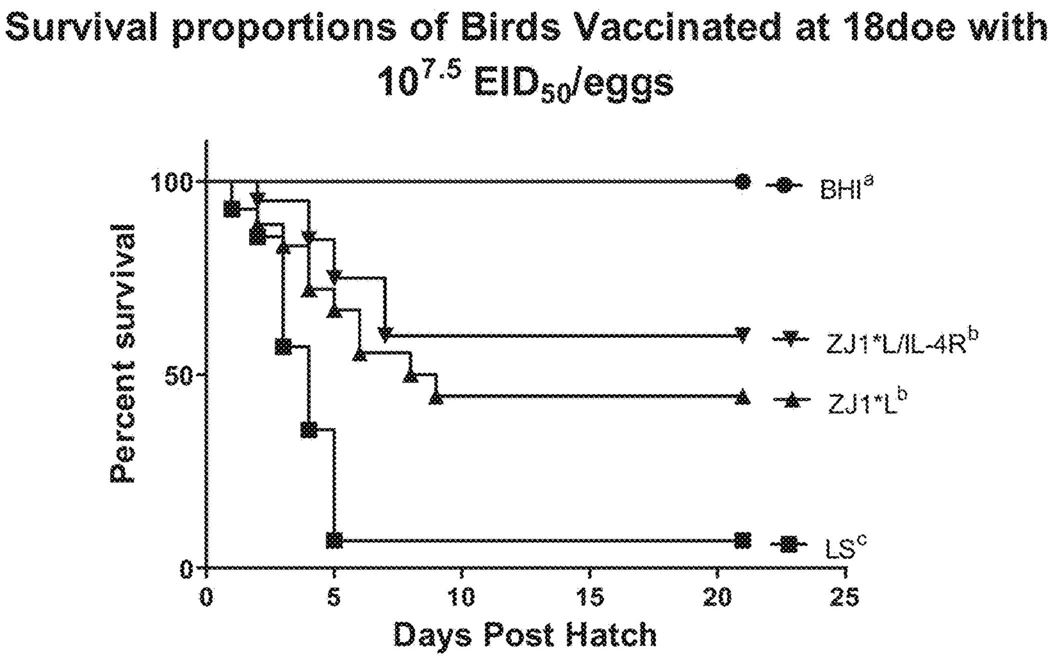
Figure 2D:
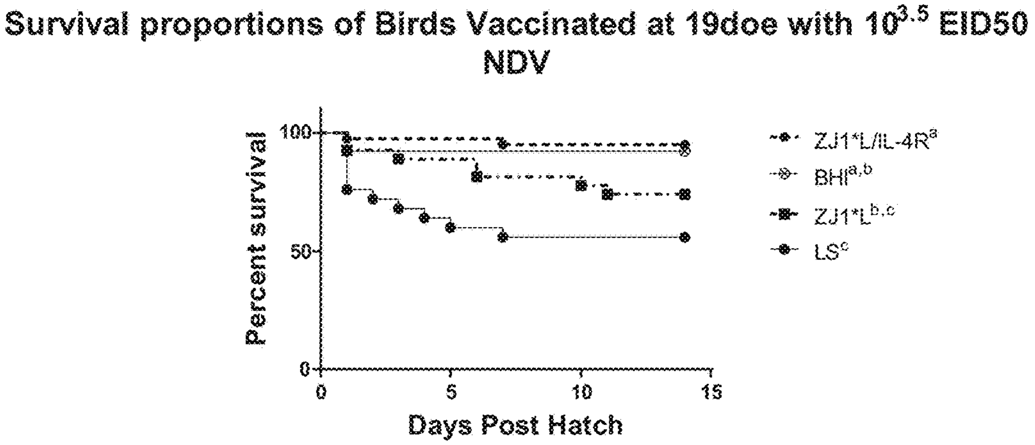

As shown in FIGS. 2A-2D, the best survival rate after 14 dph is always achieved by the sham-vaccinated control (BHI), closely followed by ZJ1*L/IL-4R. The group with the worst survival rate received LS virus for each vaccination protocol. Vaccinating ECEs at 19 doe with an $EID_{50}$/egg of $10^{3.5}$ with ZJ1*L/IL-4R yields the best survival rates (FIG. 2D). The results of administering a 10× dose ($10^{4.5}$) demonstrates the safety of ZJ1*L/IL-4R administered via an in-ovo route (FIG. 2A).

Figure 3:
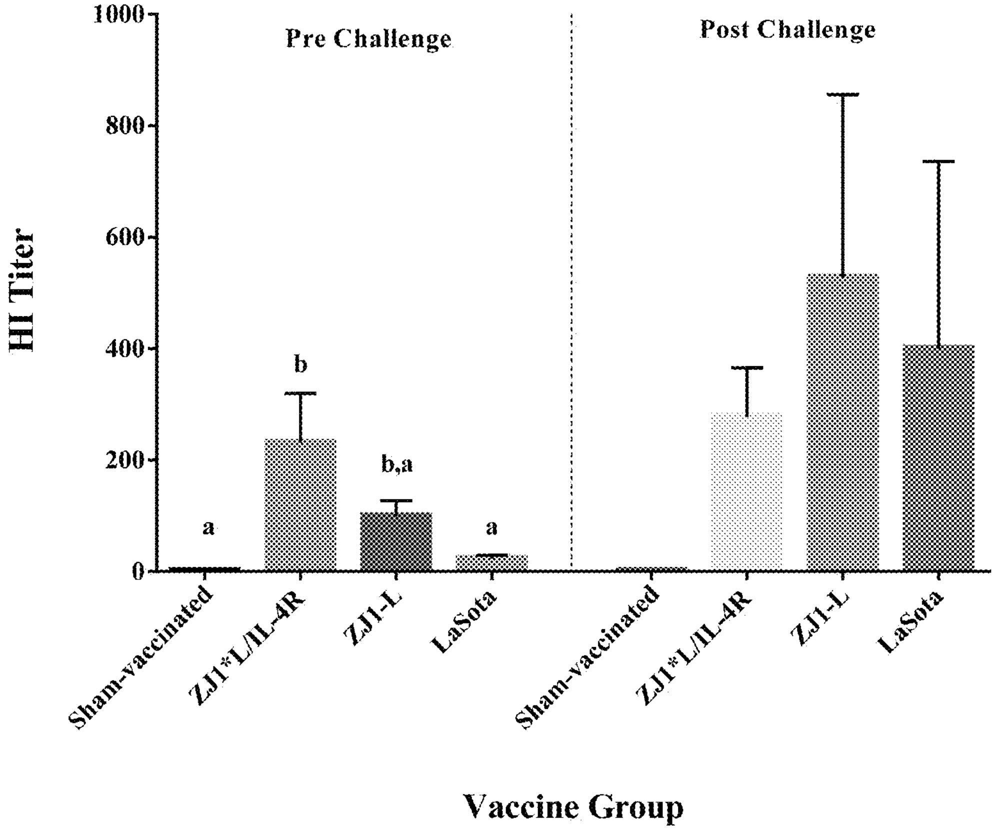
FIG. 3 illustrates the effect of in-ovo vaccination with LS, ZJ1*L, ZJ1*L/IL-4R, or BHI (negative control) at $10^{3.5}$ $EID_{50}$ per egg at 19 doe on pre- and post-challenge antibody titers using a hemagglutinin inhibition (HI) assay. Serum samples are collected at 14 dph (days post-hatch) (pre-challenge) and 16 dpc (days post-challenge). Columns sharing letters are not significantly different from one another after analyzed with the Tukey's test for multiple comparisons with a level of significance of 5%.
Figure 4:
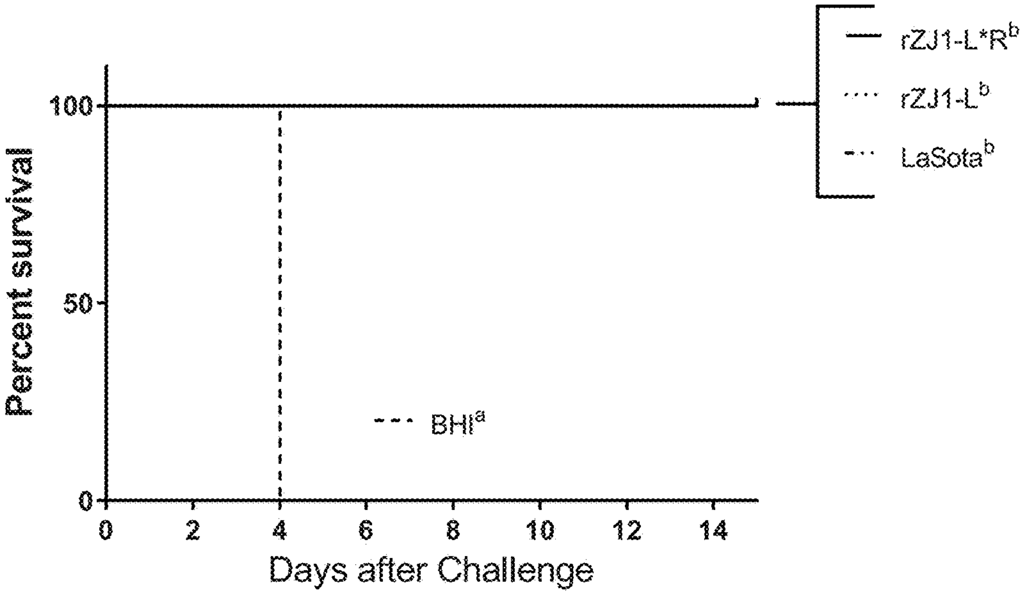
FIG. 4 illustrates the survival of in-ovo vaccinated hatchling chick after challenge with vNDV at 14 dph. Survival curves are analyzed using the Long-Rank test. Curves sharing letters are not significantly different from one another.
Figure 5A:
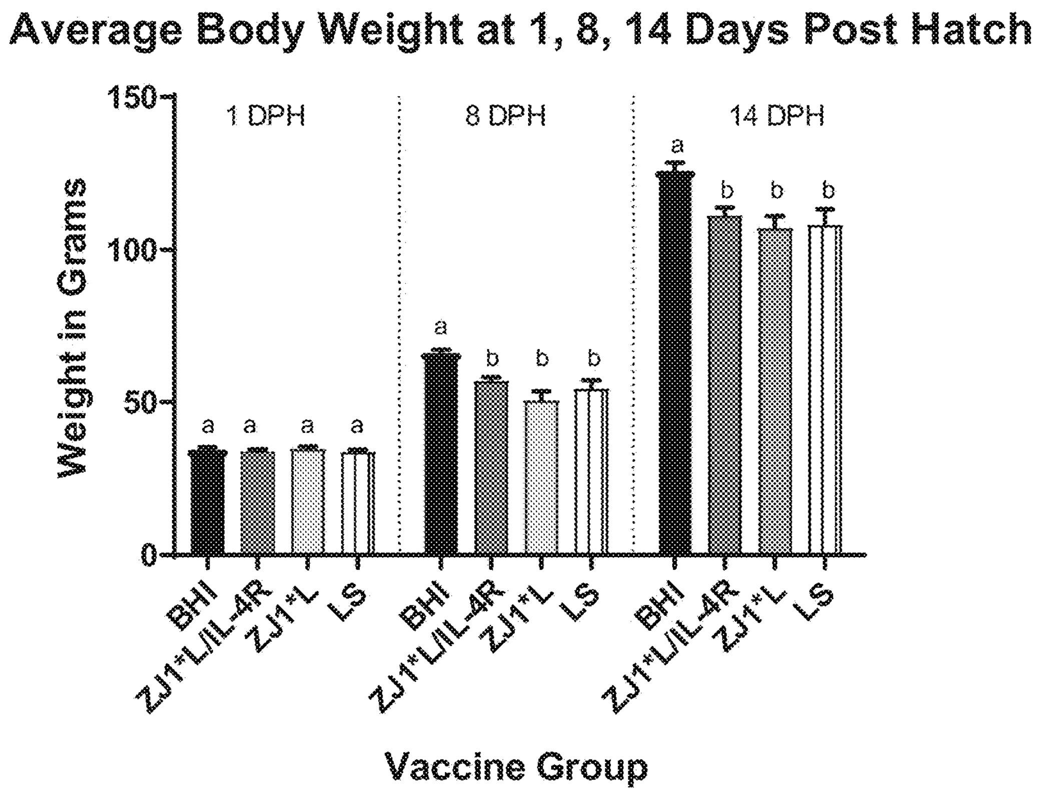
FIGS. 5A and 5B compare the effect of the indicated viruses (LS, ZJ1*L, ZJ1*L/IL-4R, or BHI) on the weight of in-ovo vaccinated hatchling chicks before and after vNDV challenge.
Figure 5B:
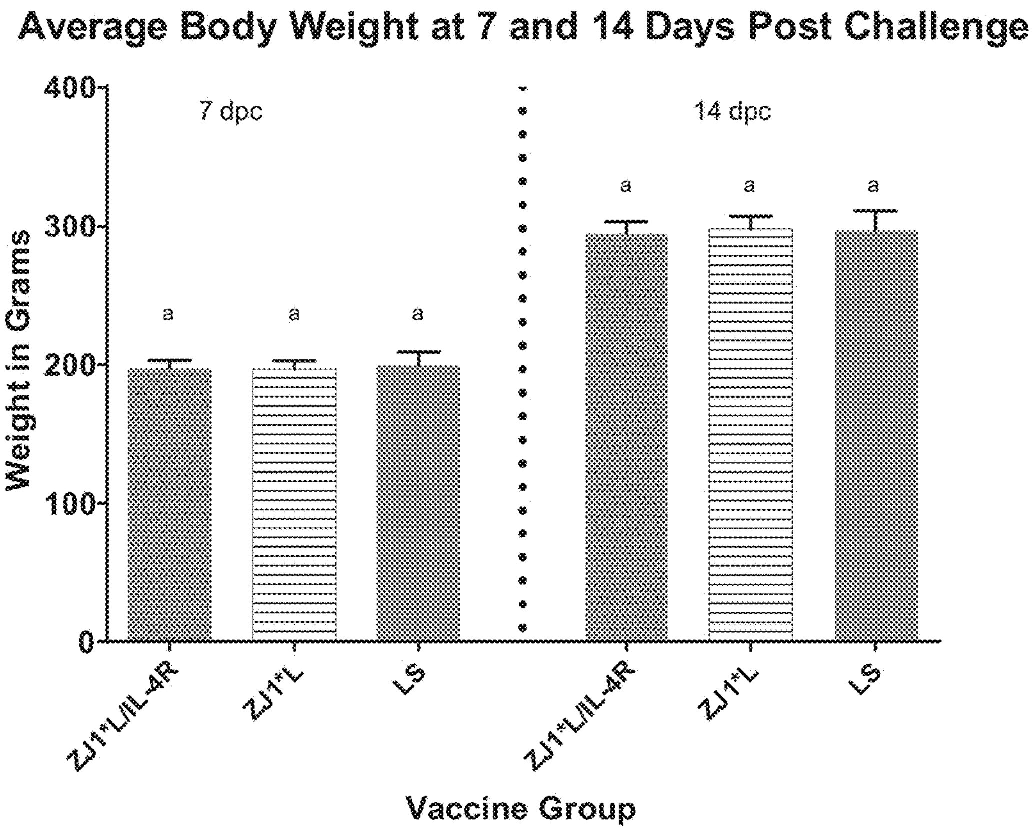

After determining the best stage of embryonation vaccine administration in-ovo and a dosage that results in high survival after hatching, antibody titers (HI assay), survival rates, and body weight before (14 dph) and after challenge with vZJ1 (16 dpc) are evaluated. As shown in FIG. 3, pre-challenge antibody titers for the sham-vaccinated, ZJ1-L, and LS groups are not significantly different from one another. However, antibody titers for the ZJ1*L-IL-4R vaccinated group are significantly higher than sham (BHI) vaccinated and LS vaccinated groups, but not significantly different from the ZJ1-L vaccinated group (FIG. 3). In-ovo vaccinated chickens are challenged with vNDV ZJ1 two weeks after hatching and followed until 14 days after challenge. Although the antibody titers in the ZJ1-L and LS groups are not significantly higher than the antibody titers of the unvaccinated birds, a 100% protection against mortality after challenge is achieved. As shown in FIG. 4, the sham (BHI) vaccinated group reach 100% mortality by 5 dpc, whereas all other vaccinated birds survive challenge without signs of clinical disease (100% survival). Additionally, birds are weighed at 1, 8, 14 dph (pre challenge). At 1 dph all body weights per group are not significantly different from one another. However, the body weights of birds in ZJ1*L/IL-4R, ZJ1-L and LS groups are statistical different at 8 dph and 14 dph from the body weight of the chickens that received BHI. See FIG. 5A. Body weight is also recorded at 7 dpc and 14 dpc, but no significant differences are found between chickens in the ZJ1*L/IL-4R, ZJ1-L and LS groups. See FIG. 5B. Because all the sham-vaccinated birds succumbed by day 5 after challenge, and the post-challenge body weights are recorded subsequent to 5 dpc, no information is available for this group at 7 dpc and 14 dpc.

In conclusion, the ZJ1*L/IL-4R altered virus generates the best survival rates of in-ovo vaccinated chicks after hatching (especially when the altered virus is administered at 19 doe at a dose of $10^{3.5}$ $EID_{50}$/egg). Further, the altered virus does not negatively impact the body weight of the hatchling chicks, but it induces higher antibody titers after vaccination with lower antibody titer increment after challenge compared to in-ovo vaccination with LS or ZJ1*L. The minimal increase in antibody titers in the ZJ1*L/IL-4R group suggests that the altered virus is effective in controlling replication of the challenge virus.

Figure 7:
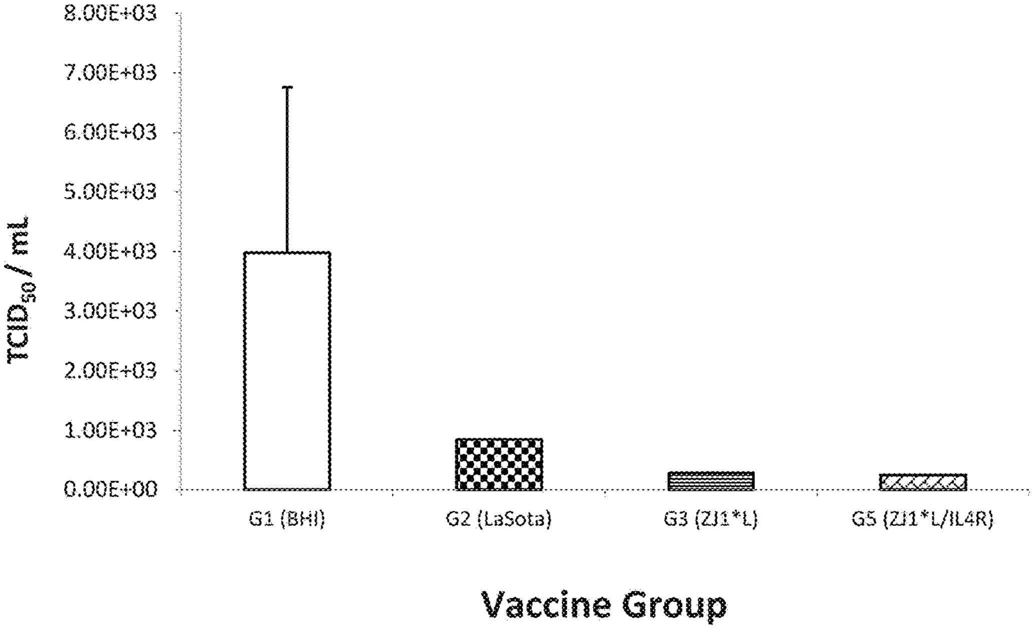
FIG. 7 shows the viral shedding rates of chickens vaccinated at 4 weeks of age with BHI, LS, ZJ1*L, or ZJ1*L/IL-4R after being challenged with vNDV strain CA02.

Example 4 Vaccination of 4-Week Old SPF Chickens with Live ZJ1*L/IL-4R Altered Virus The potential usage of ZJ1*L/IL-4R (genotype VIId) as a live vaccine for juvenile chickens is also evaluated. Forty-four 4-week-old SPF white leghorn chickens are vaccinated and then challenged 2 weeks after vaccination. Birds are vaccinated with 100 μl of either BHI only (sham vaccinated, negative control), live LS with BHI broth, live ZJ1*L with BHI broth, or live ZJ1*L/IL-4R with BHI broth by ocular instillation and choanal cleft (50 μl each route) at 4 weeks of age. The intended titer for each vaccine is $10^{6.5}$ $EID_{50}$/bird. Two weeks after vaccination, all birds are challenged with virulent NDV CA02 (genotype V virus) at $10^{6.5}$ $EID_{50}$/bird. Oropharyngeal and cloacal swab samples are collected at 2 dpc for determination of challenge virus shedding. Viral shedding is determined by virus isolation in 10-week old SPF ECEs; titrations are performed in DF-1 cell cultures and reported as $TCID_{50}$/mL using the Spearmann-Karber method as described in Karber, G. (1931). See FIG. 7. Mortality and clinical signs are recorded until 14 dpc.

Figure 6:
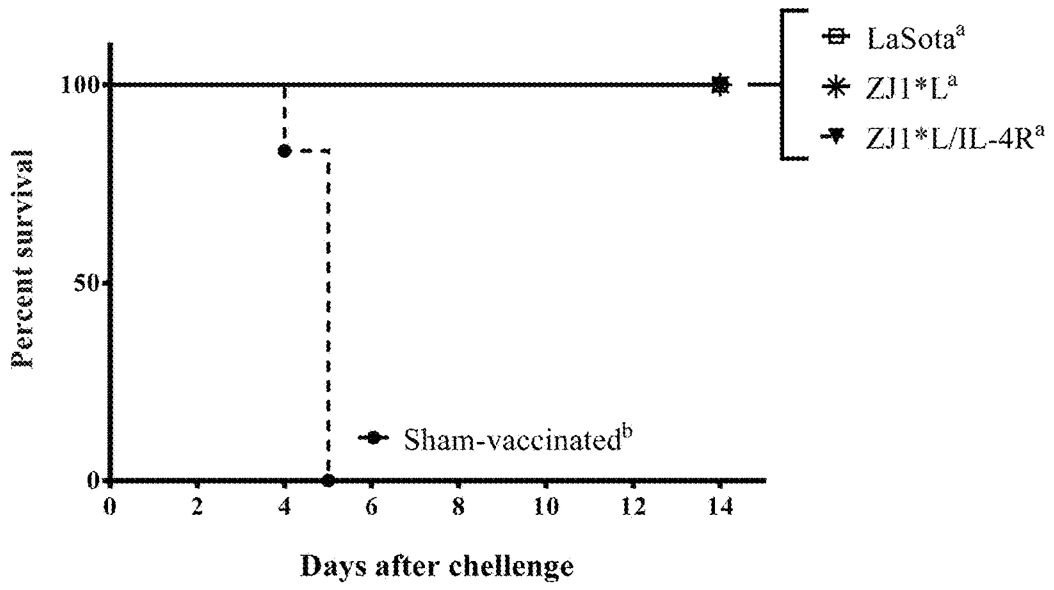
FIG. 6 shows the survival rate of chickens vaccinated at 4 weeks of age with BHI (sham vaccinated), LS vaccine, ZJ1*L, or ZJ1*L/IL-4R after being challenged with vNDV CA02. Survival curves are analyzed using the Long-Rank test. Curves sharing letters are not significantly different from one another.

All vaccinated birds, regardless of the NDV vaccine administered, survive the challenge compared to the sham-vaccinated group for which 100% of the birds succumbed by 5 dpc. See FIG. 6. The amount of virus shed by all birds in the NDV vaccinated groups significantly decreased compared to the sham-vaccinated birds. No statistically significant difference between vaccinated groups are found, but the group of birds that received LS has higher shedding rate than those birds that received either ZJ1*L or ZJ1*L/IL-4R. See FIG. 7. In summary, ZJ1*L/IL-4R is effective, producing 100% protection, and significantly reducing viral shedding of a different genotype NDV.

The results of the above examples demonstrate that ZJ1*L/IL-4R (an altered NDV) is a reliable in-ovo immunogenic composition that modulates the host animal's immune response and induces good protection in the host upon challenge. ZJ1*L/IL-4R administered in-ovo to a bird induces higher antibody titers compared to the antibody titers in birds that received LS or ZJ1*L (see FIG. 3). In addition, vaccination of chicken embryos with ZJ1*L/IL-4R at 19 days of embryonation results in better survival of the birds after hatching compared to the other vaccinated groups (see FIG. 2D). ZJ1*L/IL-4R also reduces the viral shedding compared to the viral shedding by the birds in other vaccination groups (see FIG. 7).

Example 5 Construction of Altered LaSota NDV Expressing Anti-Sense chIL-4 (LS-IL4R)

A LaSota-GFP plasmid (pLS-GFP) containing green fluorescent protein (GFP) coding sequence between the P and M genes (see Zhao, et al. 2015) is used as a backbone to construct a recombinant virus (pLS-IL-4R) expressing chicken IL-4 (chIL-4) anti-sense RNA through a two-step approach using the in-fusion cloning of PCR products that are generated using PfuUltra II Fusion HS DNA polymerase (Agilent Technologies, Santa Clara, Calif.) via homologous recombination. pLS-GFP is propagated in Stbl2 cells at 30° C. for 24 hours and is purified using a QIAprep Spin Miniprep kit (Qiagen, Germantown, Md.) according to manufacturer's recommended protocol. First, a cDNA fragment of the nt 6963-6242 region containing the plasmid and NDV vector sequences (pLS vector) is amplified from pLS-GFP using primers pLSup (5'-GGTGGCTACAACTATCAACTAAACT-3' (SEQ ID NO: 19)) and pLSdown (5'-GTGTGTAACTACCGTGTACTAAGC-3' (SEQ ID NO: 20)) using PfuUltra II Fusion HS DNA polymerase (Agilent Technologies, Santa Clara, Calif.) according to manufacturer's recommended protocol, thereby removing the GFP ORF (nt 6243-6962) from the plasmid. The chIL-4 gene is amplified from the Y2880K-mRNA-N411 plasmid (purchased from Biomatik Wilmington, Del.) using PfuUltra II Fusion HS DNA polymerase (Agilent Technologies, Santa Clara, Calif.) with Anti-IL4 Forward primer (5'-atagttgtagccaccTCACTTATTTTTAGCTAGTTGG-3' (SEQ ID NO: 21)) and Anti-IL4 Reverse primer (5'-acggtagttacacacgtcATGAGCTCCTCACTGCCCAC-3' (SEQ ID NO: 22)). This amplicon containing chIL-4 sequence is run on a gel and purified using QIAprep Spin Miniprep Kit (Qiagen, Gaithersburg, Md.). Note that the lower case letters in Anti-IL4 Forward primer and Anti-IL4 Reverse primer are LS NDV sequences and capital letters are IL-4 sequences. An additional three nucleotides (gtc; underlined) are inserted into the noncoding sequence prior to the beginning of the chIL-4 open reading frame to maintain the "rule of six" (i.e., the length of any nucleic acid inserted into Newcastle disease virus needs to be a multiple of six for the virus to be able to replicate effectively). The amplicon (SEQ ID NO: 23), containing chIL-4 ORF in the reverse complement orientation (anti-sense; SEQ ID NO: 2) and sequences from the primers used (SEQ ID NOs: 19, 20, 21, and 22), is cloned through homologous recombination into the noncoding region downstream of the P gene and upstream of the M gene of the pLS vector, as an additional transcription unit, using the In-Fusion® PCR cloning kit (Takara Bio USA, Inc., Mountain View, Calif.) using manufacturer's recommended protocol. The pLS vector is linearized before each round of homologous recombination. The resultant plasmid is designated pLS-IL-4R (SEQ ID NO: 24).

LS-IL4R (the reverse, complementary RNA equivalent of SEQ ID NO: 25) is generated using plasmid rescue techniques using pLS-IL-4R and auxiliary plasmids that are normally used to rescue NDV (that is, nucleocapsid-, phosphoprotein- and polymerase-expressing plasmids; see, Peeters, et al., *J. Virol.* 73(6):5001-5009 (1999) contents of which are expressly incorporated herein) are transfected into Hep-2 cells grown and maintained in Dulbeco's Modified Eagle Medium (DMEM) (Corning Cellgro, Tewksbury, Mass.; and Thermo Fisher Scientific, Waltham, Mass.), supplemented with 5% Fetal Bovine Serum (FBS) and antibiotics (100 U/ml penicillin and 100 μg/ml streptomycin), at 37° C. with a 5% $CO_2$ atmosphere as described in Cardenas-Garcia, et al. (2015). The rescued virus is designated as LS-IL4R and further subjected to RNA extraction, RT-PCR and sequencing to confirm its identity.

Example 6 LS-IL4R In-Ovo Vaccination

The intracerebral pathogenicity index (ICPI) is determined for LS-IL4R (see Example 5) using the ICPI assay described in Example 2, supra, and compared to the ICPI for LS. The ICPI results are presented in Table 1, supra. The mean death time (MDT) is also determined for LS-IL4R using the MDT assay described in Example 2, supra, and compared to the MDT for LS. The MDT results are presented in Table 1, supra. In summary, LS-IL4R has an ICPI value compatible with NDV strains of low virulence (0.3). The cleavage site for LS-IL4R is confirmed to be identical to the low virulence cleavage site from the LS strain ($_{112}$GRQGRL$_{117}$) (SEQ ID NO: 10). Furthermore, the MDT value for LS-IL4R (>175 hours) confirms its classification as a low virulent NDV.

Using the protocols described above for vaccinating embryonic chicks in-ovo, LS-IL-4R is assessed in SPF eggs. Because vaccinating ECEs at 19 doe with an $EID_{50}$/egg of $10^{3.5}$ with ZJ1*L/IL-4R yields the best survival rates (see FIG. 2D), this strategy for the in-ovo vaccination using LS-IL4R in SPF eggs is used. Fresh (less than 24 hours old) eggs laid by SPF White Leghorn chickens are collected and washed, then incubated until 19 doe. At 19 doe, ECEs are randomly assigned to either one of four groups: 1) brain and heart infusion (BHI) (negative control), 2) LS, 3) LS-RFP (LaSota-red fluorescent protein), and 4) LS-IL4R. Eggs are manually inoculated with 100 μl of $10^{3.5}$ $EID_{50}$/egg and BHI broth of the corresponding immunogenic composition or uninfected inoculum through the amniotic route or the intraembryonic route, using 1 mL syringes with 24 G×½". After vaccination, each group of vaccinated eggs are placed in an incubator (2362E Turbofan Hova-Bator Incubator, GQF, Savannah, Ga.). Each incubator is placed inside a BSL2 isolator. Temperature and humidity are monitored until 21 doe and are kept at approximately 99.5° F. and between 65% and 73%, respectively. After hatching, hatchling chicks are monitored daily for survival and clinical signs until 28 dph. Oropharyngeal and cloacal swabs are taken at 2, 4, 7, 9, 11 and 14 dph. At 14 and 28 dph, birds are bled for serology assays and euthanized; titers are determined by HI assay. See, Alexander and Senne, *Newcastle Disease and other Paramyxoviruses*, in *A Laboratory Manual for the Isolation Identification and Characterization of Avian Pathogens*, (5th ed.) Swayne, et al., (eds.), Omni-Press, Inc., 135-141 (2008) and OIE World Organization for Animal Health, *Manual of diagnostic tests and vaccines for terrestrial animals*, in *Book Manual of Diagnostic Tests and Vaccines for Terrestrial Animals* (2012).

Figure 8:
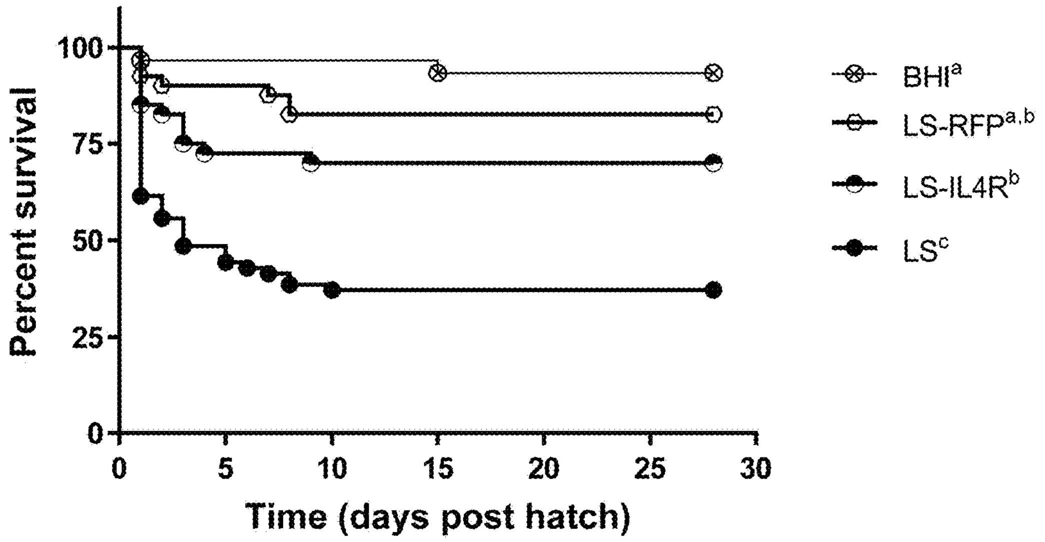
FIG. 8 shows the survival rate (percent survival) of hatchling chicks after in-ovo vaccination with BHI, LS-RFP (LaSota NDV expressing red fluorescent protein), LS-IL4R, and LS NDV at $10^{3.5}$ $EID_{50}$ per egg at 19 doe. Curves sharing letters are not significantly different from one another when analyzed using the Long-Rank test at a level of significance of 5%.

FIG. 8 shows the survival rate (percent survival) of hatchling chicks after in-ovo vaccination with BHI, LS-RFP, LS-IL4R, and LS at $10^{3.5}$ $EID_{50}$ per egg at 19 doe. Curves sharing letters are not significantly different from one another when analyzed using the Long-Rank test at a level of significance of 5%. Birds vaccinated with BHI, LS-RFP, LS-IL4R, or LS had survival rates of 97%, 82.5%, 70%, and 37.5%, respectively. The survival rates of birds immunized with LS-RFP and LS-IL4R are not significantly different from each other; however they are both significantly different from LS immunized birds (as determined using the Long-Rank test at a level of significance of 5%).

Figure 9A:
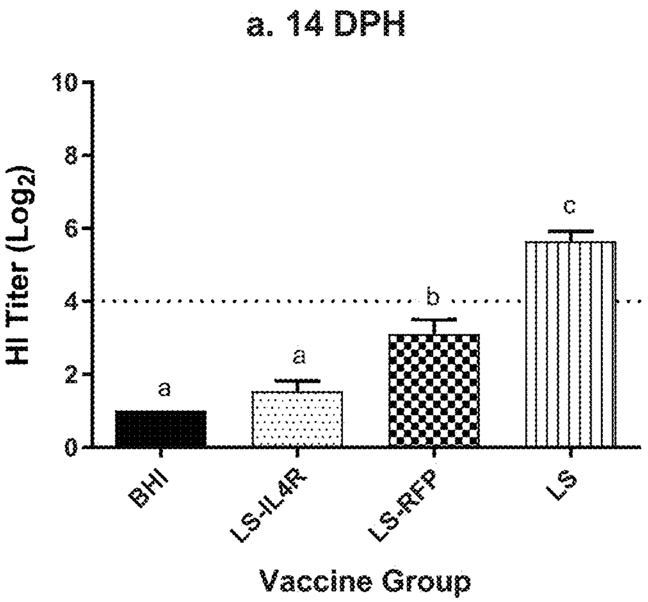
FIG. 9A and FIG. 9B show the effect of in-ovo vaccination with BHI, LS-IL4R, LS-RFP, and LS NDV at $10^{3.5}$ $EID_{50}$ per egg at 19 doe on antibody titers using a HI assay at 14 dph (FIG. 9A) and 28 dph (FIG. 9B). Significant differences between groups are denoted by different letters; columns sharing letters are not significantly different from one another after being analyzed with the Tukey's test for multiple comparisons with a level of significance of 5%.
Figure 9B:
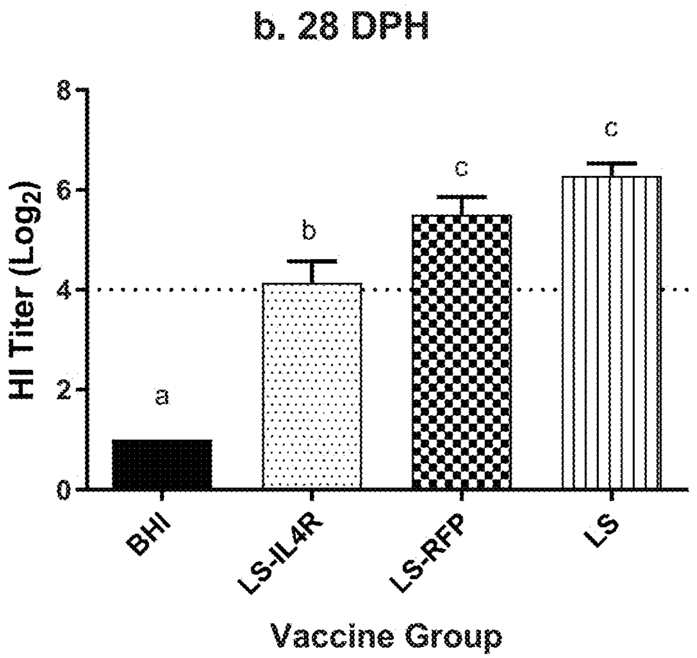

FIG. 9A and FIG. 9B show the effect of in-ovo vaccination with BHI, LS-IL4R, LS-RFP, and LS at $10^{3.5}$ $EID_{50}$ per egg (mixed with BHI broth) at 19 doe on antibody titers using a HI assay at 14 dph (see FIG. 9A) and 28 dph (see FIG. 9B). At 14 dph, the HI titers of the LS-IL4R ($2^{1.5}$), LS-RFP ($2^{3.1}$) and LS ($2^{5.6}$) vaccine groups are all significantly different from one another using the Tukey's test for multiple comparisons with a level of significance of 5%. The average HI titers of the LS-IL4R and LS-RFP vaccine groups are below the threshold normally considered protective for NDV. At 28 dph, the HI titers of the LS-IL4R ($2^{4.1}$) vaccine group are significantly lower that the HI titers of the LS ($2^{6.3}$) vaccine group. The HI titers of the LS-RFP ($2^{5.5}$) vaccinated birds are not significantly different from the HI titers of the LS vaccinated group. Significant differences between groups are denoted by different letters; columns sharing letters are not significantly different from one another after being analyzed with the Tukey's test for multiple comparisons with a level of significance of 5%.

Figure 10A:
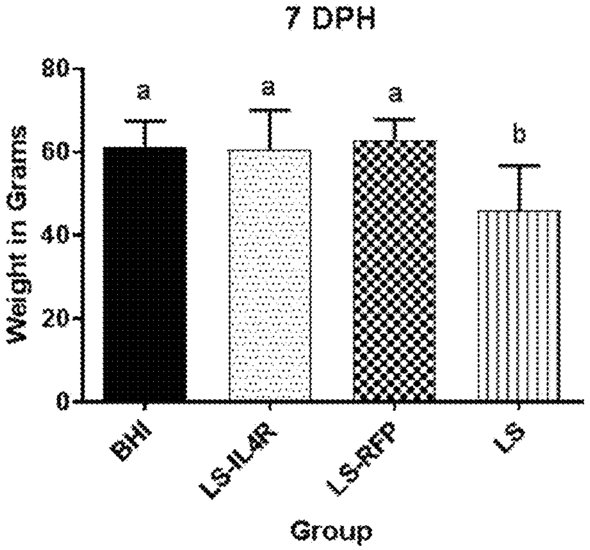
FIGS. 10A, 10B, and 10C compare the effect of BHI, LS-IL4R, LS-RFP, and LS NDV at $10^{3.5}$ $EID_{50}$ per egg at 19 doe on the average body weight of in-ovo vaccinated hatchling chicks at 7 days dph (FIG. 10A), day 14 dph (FIG. 10B), and day 21 dph (FIG. 10C). Significant differences between the groups are denoted by different letters; columns sharing letters are not significantly different from one another after being analyzed with the Tukey's test for multiple comparisons with a level of significance of 5%.
Figure 10B:
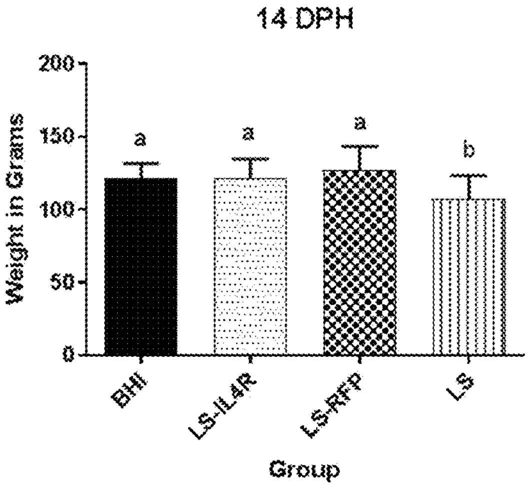
Figure 10C:
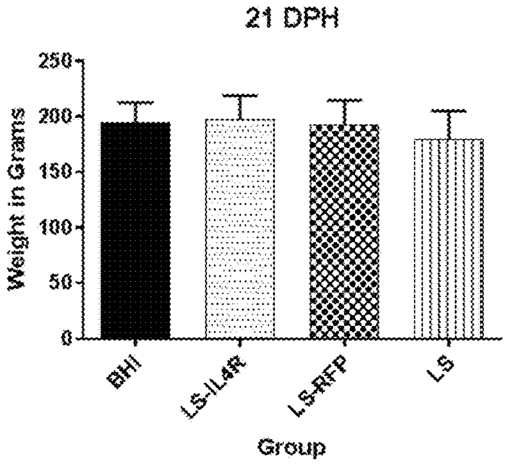

FIGS. 10A, 10B, and 10C compare the effect of BHI, LS-IL4R, LS-RFP, and LS on the average body weight of in-ovo vaccinated hatchling chicks at 7 days dph (FIG. 10A), day 14 dph (FIG. 10B), and day 21 dph (FIG. 10C). LS-IL4R, LS-RFP, and LS (mixed with BHI broth) are administered in the amount of $10^{3.5}$ $EID_{50}$ per egg at 19 doe. At 7 dph, the average body weights of birds vaccinated with BHI (61.43 g), LS-IL4R (60.75 g), or LS-RFP (63.06 g) are not significantly different from one another. Birds vaccinated with LS had average body weights (46.04 g) that are significantly lower compared to BHI, LS-IL4R, and LS-RFP vaccinated birds. At 14 dph, the average body weights of birds vaccinated with BHI (121.7 g), LS-IL4R (121.4 g), or LS-RFP (127.3 g) are not significantly different from one another. Birds vaccinated with LS have significantly lower average body weight (107.3 g) compared to the average body weights of the BHI, LS-IL4R, and LS-RFP vaccinated birds. The average body weights of all groups at 21 dph (BHI (194.14 g); LS-IL4R (197.57 g); LS-RFP (192.36 g); and LS (179.43 g)) are not significantly different, however, birds vaccinated with LS had lower mean numeric weights compared the other groups. Significant differences between the groups are denoted by different letters; columns sharing letters are not significantly different from one another after being analyzed with the Tukey's test for multiple comparisons with a level of significance of 5%.

Figure 11A:
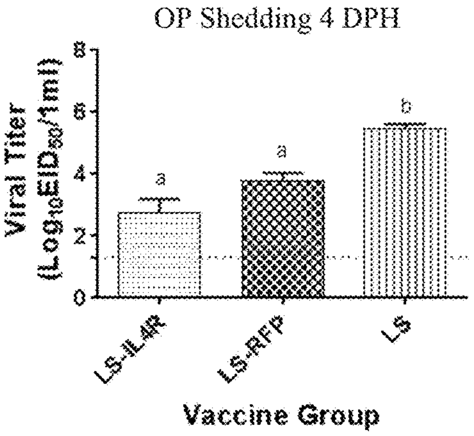
FIGS. 11A, 11B, and 11C illustrate the degree of viral shedding of LS-IL4R, LS-RFP, or LS through oropharyngeal (OP) and cloacal (CL) swab samples obtained from each vaccinated bird at 4 dph (FIG. 11A), 7 dph (FIG. 11B), and 14 dph (FIG. 11C). Eggs were vaccinated with $10^{3.5}$ $EID_{50}$ of LS-IL4R, LS-RFP, or LS per egg at 19 doe. Significant differences between groups are denoted by different letters; columns sharing letters are not significantly different from one another after being analyzed with the Tukey's test for multiple comparisons with a level of significance of 5%.
Figure 11A:
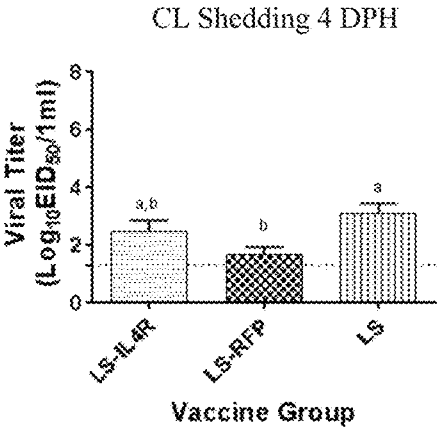
Figure 11B:
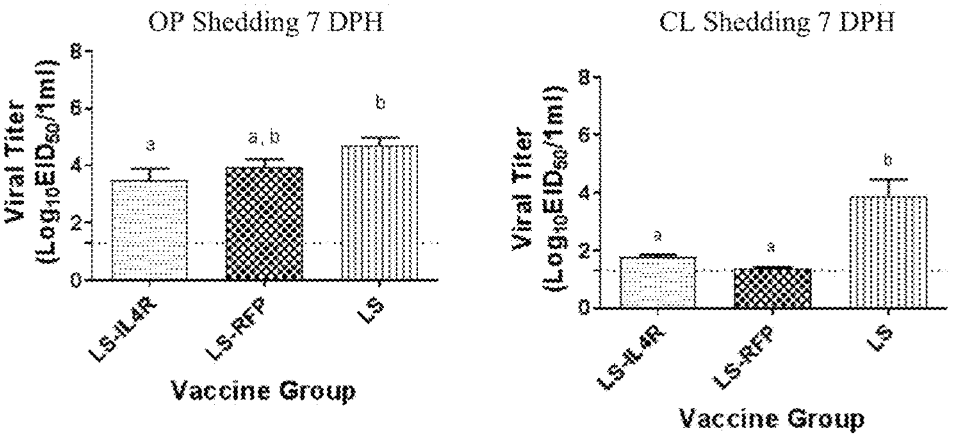
Figure 11C:
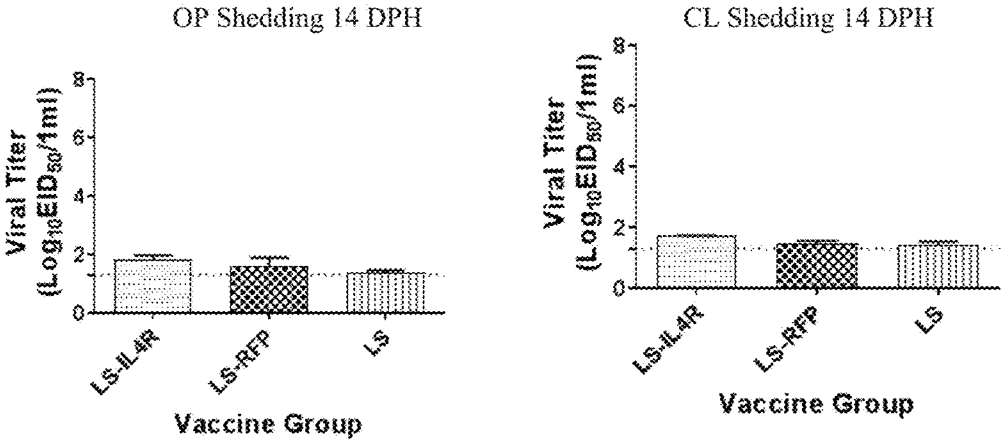

To assess viral shed titers, oropharyngeal (OP) and cloacal (CL) swab samples are obtained from each bird and placed in separate tubes containing 1.5 mL of brain-heart infusion broth (BHI) with antibiotics (2000 U/mL penicillin G, 200 mg/mL gentamicin sulfate, and 4 mg/mL amphotericin B; Sigma Chemical Co., St. Louis, Mo.). Viral RNA is extracted and quantified as previously described in Pantin-Jackwood, M. J., et al., *Vet. Microbiol.,* 177(1-2):7-17 (2015), contents of which are expressly incorporated herein. Briefly, RNA from the swabs is extracted using the MagMAX™ AI/ND Viral RNA Isolation Kit (Ambion, Inc., Austin, Tex.). Quantitative, real time RT-PCR (qRT-PCR) targeting the NDV M gene is performed using AgPath-ID™ One-Step RT-PCR Kit (Ambion, Inc., Austin, Tex.) and the Applied Biosystems® 7500 Fast Real-Time PCR system (ThermoFischer Scientific, Waltham, Mass.). The calculated qRT-PCR lower detection limit for NDV is between $10^{1.5}$ $EID_{50}$/mL and $10^{2.3}$ $EID_{50}$/mL. FIGS. 11A, 11B, and 11C illustrate the degree of viral shedding through OP swab and CL swab samples obtained from birds vaccinated in-ovo with LS-IL4R, LS-RFP, or LS at 4 dph (FIG. 11A), 7 dph (FIG. 11B), and 14 dph (FIG. 11C). Significant differences between groups are denoted by different letters; columns sharing letters are not significantly different from one another after being analyzed with the Tukey's test for multiple comparisons with a level of significance of 5%.

At 4 dph, the average OP viral shed titers are $10^{2.7}$ $EID_{50}$/mL for LS-IL4R group, $10^{3.7}$ $EID_{50}$/mL for LS-RFP group, and $10^{5.6}$ $EID_{50}$/mL for LS group. The average OP viral shed titers of LS-IL4R and LS-RFP groups are significantly different from the average OP viral shed titers of the LS group. The average CL viral shed titers at 4 dph of the LS-IL4R, LS-RFP and LS groups are $10^{2.5}$ $EID_{50}$/mL, $10^{1.7}$ $EID_{50}$/mL, and $10^{3.1}$ $EID_{50}$/mL, respectively. See FIG. 11A. The LS-RFP and LS groups are significantly different from one another.

At 7 dph, the average OP viral shed titers of the LS group ($10^{4.7}$ $EID_{50}$/mL) are significantly higher compared to the average OP viral shed titers of the LS-IL4R group ($10^{3.5}$ $EID_{50}$/mL) but not the LS-RFP group ($10^{3.9}$ $EID_{50}$/mL). The average CL viral shed titers at 7 dph of the LS group ($10^{3.9}$ $EID_{50}$/mL) are significantly higher compared to the average CL viral shed titers of the LS-IL4R group ($10^{1.8}$ $EID_{50}$/mL) and LS-RFP ($10^{1.4}$ $EID_{50}$/mL) groups. See FIG. 11B.

At 14 dph, the average OP viral shed titers are $10^{1.82}$ $EID_{50}$/mL for the LS-IL4R group, $10^{1.60}$ $EID_{50}$/mL for the LS-RFP group, and $10^{1.38}$ $EID_{50}$/mL for the LS group. The average CL viral shed titers are $10^{1.71}$ $EID_{50}$/mL for the LS-IL4R group, $10^{1.47}$ $EID_{50}$/mL for the LS-RFP group, and $10^{1.41}$ $EID_{50}$/mL for the LS group. See FIG. 11C. No significant differences in viral shed titers are observed at 14 dph.

Based on the above experiments, in-ovo administration of altered NDV LS-IL4R to SPF eggs imparts a better survival rate compared to NDV LS administration. Additionally, in-ovo administration of altered NDV LS-IL4R does not cause a reduction in hatchlings' body weight, on average; whereas in-ovo administration of NDV LS causes a decrease in hatchlings' average body weight, on average. Further, in-ovo administration in SPF egg of altered NDV LS-IL4R results in acceptable HI titers levels (which is indicative of antibodies created towards LS, and seroconverting) and viral shedding rates compared to in-ovo administration of NDV LS-RFP. Overall, altered NDV LS-IL4R immunogenic composition is safe to administer in-ovo and effectively modulates the host animal's immune response in vaccinated birds compared to unvaccinated birds.

Based on the data of the altered NDV ZJ1*L/IL-4R (supra) and the data for the altered NDV LS-IL4R, one can conduct a NDV LS challenge trial using in-ovo administration to eggs of the altered NDV LS-IL4R, and obtain results demonstrating that the altered NDV LS-IL4R causes the hatchlings to be protected against NDV LS infection or have reduced symptoms compared to unvaccinated birds. Also, one can conduct a NDV LS challenge trial on birds receiving the altered NDV LS-IL4R shortly after hatching, and obtain results demonstrating that the altered NDV LS-IL4R protects the vaccinated birds from NDV LS infection and/or results in the vaccinated birds having reduced symptoms compared to unvaccinated birds. See challenge trial protocols supra for the altered NDV ZJ1*L/IL-4R.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference.

We, the inventors, claim as follows:

1. A plasmid encoding an altered Newcastle Disease Virus (NDV) comprising an NDV sequence and a first polynucleotide encoding a reverse, complementary sequence of interleukin 4 (IL-4) or fragment thereof; wherein said altered NDV produces anti-sense RNA of IL-4 or fragment thereof.

2. The plasmid encoding said altered NDV of claim 1, wherein said IL-4 comprises SEQ ID NO: 1.

3. The plasmid encoding said altered NDV of claim 1, wherein said reverse, complementary sequence of said IL-4 or fragment thereof is selected from the group consisting of SEQ ID NOs: 2, 3, 5, or 23.

4. The plasmid encoding said altered NDV of claim 1, further comprising a second polynucleotide encoding said IL-4 or fragment thereof, wherein said second polynucleotide is operably linked to said first polynucleotide encoding said reverse, complementary sequence of said IL-4 or fragment thereof, and wherein said second polynucleotide is complementary to said first polynucleotide; wherein said altered NDV produces a dsRNA of IL-4 or fragment thereof.

5. The plasmid encoding said altered NDV of claim 4, wherein said first polynucleotide encoding said reverse, complementary sequence of said IL-4 or fragment thereof is selected from the group consisting of SEQ ID NOs: 2, 3, 5, or 23.

6. The plasmid encoding said altered NDV of claim 1, wherein said altered NDV comprises a LaSota NDV strain or an attenuated ZJ1 NDV strain.

7. A plasmid encoding an altered NDV encoding anti-sense RNA of IL-4 comprising SEQ ID NO: 17 or SEQ ID NO: 24.

8. An altered NDV comprising a first RNA encoding a reverse, complementary sequence of an anti-sense RNA of IL-4 or fragment thereof; wherein said altered NDV produces said anti-sense RNA of IL-4 or fragment thereof.

9. The altered NDV of claim 8, wherein said anti-sense RNA of IL-4 or fragment thereof comprises the reverse complementary sequence of SEQ ID NO: 1 or 4.

10. The altered NDV of claim 8, wherein said anti-sense RNA of IL-4 or fragment thereof is selected from the group consisting of SEQ ID NOs: 2, 3, 5, or 23.

11. The altered NDV of claim 8, further comprising a second RNA encoding a reverse, complementary sequence of an IL-4 or fragment thereof, wherein said first RNA is operably linked to said second RNA, and wherein said second RNA is complementary to said first RNA; wherein said altered NDV produces a dsRNA of said IL-4 or fragment thereof.

12. The altered NDV of claim 11, wherein said IL-4 or fragment thereof comprises SEQ ID NO: 1 or 4.

13. The altered NDV of claim 11, wherein said anti-sense RNA of IL-4 or fragment thereof is selected from the group consisting of SEQ ID NOs: 2, 3, 5, or 23.

14. The altered NDV of claim 8, further comprising a third RNA encoding a reverse, complementary sequence of a heterologous antigen from a heterologous avian pathogen, wherein said altered NDV produces said heterologous antigen.

15. The altered NDV of claim 14, wherein said heterologous avian pathogen is infectious laryngotracheitis virus (ILTV).

16. The altered NDV of claim 15, wherein said heterologous antigen comprises gB, gD, or a combination thereof.

17. The altered NDV of claim 8 comprising a reverse, complementary RNA equivalent sequence of SEQ ID NO: 18 or 25.

18. An immunogenic composition comprising said altered NDV of claim 1 and a pharmaceutically acceptable carrier, wherein said altered NDV produces said anti-sense RNA of IL-4 or fragment thereof.

19. The immunogenic composition of claim 18, further comprising an adjuvant.

20. The immunogenic composition of claim 18, wherein said altered NDV further comprises a RNA encoding a reverse, complementary sequence of a heterologous antigen from a heterologous avian pathogen, wherein said altered NDV produces said heterologous antigen.

21. A method of protecting an in-ovo inoculated hatchling chick from a disease caused by an avian pathogen comprising (i) administering to an embryonic bird in-ovo an effective dosage of said immunogenic composition of claim 18 to produce an inoculated embryonic bird, and (ii) incubating said inoculated embryonic bird until said inoculated embryonic bird hatches to produce an in-ovo inoculated hatchling chick, wherein said altered NDV in said immunogenic composition produces in-ovo at least one antigen from said avian pathogen and said anti-sense RNA of IL-4 or fragment thereof, wherein said anti-sense RNA of IL-4 or fragment thereof reduces IL-4 production by said inoculated embryonic bird in-ovo, and wherein said in-ovo inoculated hatchling chick produces antibodies against said avian pathogen antigen which protect said in-ovo inoculated hatching chick from said avian pathogen.

22. The method of claim 21, wherein said anti-sense RNA of IL-4 or fragment thereof comprises an RNA equivalent sequence selected from the group consisting of SEQ ID NO: 2, SEQ ID NO: 3, SEQ ID NO: 5, SEQ ID NO: 23, and a sequence complementary to SEQ ID NO: 1.

23. A method for increasing an in-ovo inoculated hatchling chick's survival rate after exposure to an avian pathogen comprising (i) administering to an embryonic bird in-ovo an effective dosage of said immunogenic composition of claim 18 to produce an inoculated embryonic bird, and (ii) incubating said inoculated embryonic bird until said inoculated embryonic bird hatches to produce an in-ovo inoculated hatchling chick, wherein said altered NDV in said immunogenic composition produces in-ovo at least one antigen from said avian pathogen and said anti-sense RNA of IL-4 or fragment thereof, wherein said anti-sense RNA of IL-4 or fragment thereof reduces IL-4 production by said inoculated embryonic bird in-ovo, and wherein said in-ovo inoculated hatchling chick produces antibodies against said avian pathogen antigen which protect said in-ovo inoculated hatching chick from said avian pathogen and increases said survival rate of said in-ovo inoculated hatching chick after exposure to said avian pathogen compared to the survival rate of a non-inoculated hatchling chick after exposure to said avian pathogen.

24. The method of claim 23, wherein said anti-sense RNA of IL-4 or fragment thereof comprises a RNA equivalent sequence selected from the group consisting of SEQ ID NO: 2, SEQ ID NO: 3, SEQ ID NO: 5, SEQ ID NO: 23, and a sequence complementary to SEQ ID NO: 1.

* * * * *